US011267857B2

(12) United States Patent
Schreiber et al.

(10) Patent No.: US 11,267,857 B2
(45) Date of Patent: *Mar. 8, 2022

(54) CSF1R-BASED CHIMERIC PROTEINS

(71) Applicant: Shattuck Labs, Inc., Austin, TX (US)

(72) Inventors: Taylor Schreiber, Austin, TX (US);
George Fromm, Austin, TX (US);
Suresh De Silva, Austin, TX (US)

(73) Assignee: Shattuck Labs, Inc., Austin, TX (US)

( * ) Notice: Subject to any disclaimer, the term of this patent is extended or adjusted under 35 U.S.C. 154(b) by 168 days.

This patent is subject to a terminal disclaimer.

(21) Appl. No.: 16/675,475

(22) Filed: Nov. 6, 2019

(65) Prior Publication Data
US 2020/0123214 A1 Apr. 23, 2020

Related U.S. Application Data

(63) Continuation of application No. 16/223,332, filed on Dec. 18, 2018, now Pat. No. 10,513,548, which is a continuation of application No. PCT/US2018/020039, filed on Feb. 27, 2018.

(60) Provisional application No. 62/463,997, filed on Feb. 27, 2017.

(51) Int. Cl.
| C07K 14/53 | (2006.01) |
| C07K 14/715 | (2006.01) |
| C07K 14/705 | (2006.01) |
| C07K 5/062 | (2006.01) |
| C07K 5/072 | (2006.01) |
| C07K 5/083 | (2006.01) |
| C07K 5/078 | (2006.01) |
| A61P 37/02 | (2006.01) |
| A61P 35/00 | (2006.01) |
| A61P 37/04 | (2006.01) |
| A61P 37/06 | (2006.01) |
| A61K 38/00 | (2006.01) |

(52) U.S. Cl.
CPC ............ *C07K 14/53* (2013.01); *A61P 35/00* (2018.01); *A61P 37/02* (2018.01); *A61P 37/04* (2018.01); *A61P 37/06* (2018.01); *C07K 5/0606* (2013.01); *C07K 5/06095* (2013.01); *C07K 5/06165* (2013.01); *C07K 5/081* (2013.01); *C07K 14/70575* (2013.01); *C07K 14/70578* (2013.01); *C07K 14/7153* (2013.01); *A61K 38/00* (2013.01); *C07K 2317/53* (2013.01); *C07K 2319/00* (2013.01); *C07K 2319/30* (2013.01); *C07K 2319/31* (2013.01); *C07K 2319/33* (2013.01)

(58) Field of Classification Search
None
See application file for complete search history.

(56) References Cited

U.S. PATENT DOCUMENTS

| 5,844,095 | A | 12/1998 | Linsley et al. |
| 7,569,663 | B2 | 8/2009 | Tykocinski et al. |
| 7,696,168 | B2 | 4/2010 | Kuliopulos et al. |
| 8,039,437 | B2 | 10/2011 | Tykocinski et al. |
| 8,080,246 | B2 | 12/2011 | Lin et al. |
| 8,329,657 | B2 | 12/2012 | Tykocinski et al. |
| 9,029,315 | B2 | 5/2015 | Chen et al. |
| 9,221,895 | B2 | 12/2015 | Tykocinski et al. |
| 9,352,037 | B2 | 5/2016 | Van Den Berg |
| 9,388,230 | B2 | 7/2016 | Elhalel |
| 9,493,575 | B2 | 11/2016 | Jaiswal et al. |
| 9,657,082 | B2 | 5/2017 | Tykocinski |
| 9,845,345 | B2 | 12/2017 | Ring et al. |
| 9,969,789 | B2 | 5/2018 | Uger et al. |
| 2007/0036783 | A1 | 2/2007 | Humeau et al. |
| 2008/0131431 | A1 | 6/2008 | Smith et al. |
| 2009/0226435 | A1 | 9/2009 | Khare |
| 2010/0136006 | A1 | 6/2010 | Lin et al. |
| 2010/0136007 | A1 | 6/2010 | Lin et al. |
| 2011/0041190 | A1 | 2/2011 | Tykocinski et al. |
| 2013/0039911 | A1 | 2/2013 | Bedi et al. |
| 2013/0065815 | A1 | 3/2013 | Tykocinski et al. |
| 2013/0243697 | A1 | 9/2013 | Tykocinski et al. |
| 2014/0079699 | A1* | 3/2014 | Wong ............. A61P 37/02 424/134.1 |
| 2014/0113370 | A1* | 4/2014 | Camphausen ....... G01N 33/573 435/328 |
| 2014/0154252 | A1 | 6/2014 | Thompson et al. |
| 2014/0227315 | A1 | 8/2014 | Tykocinski et al. |
| 2014/0242077 | A1 | 8/2014 | Choi et al. |
| 2014/0286858 | A1 | 9/2014 | Zimmerman et al. |
| 2015/0098942 | A1 | 4/2015 | Curti et al. |
| 2015/0174268 | A1 | 6/2015 | Li |

(Continued)

FOREIGN PATENT DOCUMENTS

| WO | WO 2001049318 | 7/2001 |
| WO | WO 2005/047334 * 5/2005 ............. A61K 47/42 |

(Continued)

OTHER PUBLICATIONS

Chen et al. (PNAS, 105(47): 18267-18272, 2008).*
Karpusas et al. (Structure, 3:1031-1039, 1995).*
Ma et al. (Seminars in Immunology, 21: 265-272, 2009).*
International Search Report & Written Opinion issued in PCT Appl. No. PCT/US2018/020039, dated Jun. 11, 2018, 10 pages.

(Continued)

*Primary Examiner* — Nelson B Moseley, II
(74) *Attorney, Agent, or Firm* — Morgan, Lewis & Bockius LLP

(57) ABSTRACT

The present invention relates, in part, to chimeric proteins which include the extracellular domain of colony stimulating factor 1 receptor (CSF1R) and their use in the treatment of diseases, such as immunotherapies for cancer and/or an inflammatory disease.

18 Claims, 19 Drawing Sheets

Specification includes a Sequence Listing.

(56) References Cited

U.S. PATENT DOCUMENTS

| | | |
|---|---|---|
| 2015/0183881 A1 | 7/2015 | Bedi et al. |
| 2015/0190506 A1 | 7/2015 | Cheung et al. |
| 2015/0191525 A1 | 7/2015 | Epstein et al. |
| 2015/0266942 A1 | 9/2015 | Tian |
| 2015/0353642 A1 | 12/2015 | Tykocinski |
| 2015/0368350 A1 | 12/2015 | Tykocinski et al. |
| 2015/0376260 A1 | 12/2015 | Elhalel et al. |
| 2016/0024176 A1 | 1/2016 | Damschroder et al. |
| 2016/0166685 A1 | 6/2016 | Cheung et al. |
| 2016/0177276 A1 | 6/2016 | Lo et al. |
| 2016/0186150 A1 | 6/2016 | Deming et al. |
| 2016/0250322 A1 | 9/2016 | Schreiber et al. |
| 2016/0256527 A1 | 9/2016 | Gurney |
| 2016/0340409 A1 | 11/2016 | Dranitzki-Elhalel |
| 2016/0340430 A1 | 11/2016 | Bedi et al. |
| 2016/0347846 A1 | 12/2016 | Tykocinski |
| 2017/0107270 A1 | 4/2017 | Pons et al. |
| 2018/0142019 A1 | 5/2018 | Manning et al. |

FOREIGN PATENT DOCUMENTS

| | | | | |
|---|---|---|---|---|
| WO | WO 2005047334 | | 5/2005 | |
| WO | WO 2008/061377 | * | 5/2008 | ............. A61K 38/00 |
| WO | WO 2008061377 | | 5/2008 | |
| WO | WO 2010003118 | | 1/2010 | |
| WO | WO 2010005519 | | 1/2010 | |
| WO | WO 2010/062401 | * | 6/2010 | ......... A61K 38/1793 |
| WO | WO 2010070047 | | 6/2010 | |
| WO | WO 2010105068 | | 9/2010 | |
| WO | WO 2012042480 | | 4/2012 | |
| WO | WO 2013000234 | | 1/2013 | |
| WO | WO 2013019615 | | 2/2013 | |
| WO | WO 2013164694 | | 11/2013 | |
| WO | WO 2013173820 | | 11/2013 | |
| WO | WO 2014094122 | | 6/2014 | |
| WO | WO 2014106839 | | 6/2014 | |
| WO | WO 2014121085 | | 8/2014 | |
| WO | WO 2014121093 | | 8/2014 | |
| WO | WO 2014121099 | | 8/2014 | |
| WO | WO 2014134165 | | 9/2014 | |
| WO | WO 2014164427 | | 10/2014 | |
| WO | WO 2015095423 | | 6/2015 | |
| WO | WO 2015104406 | | 7/2015 | |
| WO | WO 2015112534 | | 7/2015 | |
| WO | WO 2015116178 | | 8/2015 | |
| WO | WO 2015183902 | | 12/2015 | |
| WO | WO 2015200828 | | 12/2015 | |
| WO | WO 2016025385 | | 2/2016 | |
| WO | WO 2016126608 | | 8/2016 | |
| WO | WO 2017/059168 | * | 9/2016 | ............. A61K 38/00 |
| WO | WO 2016/168149 A1 | | 10/2016 | |
| WO | WO 2016166139 | | 10/2016 | |
| WO | WO 2017/059168 A1 | | 4/2017 | |

OTHER PUBLICATIONS

Martin-Moreno, et al., "CSF1R Protein Expression in Reactive Lymphoid Tissues and Lymphoma: Its Relevance in Classical Hodgkin Lymphoma," PLoS One, vol. 10, No. 6, 14 pages, Jun. 12, 2015.

Ali, et al. "Anti-tumour therapeutic efficacy of OX40L in murine tumour model." Vaccine, 22: 3585-3594, 2004.

Anderson, et al. "Lag-3, Tim-3, and TIGIT: Co-Inhibitory Receptors with Specialized Functions in Immune Regulation," Immunity vol. 44, 2016, pp. 989-1004.

Barclay, "Signal Regulatory protein akpha (SIRPα)/CD47 interaction and function," Current Opinion in Immunology, 21:47-52, 2009.

Barclay, et al., "The Interaction Between Signal Regulatory Protein Alpha (SIRPα) and CD47: Structure, Function, and Therapeutic Target," Annu. Rev. Immunol, 32:25-50, 2014.

Bartkowiak, et al. "4-1 BB agonists: Multi-Potent Potentiators of Tumor Immunity," Frontiers in Oncology, 2015, vol. 5, Article 117, pp. 1-16.

Batlevi, et al. "Novel Immunotherapies in Lymphoid Malignancies," Nature Reviews, Clinical Oncology, vol. 13, 2016, pp. 25-40.

Callahan, et al. "Targeting T Cell Co-receptors for Cancer Therapy," Immunity, vol. 44, 2016, pp. 1069-1078.

Chao, et al. "The CD47-SIRPα pathway in cancer immune evasion and potential therapeutic implications." Current Opinion in Immunology, 24: 225-232, 2012.

Curran et al. "Editorial: Advances in Combination Tumor Immunotherapy," Frontiers in Oncology, 2015, vol. 5, Article 198, pp. 1-2.

De Visser, et al., "The interplay between innate and adaptive immunity regulates cancer development," Cancer Immunology, Immunotherapy, vol. 54, No. 11, pp. 1143-1152, May 12, 2005.

De Visser et al., "Paradoxial Roles of the Immune System During Cancer Development," Nature Reviews Cancer, (2006) 6:24-37.

Guo, et al. "PD-1 Blockade and OX40 Triggering Synergistically Protects Against Tumor Growth in a Murine Model of Ovarian Cancer," PLOS ONE, 2014, vol. 9, issue 2, pp. 1-10.

Hatherley, et al., "The Structure of the Macrophage Signal Regulatory Protein α (SIRPα) Inhibitory Receptor Reveals a Binding Face Reminiscent of That Used by T Cell Receptors," The Journal Of Biological Chemistry, vol. 282, No. 19, pp. 14567-14575, 2007.

Hirano, et al. "Inhibition of human breast carcinoma growth by a soluble recombinant human CD40 ligand." Blood, 93(9): 2999-3007, 1999.

Huang, et al. "CTLA-4-FAS ligand functions as a trans signal converter protein in bridging antigen-presenting cells and T cells," International Immunology, vol. 13, No. 4, 2001, pp. 529-539.

International Search Report and Written Opinion, International Application No. PCT/US2016/054598, dated Jan. 9, 2017, 17 pages.

Karman, et al. "Ligation of Cytoxic T Lymphocyte Antigen-4 to T Cell Receptor Inhibits T Cell Activation and Directs Differentiation into Foxp3+ Regulatory T Cells," The Journal of Biological Chemistry, vol. 287, No. 14, 2012, pp. 11098-11107.

Karpusas, et al., "2 Å crystal structure of an extracellular fragment of human CD40 ligand," Structure, 3:1031-1039, 1995.

Kermer, et al. "An Antibody Fusion Protein for Cancer Immunotherapy Mimicking IL-15 trans-Presentation at the Tumor Site," Molecular Cancer Therapeutics, vol. 11, No. 6, 2012, pp. 1279-1288.

Khalil, et al. "The Future of Cancer Treatment: Immunomodulation, CARs and Combination Immunotherapy," Nature Reviews Clinical Oncology, 2016, pp. 1-18.

Ledford, "The Perfect Blend," Nature, vol. 532, 2016, pp. 162-164.

Lee, et al., "Novel Structural Determinants of SIRPα that Mediate Binding of CD47," The Journal of Immunology, 179, 7741-7750, 2007.

Linch, et al. "OX40 Agonists and Combination Immunotherapy: Putting the Pedal to the Metal," Frontiers in Oncology, vol. 5, article 34, 2015, pp. 1-14.

Ma, et al. "The role of CD40 and CD40L in Dendritic Cells" Sem. in Immuno., 21: 265-272, 2009.

Marcus, et al., "Recognition of tumors by the innate immune system and natural killer cells," Advances in Immunology, vol. 122, pp. 91-128, Jan. 1, 2015.

Mahoney, Combination Cancer Immunotherapy and New Immunomodulatory Targets Nature Reviews Drug Discovery (2015) 14: 561-585.

Orbach, et al. "CD40•FasL and CTGLA•4FasL Fusion Proteins Induce Apoptosis in Malignant Cell Lines by Dual Signaling," American Journal of Pathology, vol. 177, No. 6, 2010, pp. 3159-3168.

Pardoll, "The Blockade of Immune Checkpoints in Cancer Immunotherapy," Nature Reviews Cancer, vol. 12, 2012, pp. 252-264.

Schildberg, et al. "Coinhibitory Pathways in B7-CD28 Ligand-Receptor Family," Immunity, vol. 44, 2016, pp. 955-972.

Scott, et al. "Antibody Therapy of Cancer," Nature Reviews Cancer, vol. 12, 2012, pp. 278-287.

Spiess, et al. "Alternative Molecular Formats and Therapeutic Applications for Bispecific Antibodies," Molecular Immunology, vol. 67, 2015, pp. 95-106.

(56) References Cited

OTHER PUBLICATIONS

Ward-Kavanagh, et al. "The TNF Receptor Superfamily in Co-stimulating and Co-inhibitory Responses," Immunity, vol. 44, 2016, pp. 1005-1019.

Zhang, et al. "Targeted and Untargeted CD137L Fusion Proteins for the Immunotherapy of Experimental Solid Tumors," Clin Cancer Res 2007, vol. 13, No. 9, pp. 2578-2767.

Zhao et al., "A Bispecific Protein Capable of Engaging CTLA-4 and MHCII Protects Non-Obese Diabetic Mice from Autoimmune Diabetes," PLOS ONE, vol. 8, Issue 5, 2013, pp. 1-11.

* cited by examiner

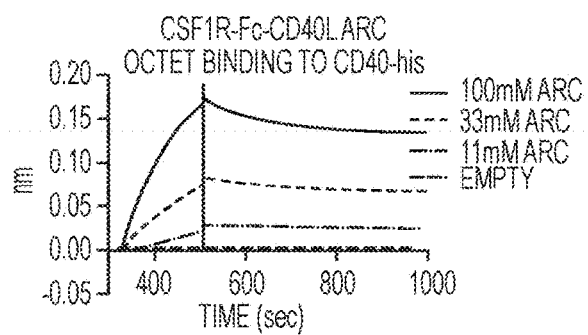
FIG. 5A
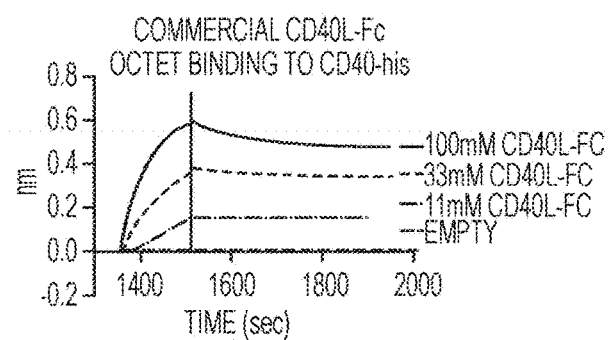
FIG. 5B
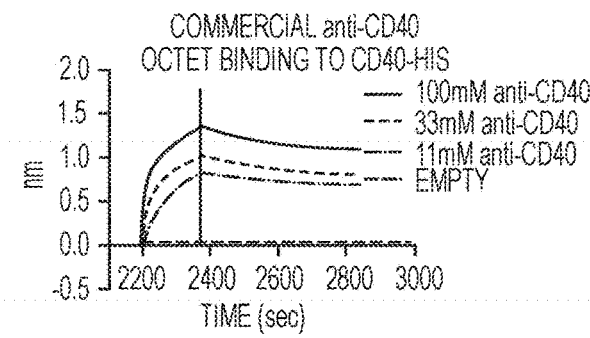
FIG. 5C
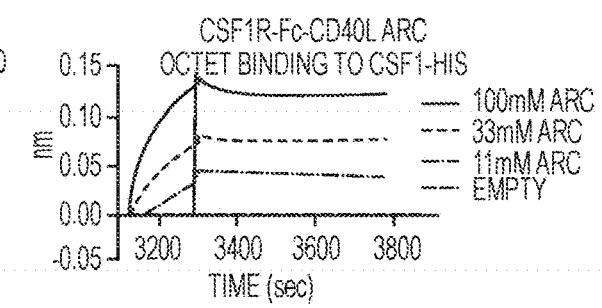
FIG. 5D
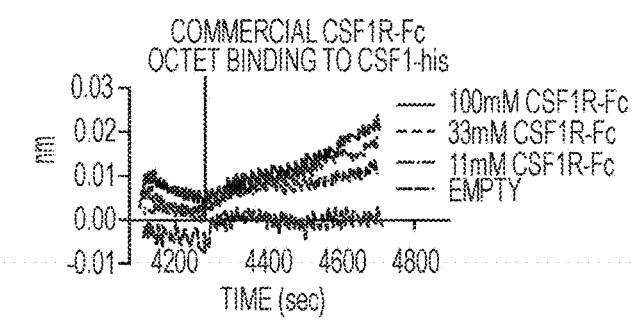
FIG. 5E
| SAMPLE ID | LIGAND | KD |
|---|---|---|
| hCSF1-Fc-CD40L | hCD40-his | 4.83 nM |
| hCD40L-Fc | hCD40-his | 2.42 nM |
| anti-hCD40 | hCD40-his | 1.22 nM |
| hCSF1R-Fc-CD40L | hCSF1-his | 6.46 pM |
| hCSF1R-Fc | hCSF1-his | ND |
FIG. 5F

| GROUP | TOTAL, N | SHORT-TERM, N (IMMUNE PROFILING) | LONG-TERM, N (TUMOR GROWTH/SURVIVAL) | % REJECTION (PRIMARY TUMOR) | % REJECTION (RE-CHALLENGE) |
|---|---|---|---|---|---|
| UNTREATED | 33 | 12 | 21 | 0.0 | 0.0 |
| αCD115 (AFS98) | 7 | / | 7 | 14.3 | 0 |
| αCD40 (FGK4.5) | 12 | / | 12 | 8.3 | 0 |
| αCD115/CD40 | 7 | / | 7 | 14.3 | 0 |
| CD115-Fc-CD40L (150µg x2) | 9 | 2 | 7 | 71.4 | 0 |

FIG. 11C

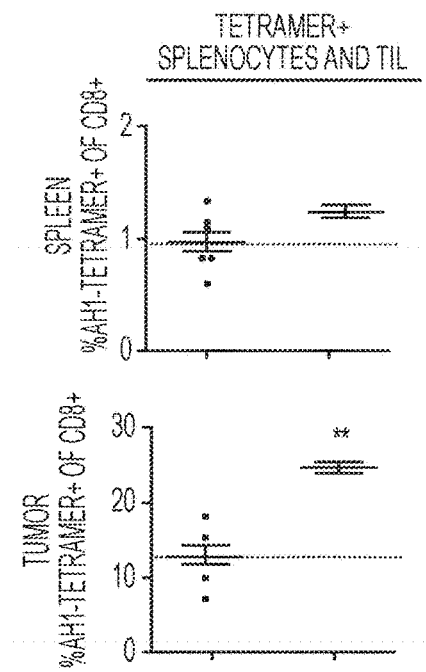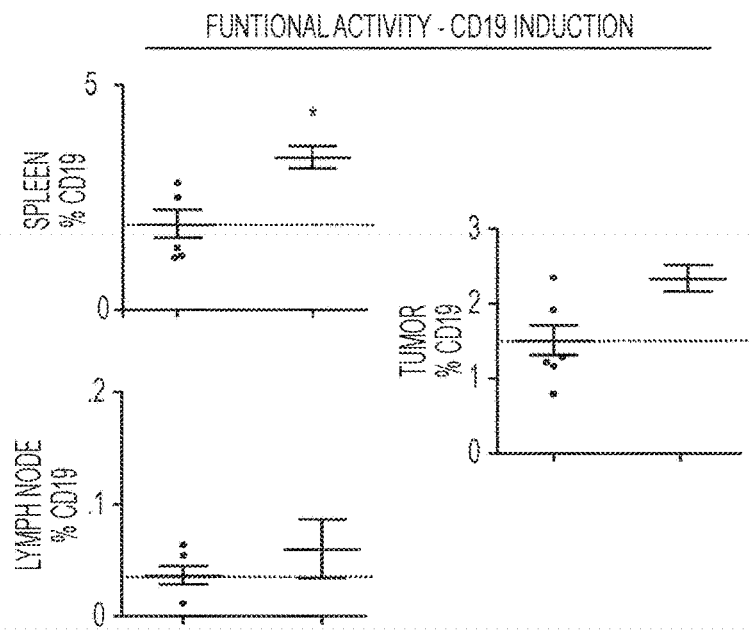
FIG. 12C    FIG. 12D
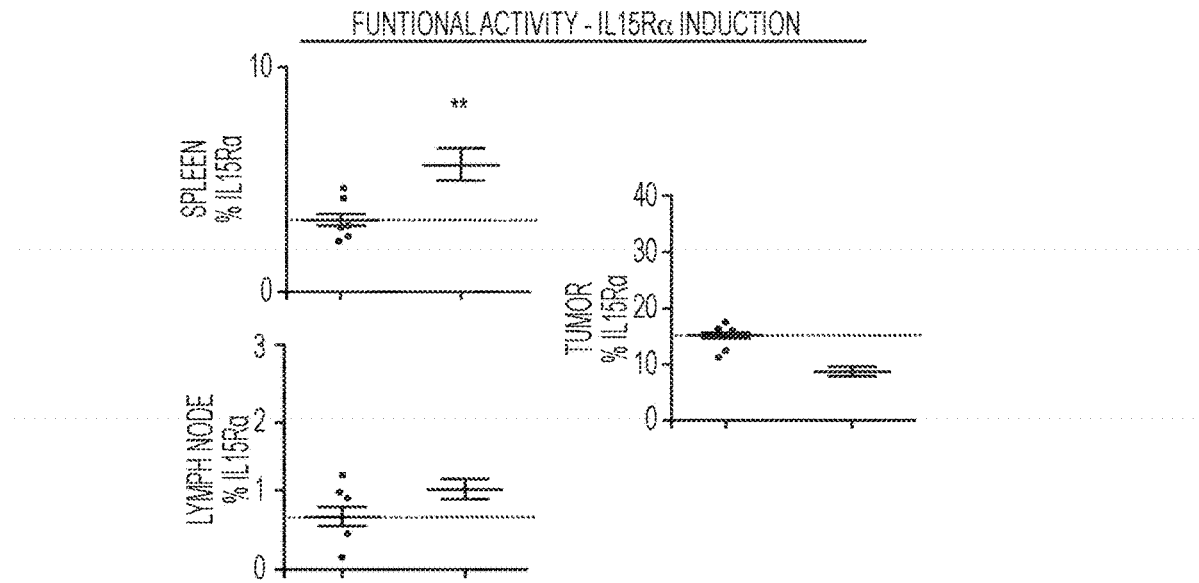
FIG. 12E

| Joining Linker 1 | Fc | Joining Linker 2 | Linker Module = Joining Linker 1 + Fc + Joining Linker 2 |
|---|---|---|---|
| SKYGPPCPSCP (SEQ ID NO: 28) | APEFLGGPSVFLFPPKPKDTLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSSWQEGNVFSC SVMHEALHNHYTQKSLSLSLGK (SEQ ID NO: 25) | IEGRMD (SEQ ID NO: 31) | SKYGPPCPSCPAPEFLGGPSVFLFPPKPKDTLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVMHEALHNHYTQKSLSLSLGKIEGRMD (SEQ ID NO: 75) |
| SKYGPPCPSCP (SEQ ID NO: 28) | APEFLGGPSVFLFPPKPKDQLMISRTPEVTCVVVDVSQE DPEVQFNWYVDGVEVHNAKTKPREEQFNSTYRVVSVLTT PHSDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSSWQEGNVFSC SVLHEALHNHYTQKSLSLSLGK (SEQ ID NO: 26) | IEGRMD (SEQ ID NO: 31) | SKYGPPCPSCPAPEFLGGPSVFLFPPKPKDQLMISRTPEVTCVVVDVS QEDPEVQFNWYVDGVEVHNAKTKPREEQFNSTYRVVSVLTTPHSDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVLHEALHNHYTQKSLSLSLGKIEGRMD (SEQ ID NO: 76) |
| SKYGPPCPSCP (SEQ ID NO: 28) | APEFLGGPSVFLFPPKPKDQLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSRWQEGNVFSC SVLHEALHNHYTQKSLSLSLGK (SEQ ID NO: 27) | IEGRMD (SEQ ID NO: 31) | SKYGPPCPSCPAPEFLGGPSVFLFPPKPKDQLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSRWQEGNVFSCSVLHEALHNHYTQKSLSLSLGKIEGRMD (SEQ ID NO: 77) |
| SKYGPPCPPCP (SEQ ID NO: 29) | APEFLGGPSVFLFPPKPKDTLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSSWQEGNVFSC SVMHEALHNHYTQKSLSLSLGK (SEQ ID NO: 25) | IEGRMD (SEQ ID NO: 31) | SKYGPPCPPCPAPEFLGGPSVFLFPPKPKDTLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVMHEALHNHYTQKSLSLSLGKIEGRMD (SEQ ID NO: 78) |
| SKYGPPCPPCP (SEQ ID NO: 29) | APEFLGGPSVFLFPPKPKDQLMISRTPEVTCVVVDVSQE DPEVQFNWYVDGVEVHNAKTKPREEQFNSTYRVVSVLTT PHSDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSSWQEGNVFSC SVLHEALHNHYTQKSLSLSLGK (SEQ ID NO: 26) | IEGRMD (SEQ ID NO: 31) | SKYGPPCPPCPAPEFLGGPSVFLFPPKPKDQLMISRTPEVTCVVVDVS QEDPEVQFNWYVDGVEVHNAKTKPREEQFNSTYRVVSVLTTPHSDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVLHEALHNHYTQKSLSLSLGKIEGRMD (SEQ ID NO: 79) |
| SKYGPPCPPCP (SEQ ID NO: 29) | APEFLGGPSVFLFPPKPKDQLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSRWQEGNVFSC SVLHEALHNHYTQKSLSLSLGK (SEQ ID NO: 27) | IEGRMD (SEQ ID NO: 31) | SKYGPPCPPCPAPEFLGGPSVFLFPPKPKDQLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSRWQEGNVFSCSVLHEALHNHYTQKSLSLSLGKIEGRMD (SEQ ID NO: 80) |

CSF1R-BASED CHIMERIC PROTEINS

PRIORITY

This application is a continuation of U.S. application Ser. No. 16/223,332, filed Dec. 18, 2018, now U.S. Pat. No. 10,513,548, which is a continuation of International Application No. PCT/US18/20039, filed Feb. 27, 2018, which claims the benefit of and priority to U.S. Provisional Application No. 62/463,997, filed Feb. 27, 2017, the contents of all which are incorporated herein by reference in their entirety.

JOINT RESEARCH AGREEMENT

The subject matter claimed herein was made as a result of activities undertaken within the scope of a joint research agreement. The parties to the joint research agreement are: (1) Shattuck Labs, Inc; and (2) Heat Biologics, Inc.

INCORPORATION-BY-REFERENCE OF MATERIAL SUBMITTED ELECTRONICALLY

This application contains a sequence listing. It has been submitted electronically via EFS-Web as an ASCII text file entitled "SHK-002PC_SequenceListing_ST25". The sequence listing is 92,976 bytes in size, and was created on or about Feb. 27, 2018. The sequence listing is hereby incorporated by reference in its entirety.

TECHNICAL FIELD

The present invention relates, in part, to, chimeric proteins which include the extracellular domain of colony stimulating factor 1 receptor (CSF1R) and their use in the treatment of diseases, such as immunotherapies for cancer and/or inflammatory diseases.

BACKGROUND

Recent clinical data have demonstrated impressive patient responses to agents targeting immune coinhibitory molecules, including, for example, clinical trials that led to the approval of YERVOY, KEYTRUDA, and OPDIVO. These immunotherapies are collectively characterized as checkpoint inhibitors, and unfortunately, these therapies only provide clinical benefit for ~15-30% of cancer patients. One potential approach to improving clinical response rates for a broader population of cancer patients includes combining a checkpoint inhibitor therapeutic with another therapy. Such combinations, when applied using multiple individual therapeutics, might lead to improved clinical benefit but are cumbersome to develop. Further, many immunotherapies are complicated by severe side effects that significantly narrow a patient's therapeutic window for treatment.

There remains a need for novel methods and compositions that provide effective immunotherapies, including consolidating multiple therapeutic mechanisms into single drugs.

SUMMARY

Accordingly, the present invention provides, in part, compositions and methods that find use in cancer treatment by, for instance, overcoming multiple suppressive mechanisms, in the tumor microenvironment, and stimulating immune antitumor mechanisms. Similarly, the compositions and methods find use in treating an inflammatory disease. For instance, the present invention provides, in part, compositions and methods that allow for dual targeting of suppressive myeloid populations by inhibiting CSF1/CSF1R signaling and activation of antigen-presenting cells by stimulating CD40/CD40L signaling. Such concurrent CSF1R blockade and CD40 agonism causes, inter alia, an overall decrease in immunosuppressive cells and a shift toward a more inflammatory milieu and an increased antitumor effect.

In aspects, the present invention provides a heterologous chimeric protein comprising: (a) a first domain comprising a portion of colony stimulating factor 1 receptor (CSF1R) that is capable of binding a CSF1R ligand; (b) a second domain comprising a portion of CD40 Ligand (CD40L) that is capable of binding a CD40L receptor; and (c) a linker linking the first domain and the second domain. In aspects, the present invention provides methods of treating cancer with this heterologous chimeric protein. In aspects, the present invention provides methods of treating an inflammatory disease with this heterologous chimeric protein.

In embodiments, the present invention provides a recombinant fusion protein comprising a general structure of: N terminus-(a)-(b)-(c)-C terminus, where (a) is a first domain comprising an extracellular domain of CSF1R that is at least 95% identical to the amino acid sequence of SEQ ID NO: 2 and is capable of binding a CSF1R ligand, (b) is a linker linking the first domain and the second domain and comprising a hinge-CH2-CH3 Fc domain derived from human IgG4 (e.g. 95% identical to the amino acid sequence of SEQ ID NO: 25, SEQ ID NO: 26, or SEQ ID NO: 27, and (c) is a second domain comprising an extracellular domain of CD40 ligand (CD40L) that is at least 95% identical to the amino acid sequence of SEQ ID NO: 4 and is capable of binding an CD40L receptor. In embodiments, the present invention provides methods of treating cancer with this heterologous chimeric protein. In embodiments, the present invention provides methods of treating an inflammatory disease with this heterologous chimeric protein.

Any aspect or embodiment described herein can be combined with any other aspect or embodiment as disclosed herein.

BRIEF DESCRIPTION OF THE DRAWINGS

FIG. 5A to FIG. 5F show the Octet binding affinity of human CSF1R-Fc-CD40L. On-rates, off-rates, and affinity (KD) were determined for human CSF1R-Fc-CD40L to CD40-His (FIG. 5A), commercially available single-sided CD40L-Fc to CD40-His (FIG. 5B), a commercially available CD40 antibody to CD40-His (FIG. 5C), hCSF1R-Fc-CD40L to CSF1-His (FIG. 5D), and commercially available CSF1R-Fc to CSF1-His (FIG. 5E). Human CSF1R-Fc-CD40L bound CD40 at 4.83 nM and CSF1 at 646 pM (FIG. 5F). The term "CSF1R-Fc-CD40L ARC" refers to the CSF1R-Fc-CD40L chimeric protein. In all of FIG. 5A to FIG. 5E, the order of curves, top to bottom is: 100 mM test agent, 33 mM test agent, 11 mM test agent, and empty.

FIG. 7A shows Western blot detection of all three domains of the mCSF1R-Fc-CD40L chimeric protein under non-reduced (lane 2), reduced (lane 3), and reduced-FPNGase treatments (lane 4). The reduced, deglycosylated form of the protein migrates at the expected molecular weight of about 105 kDa.

FIG. 7B shows ELISA assays were performed to detect the binding of CSF1R to recombinant CSF1 (left panel), Fc to IgG (center panel), and CD40L to rCD40 (right panel) using detection methods outlined in the schematics above each graph. CD115 is synonymous with CSF1R. In FIG. 7B, left panel mCD115-Fc-CD40L is the top curve, in the middle and right panels mCD115-Fc-CD40L is the bottom curve.

FIG. 10A shows a CSF1 trap/sink assay. Non-tumor bearing mice were injected with a single dose of anti-CD115(CSF1R) on day 0. On day 2, mice were either left untreated, or injected with a single dose of the CSF1R-Fc-CD40L chimeric protein. Blood serum was collected on day 2 before injection of the chimeric protein and on day 3 after the chimeric protein treatment. Murine CSF1 ELISAs were performed on the serum, and showed that the murine CSF1R-Fc-CD40L chimeric protein binds and eliminates serum CSF1. (FIG. 10B shows in vivo IL15Rα Induction. Tumor-bearing mice were treated with two doses of 150 μg of mCSF1R-Fc-CD40L ARC on days 5 and 7 after initial tumor inoculation. On day 13, a cohort of mice was sacrificed and their spleens and lymph nodes were removed and dissociated for flow cytometry analysis of IL15Rα. Consistent with a known mechanism of CD40L function, mice treated with the CSF1R-Fc-CD40L chimeric protein displayed an increase in IL15Rα in both tissue compartments. CD115 is synonymous with CSF1R. For the graph of FIG. 10A, the top curve is +αCD115, middle curve is +αCD115 then CD115-Fc-CD40L on day 2, and bottom curve is untreated. For FIG. 10B (top and bottom panels), the left points are control and the right are CSF1R-Fc-CD40L.

FIG. 11A to FIG. 11C show anti-tumor efficacy of murine CSF1R-Fc-CD40L in colorectal CT26 tumors. Balb/c mice were inoculated with CT26 tumors on day 0. Following 4 days of tumor growth, when tumors reached a diameter of 4-5 mm, mice were treated with either control antibodies or the mCSF1R-Fc-CD40L chimeric protein. Treatments were then repeated again on day 7. The figure above includes: (FIG. 11A) individual tumor growth curves for each treatment group, (FIG. 11A) overall survival through day 60 of the experiment and (FIG. 11A) a table summarizing the treatment outcomes for each group. CD115 is synonymous with CSF1R. For FIG. 11B, with reference to day 35, the curves are (top to bottom): CD115-Fc-CD40L (150 μg×2), αCD115, αCD115/CD40, αCD40 (untreated mice have not survived by this point).

FIG. 12A to FIG. 12E show in vivo immunophenotyping in tumor-bearing mice. Tumor-bearing immunophenotyping was also performed for each treatment group by analyzing splenocytes, lymph node cells and tumor infiltrating lymphocytes for mice from each group on day 13 post tumor inoculation. FIG. 12A shows results demonstrating that mice treated with murine CSF1R-Fc-CD40L had increased frequencies of both CD4+ and CD8+ T cells in the spleen, but not lymph node or tumor as compared to controls. FIG. 12B shows a decrease in the proportion of CD4+CD25+ cells in the spleen and tumor, which may indicate a decrease in immunoregulatory T cells. Interestingly, despite a non-significant increase in the proportion of total CD8+ cells within the tumor (see, FIG. 12C), a significant increase in the proportion of CD8+ T cells specific for the AH1 tumor antigen (by tetramer staining) was detected. To determine potential evidence of CD40 receptor activation, induction of CD19+ cells (FIG. 12D) and IL-15Rα-positive cells (FIG. 12E) were analyzed. For all of FIG. 12A to FIG. 12E, the left points are control and the right are CSF1R-Fc-CD40L.

13A) and in some cases this inflammatory response was lethal. Importantly, mice treated with the murine CD115-Fc-CD40L chimeric protein (which is another name for the mCSF1R-Fc-CD40L chimeric protein) appeared healthy, did not develop any signs of diarrhea or weight loss, and behaved normally (see photos in left panel). These data are in accordance with clinical data in humans treated with CD40 agonist antibodies, and suggest that a beneficial safety profile of mCD115-Fc-CD40L. CD115 is synonymous with CSF1R. In FIG. 13B, the order of bars is: untreated, αCD115, αCD40, αCD115+αCD40, CD115-Fc-CD40L FP.

FIG. 20 is a table showing joining linkers and Fc linkers that can be combined into exemplary modular linkers. The exemplary modular linkers shown can be combined with any herein-described Type I and Type II proteins and/or extracellular domains of a herein described Type I and Type II proteins to form a chimeric protein of the present invention.

DETAILED DESCRIPTION

Figure 1A:
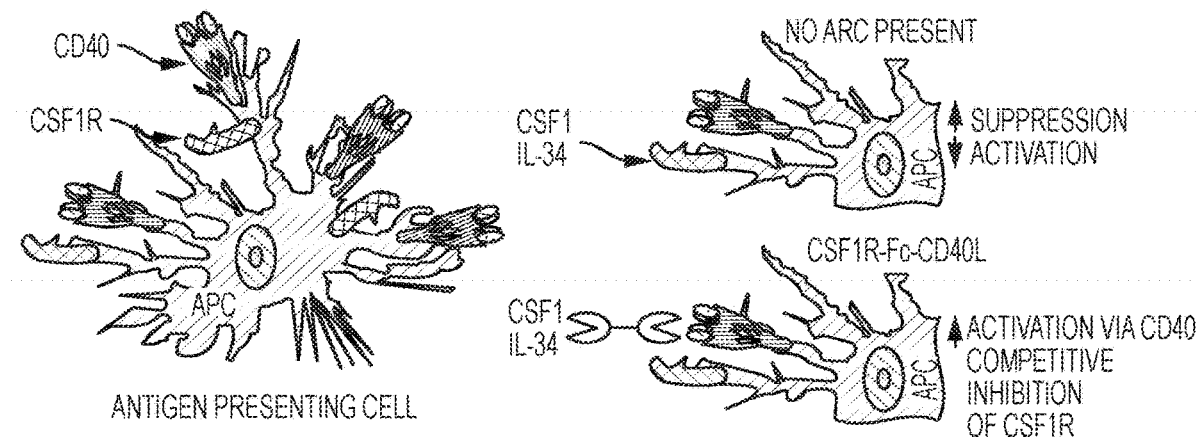
FIG. 1A shows, without wishing to be bound by theory, a schematic for a mechanism of action for the CSF1R-Fc-CD40L chimeric protein.

The present invention is based, in part, on the discovery of engineered chimeric proteins comprising a first domain comprising a portion of colony stimulating factor 1 receptor (CSF1R) that is capable of binding a CSF1R ligand. In embodiments, the chimeric protein further comprises a second domain comprising a portion of CD40 Ligand (CD40L) that is capable of binding a CD40L receptor. In embodiments, the first domain and the second domain are connected by a linker. In embodiments, the present chimeric protein provides an immune stimulatory signal, for example, capable of activating macrophages and antigen presenting cells, while providing a localized trap for an inhibitory signal that could otherwise shift the balance toward immunosuppression (e.g., CSF1 or IL-34). Embodiments of the invention thereby provide for the effective treatment of cancers and/or inflammatory diseases.

Chimeric Proteins

In embodiments, the present invention relates to chimeric proteins engineered to comprise a domain, e.g., the extracellular domain, of the immune inhibitory receptor colony stimulating factor 1 receptor (CSF1R), also known as macrophage colony-stimulating factor receptor (M-CSFR) and cluster of differentiation 115 (CD115). Thus, throughout this disclosure, CSF1R and CD115 are synonymous, when referenced alone and/or when referenced in context of a chimeric protein, thus, for example, CSF1R-Fc-CD40L is the same chimeric protein as CD115-Fc-CD40L. CSF1R is a single-pass type I membrane protein which functions as a receptor for colony stimulating factor 1 (CSF1). CSF1R has also been shown to be a receptor for IL-34. Binding of CSF1R to either CSF1 or IL-34 plays a critical role in the survival, proliferation, and differentiation of hematopoietic precursor cells, especially mononuclear phagocytes, such as macrophages and monocytes. Further, CSF1R has been shown to bind to either CSF1 or IL-34 within the tumor microenvironment. Binding of the receptor to these ligands induces immune suppression through, inter alia, the induction of tumor associated macrophages (TAMs) and myeloid derived suppressor cells (MDSCs).

In embodiments, the present chimeric protein comprises a domain, e.g., the extracellular domain, of human CSF1R. The human CSF1R comprises the amino acid sequence of SEQ ID NO: 1 (with the amino acid sequence of the extracellular domain comprising amino acids 20 to 517).

In embodiments, the present chimeric protein comprises the extracellular domain, of human CSF1R, which has the amino acid sequence of SEQ ID NO: 2. In embodiments, the present chimeric proteins may comprise the extracellular domain of CSF1R as described herein, or a variant or a functional fragment thereof. For instance, the chimeric protein may comprise a sequence of the extracellular domain of CSF1R as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of the extracellular domain of CSF1R as described herein.

The structure of CSF1R is described, for example, in W. D. Tap, et al., "Structure-Guided Blockade of CSF1R Kinase in Tenosynovial Giant-Cell Tumor", *N. Engl. J. Med.* 2015 Jul. 30; 373(5):428-37. Derivatives of CSF1R can be prepared based upon available CSF1R structures.

In embodiments, the present chimeric proteins may comprise a variant extracellular domain of CSF1R in which the signal peptide (e.g., as provided in SEQ ID NO: 1) is replaced with an alternative signal peptide. In embodiments, the present chimeric protein may comprise a variant extracellular domain of CSF1R which is expressed from a cDNA that has been codon-optimized for expression in protein producing cells such as Chinese Hamster Ovary (CHO) or human embryonic kidney (HEK) cells.

In embodiments, an extracellular domain of CSF1R refers to a portion of the protein which is capable of interacting with the extracellular environment. In embodiments, the extracellular domain of CSF1R is the entire amino acid sequence of the protein which is external of a cell or the cell membrane. In embodiments, the extracellular domain of CSF1R is a portion of an amino acid sequence of the protein which is external of a cell or the cell membrane and is needed for signal transduction and/or ligand binding as may be assayed using methods known in the art (e.g., in vitro ligand binding and/or cellular activation assays).

In embodiments, the extracellular domain of CSF1R refers to a portion of the protein which is capable for binding to colony stimulating factor 1 (CSF1). In embodiments, the chimeric protein binds to human CSF1 with a $K_D$ of less than about 1 µM, about 900 nM, about 800 nM, about 700 nM, about 600 nM, about 500 nM, about 400 nM, about 300 nM, about 200 nM, about 150 nM, about 130 nM, about 100 nM, about 90 nM, about 80 nM, about 70 nM, about 60 nM, about 55 nM, about 50 nM, about 45 nM, about 40 nM, about 35 nM, about 30 nM, about 25 nM, about 20 nM, about 15 nM, about 10 nM, or about 5 nM, or about 1 nM (as measured, for example, by surface plasmon resonance or biolayer interferometry). In embodiments, the chimeric protein binds to human CSF1 with a $K_D$ of less than about 1 nM, about 900 pM, about 800 pM, about 700 pM, about 600 pM, about 500 pM, about 400 pM, about 300 pM, about 200 pM, about 100 pM, about 90 pM, about 80 pM, about 70 pM, about 60 pM about 55 pM about 50 pM about 45 pM, about 40 pM, about 35 pM, about 30 pM, about 25 pM, about 20 pM, about 15 pM, or about 10 pM, or about 1 pM (as measured, for example, by surface plasmon resonance or biolayer interferometry).

In embodiments, the extracellular domain of CSF1R refers to a portion of the protein which is capable for binding to IL-34. In embodiments, the chimeric protein binds to human IL-34 with a $K_D$ of less than about 1 µM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 55 nM, about 50 nM, about 45 nM, about 40 nM, about 35 nM, about 30 nM, about 25 nM, about 20 nM, about 15 nM, about 10 nM, or about 5 nM, or about 1 nM (as measured, for example, by surface plasmon resonance or biolayer interferometry). In embodiments, the chimeric protein binds to IL-34 with a $K_D$ of less than about 1 nM, about 900 pM, about 800 pM, about 700 pM, about 600 pM, about 500 pM, about 400 pM, about 300 pM, about 200 pM, about 100 pM, about 90 pM, about 80 pM, about 70 pM, about 60 pM about 55 pM about 50 pM about 45 pM, about 40 pM, about 35 pM, about 30 pM, about 25 pM, about 20 pM, about 15 pM, or about 10 pM, or about 1 pM (as measured, for example, by surface plasmon resonance or biolayer interferometry). In embodiments, the chimeric protein binds to human CSF1 with a $K_D$ of from about 100 pM to about 600 pM.

The present chimeric protein further comprises a domain, e.g., the extracellular domain, of the immune stimulatory molecule CD40 ligand (CD40L, also known as CD154). CD40L is a type II transmembrane protein belonging to the Tumor Necrosis Factor (TNF) superfamily. CD40L binds to the CD40 receptor on macrophages and antigen-presenting cells (APC) including antigen-presenting B cells, which leads to many effects depending on the target cell type. CD40L has also been shown to bind the integrins α5β1 and αIIbβ3. CD40L acts as a costimulatory molecule and is particularly important on a subset of T cells called T follicular helper cells (TFH cells). On TFH cells, CD40L promotes B cell maturation and function by engaging CD40 on the B cell surface and therefore facilitating cell-cell communication.

In embodiments, the present chimeric protein comprises a domain, e.g., the extracellular domain, of human CD40L. The human CD40L comprises the amino acid sequence of SEQ ID NO: 3 (with the amino acid sequence of the extracellular domain comprising amino acids 47 to 261). In embodiments, the present chimeric protein comprises the extracellular domain of human CD40L which has the amino acid sequence of SEQ ID NO: 4. In embodiments, the present chimeric proteins may comprise the extracellular domain of CD40L as described herein, or a variant or functional fragment thereof. For instance, the chimeric protein may comprise a sequence of the extracellular domain of CD40L as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the extracellular domain of CD40L as described herein.

CD40L derivatives can be constructed from available structural data, including that described by Oganesyan V., et al., "Fibronectin type III domains engineered to bind CD40L: cloning, expression, purification, crystallization and preliminary X-ray diffraction analysis of two complexes", *Acta Crystallogr Sect F Struct Biol Cryst Commun.* 2013 September; 69(Pt 9):1045-8.

In embodiments, the present chimeric proteins may comprise a variant extracellular domain of CD40L in which the signal peptide (e.g., as provided in SEQ ID NO: 3) is replaced with an alternative signal peptide. In embodiments, the present chimeric protein may comprise a variant extracellular domain of CD40L which is expressed from a cDNA that has been codon-optimized for expression in protein producing cells such as Chinese Hamster Ovary (CHO) or HEK cells.

In embodiments, the extracellular domain of CD40L refers to a portion of protein which is capable of interacting with the extracellular environment. In embodiments, the extracellular domain of CD40L is the entire amino acid sequence of the protein which is external of a cell or the cell membrane. In embodiments, the extracellular domain of CD40L is a portion of an amino acid sequence of the protein which is external of a cell or the cell membrane and is needed for signal transduction and/or ligand binding as may be assayed using methods know in the art.

In embodiments, the extracellular domain of CD40L refers to a portion of the protein which is capable for binding to the CD40 receptor. Similar to other TNF superfamily members, membrane-bound CD40L exists as a homotrimer. CD40L binds to CD40, a member of the TNF receptor superfamily that is expressed predominantly on antigen presenting cells, including dendritic cells (DCs), B cells and macrophages. The CD40L/CD40 interactions exert profound effects on dendritic cells, B cells, and endothelial cells, among many cells of the hematopoietic and non-hematopoietic compartments. For example, CD40 signaling induces DCs to mature and effectively trigger T-cell activation and differentiation. CD40 signaling of B cells promotes germinal center (GC) formation, immunoglobulin (Ig) isotype switching, somatic hypermutation (SHM) of the Ig to enhance affinity for antigen, and the formation of long-lived plasma cells and memory B cells. CD40 signaling is also critical for immune cell survival.

In embodiments, the chimeric protein of the invention binds to human CD40 with a $K_D$ of less than about 1 µM, about 900 nM, about 800 nM, about 700 nM, about 600 nM, about 550 nM, about 530 nM, about 500 nM, about 400 nM, about 300 nM, about 200 nM, about 100 nM, about 90 nM, about 80 nM, about 70 nM, about 60 nM, about 55 nM, about 50 nM, about 45 nM, about 40 nM, about 35 nM, about 30 nM, about 25 nM, about 20 nM, about 15 nM, about 10 nM, or about 5 nM, or about 1 nM (as measured, for example, by surface plasmon resonance or biolayer interferometry). In embodiments, the chimeric protein binds to human CD40 with a $K_D$ of less than about 1 nM, about 900 pM, about 800 pM, about 700 pM, about 600 pM, about 500 pM, about 400 pM, about 300 pM, about 200 pM, about 100 pM, about 90 pM, about 80 pM, about 70 pM, about 60 pM about 55 pM about 50 pM about 45 pM, about 40 pM, about 35 pM, about 30 pM, about 25 pM, about 20 pM, about 15 pM, or about 10 pM, or about 1 pM (as measured, for example, by surface plasmon resonance or biolayer interferometry). In embodiments, the chimeric protein binds to human CD40 with a $K_D$ of from about 300 pM to about 700 pM.

In embodiments, the chimeric protein of the present invention comprises an extracellular domain of CSF1R (SEQ ID NO: 2).

In embodiments, the chimeric protein of the present invention comprises an extracellular domain of CD40L (SEQ ID NO: 4).

In embodiments, the chimeric protein of the present invention comprises an extracellular domain of OX40L (SEQ ID NO: 7).

In embodiments, the chimeric protein of the present invention comprises an extracellular domain of CSF1R (SEQ ID NO: 2) and the extracellular domain of CD40L (SEQ ID NO: 4).

In embodiments, the chimeric protein of the present invention comprises an extracellular domain of CSF1R (SEQ ID NO: 2) and the extracellular domain of OX40L (SEQ ID NO: 7).

In embodiments, the chimeric protein of the present invention comprises the hinge-CH2-CH3 domain from a human IgG4 antibody sequence (SEQ ID NO: 25, SEQ ID NO: 26, or SEQ ID NO: 27).

In embodiments, a chimeric protein comprises a modular linker as shown in FIG. 20.

In embodiments, the chimeric protein of the present invention comprises an extracellular domain of CSF1R and the extracellular domain of CD40L, using the hinge-CH2-CH3 domain from a human IgG4 antibody sequence as a linker (this CSF1R-Fc-CD40L chimera is SEQ ID NO: 5).

In embodiments, the chimeric protein of the present invention comprises an extracellular domain of CSF1R and the extracellular domain of OX40L, using the hinge-CH2-CH3 domain from a human IgG4 antibody sequence as a linker (this CSF1R-Fc-OX40L chimera is SEQ ID NO: 8).

In embodiments, the chimeric protein of the present invention comprises SEQ ID NO: 5, i.e., monomeric CSF1R-Fc-CD40L chimeric protein (SL-115154), or a variant or functional fragment thereof.

In embodiments, the chimeric protein may have at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of any one of SEQ ID NO: 5 or 8.

In embodiments, the chimeric proteins of the invention may comprise a sequence which has one or more amino acid mutations with respect to any one of the sequences disclosed herein. In embodiments, the chimeric protein comprises a sequence that has about 1, 2, 3, 4, 5, 6, 7, 8, 9, 10, 15, 20, 25, 30, 35, 40, 45, 50, 55, 60, 65, 70, 75, 80, 85, 90, 95, or 100 or more amino acid mutations with respect to any one of the amino acid sequences of chimeric proteins disclosed herein.

In embodiments, the one or more amino acid mutations may be independently selected from substitutions, insertions, deletions, and truncations.

In embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid with another amino acid listed within the same group of the six standard amino acid groups shown above. For example, the exchange of Asp by Glu retains one negative charge in the so-modified polypeptide. In addition, glycine and proline may be substituted for one another based on their ability to disrupt α-helices.

As used herein, "non-conservative substitutions" are defined as exchanges of an amino acid with another amino acid listed in a different group of the six standard amino acid groups (1) to (6) shown above.

In embodiments, the substitutions may also include non-classical amino acids (e.g., selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the chimeric proteins by reference to the genetic code, including taking into account codon degeneracy.

In embodiments, the chimeric protein comprises a linker. In embodiments, the linker comprising at least one cysteine residue capable of forming a disulfide bond. As described elsewhere herein, such at least one cysteine residue capable of forming a disulfide bond is, without wishing to be bound by theory, responsible for maintain a proper multimeric state of the chimeric protein and allowing for efficient production.

In embodiments, the chimeric protein of the present invention comprises (a) a first domain comprising a portion of colony stimulating factor 1 receptor (CSF1R), e.g., the extracellular domain of CSF1R, that is capable of binding a CSF1R ligand; (b) a second domain comprising a portion of CD40 Ligand (CD40L), e.g., the extracellular domain of CD40L, that is capable of binding a CD40L receptor; and (c) a linker linking the first domain and the second domain.

In embodiments, chimeric protein is a recombinant fusion protein, e.g., a single polypeptide having the extracellular domains described herein (and, optionally a linker). For example, in embodiments, the chimeric protein is translated as a single unit in a cell. In embodiments, a chimeric protein refers to a recombinant protein of multiple polypeptides, e.g. multiple extracellular domains described herein, that are linked to yield a single unit, e.g. in vitro (e.g. with one or more synthetic linkers described herein). In embodiments, the chimeric protein is chemically synthesized as one polypeptide or each domain may be chemically synthesized separately and then combined. In embodiments, a portion of the chimeric protein is translated and a portion is chemically synthesized.

In embodiments, the present chimeric proteins may be variants described herein, for instance, the present chimeric proteins may have a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the present chimeric proteins, e.g. one or more of SEQ IDs Nos 5 and 8.

In embodiments, the chimeric protein comprises a linker. In embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In embodiments, the linker may be designed using linker designing databases and computer programs such as those described in Chen et al, (2013), Adv Drug Deliv Rev. 65(10):1357-1369 and Crasto et. al., (2000), Protein Eng. 13(5):309-312, the entire contents of which are hereby incorporated by reference.

In embodiments, the linker is a synthetic linker such as PEG.

In embodiments, the linker comprises a polypeptide. In embodiments, the polypeptide is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In embodiments, the linker is flexible. In an embodiment, the linker is rigid.

In embodiments, the linker is substantially comprised of glycine and serine residues (e.g., about 30%, or about 40%, or about 50%, or about 60%, or about 70%, or about 80%, or about 90%, or about 95%, or about 97%, or about 98%, or about 99%, or about 100% glycines and serines).

In embodiments, the linker comprises a hinge region of an antibody (e.g., of IgG, IgA, IgD, and IgE, inclusive of subclasses (e.g., IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al, 1992 Immunological Reviews 130:87. The upper hinge region includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence CPPC (SEQ ID NO: 48) which, when dimerized by disulfide bond formation, results in a cyclic octapeptide believed to act as a pivot, thus conferring flexibility. In embodiments, the present linker comprises, one, or two, or three of the upper hinge region, the core region, and the lower hinge region of any antibody (e.g., of IgG, IgA, IgD, and IgE, inclusive of subclasses (e.g., IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In embodiments, the linker of the present invention comprises one or more glycosylation sites.

In embodiments, the linker comprises an Fc domain of an antibody (e.g., of IgG, IgA, IgD, and IgE, inclusive of subclasses (e.g., IgG1, IgG2, IgG3, and IgG4, and IgA1 and IgA2)). In embodiments, the linker comprises a hinge-CH2-CH3 Fc domain derived from a human IgG4 antibody. In embodiments, the linker comprises a hinge-CH2-CH3 Fc domain derived from a human IgG1 antibody. In embodiments, the Fc domain exhibits increased affinity for and enhanced binding to the neonatal Fc receptor (FcRn). In embodiments, the Fc domain includes one or more mutations that increases the affinity and enhances binding to FcRn. Without wishing to be bound by theory, it is believed that increased affinity and enhanced binding to FcRn increases the in vivo half-life of the present chimeric proteins.

In embodiments, the Fc domain in a linker contains one or more amino acid substitutions at amino acid residue 250, 252, 254, 256, 308, 309, 311, 416, 428, 433 or 434 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference), or equivalents thereof. In embodiments, the amino acid substitution at amino acid residue 250 is a substitution with glutamine. In embodiments, the amino acid substitution at amino acid residue 252 is a substitution with tyrosine, phenylalanine, tryptophan or threonine. In embodiments, the amino acid substitution at amino acid residue 254 is a substitution with threonine. In embodiments, the amino acid substitution at amino acid residue 256 is a substitution with serine, arginine, glutamine, glutamic acid, aspartic acid, or threonine. In embodiments, the amino acid substitution at amino acid residue 308 is a substitution with threonine. In embodiments, the amino acid substitution at amino acid residue 309 is a substitution with proline. In embodiments, the amino acid substitution at amino acid residue 311 is a substitution with serine. In embodiments, the amino acid substitution at amino acid residue 385 is a substitution with arginine, aspartic acid, serine, threonine, histidine, lysine, alanine or glycine. In embodiments, the amino acid substitution at amino acid residue 386 is a substitution with threonine, proline, aspartic acid, serine, lysine, arginine, isoleucine, or methionine. In embodiments, the amino acid substitution at amino acid residue 387 is a substitution with arginine, proline, histidine, serine, threonine, or alanine. In embodiments, the amino acid substitution at amino acid residue 389 is a substitution with proline, serine or asparagine. In embodiments, the amino acid substitution at amino acid residue 416 is a substitution with serine. In embodiments, the amino acid substitution at amino acid residue 428 is a substitution with leucine. In embodiments, the amino acid substitution at amino acid residue 433 is a substitution with arginine, serine, isoleucine, proline, or glutamine. In embodiments, the amino acid substitution at amino acid residue 434 is a substitution with histidine, phenylalanine, or tyrosine.

In embodiments, the Fc domain in a linker (e.g., comprising an IgG constant region) comprises one or more mutations such as substitutions at amino acid residue 252, 254, 256, 433, 434, or 436 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). In embodiments, the IgG constant region includes a triple M252Y/S254T/T256E mutation or YTE mutation. In an embodiment, the IgG constant region includes a triple H433K/N434F/Y436H mutation or KFH mutation. In embodiments, the IgG constant region includes an YTE and KFH mutation in combination.

In embodiments, the modified humanized antibodies of the invention comprise an IgG constant region that contains one or more mutations at amino acid residues 250, 253, 307, 310, 380, 428, 433, 434, and 435 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). Illustrative mutations include T250Q, M428L, I307A, E380A, I253A, H310A, M428L, H433K, N434A, N434F, N434S, and H435A. In embodiments, the IgG constant region comprises a M428L/N434S mutation or LS mutation. In an embodiment, the IgG constant region comprises a T250Q/M428L mutation or QL mutation. In an embodiment, the IgG constant region comprises an N434A mutation. In an embodiment, the IgG constant region comprises a T307A/E380A/N434A mutation or AAA mutation. In an embodiment, the IgG constant region comprises an I253A/H310A/H435A mutation or IHH mutation. In an embodiment, the IgG constant region comprises a H433K/N434F mutation. In an embodiment, the IgG constant region comprises a M252Y/S254T/T256E and a H433K/N434F mutation in combination.

Additional exemplary mutations in the IgG constant region are described, for example, in Robbie, et al., Antimicrobial Agents and Chemotherapy (2013), 57(12):6147-6153, Dall'Acqua et al., JBC (2006), 281(33):23514-24, Dall'Acqua et al, Journal of Immunology (2002), 169:5171-80, Ko et al. Nature (2014) 514:642-645, Grevys et al. Journal of Immunology. (2015), 194(11):5497-508, and U.S. Pat. No. 7,083,784, the entire contents of which are hereby incorporated by reference.

In embodiments, the Fc domain in a linker has the amino acid sequence of SEQ ID NO: 25 (see the below table), or at least 90%, or 93%, or 95%, or 97%, or 98%, or 99% identity thereto. In embodiments, mutations are made to SEQ ID NO: 25 to increase stability and/or half-life. For instance, in embodiments, the Fc domain in a linker comprises the amino acid sequence of SEQ ID NO: 26 (see the below table), or at least 90%, or 93%, or 95%, or 97%, or 98%, or 99% identity thereto. An illustrative Fc stabilizing mutant is S228P. Illustrative Fc half-life extending mutants are T250Q, M428L, V308T, L309P, and Q311S and the present linkers may comprise 1, or 2, or 3, or 4, or 5 of these mutants. For instance, in embodiments, the Fc domain in a linker comprises the amino acid sequence of SEQ ID NO: 27 (see the below table), or at least 90%, or 93%, or 95%, or 97%, or 98%, or 99% identity thereto.

Further, one or more joining linkers may be employed to connect an Fc domain in a linker (e.g., one of SEQ ID NO:

25, SEQ ID NO: 26, SEQ ID NO: 27, or at least 90%, or 93%, or 95%, or 97%, or 98%, or 99% identity thereto) and the extracellular domains. For example, any one of SEQ ID NO: 28, SEQ ID NO: 29, SEQ ID NO: 30, SEQ ID NO: 31, SEQ ID NO: 32, SEQ ID NO: 33, or variants thereof may connect an extracellular domain (ECD) as described herein and an Fc domain in a linker as described herein. Optionally, any one of SEQ ID NOs: 28 to 74, or variants thereof are located between an extracellular domain as described herein and an Fc domain as described herein. In embodiments, a chimeric protein comprises one joining linker preceding an Fc domain and a second joining linker following the Fc domain; thus, a chimeric protein may comprise the following structure:

ECD 1 (e.g., CSF1R)—Joining Linker 1—Fc Domain—Joining Linker 2—ECD 2 (e.g., CD40L).

In embodiments, the first and second joining linkers may be different or they may be the same.

In embodiments, the first and second joining linkers may be selected from the amino acid sequences of SEQ ID NOs: 25 to 74 and are provided in Table 1 below:

TABLE 1

Illustrative linkers (Fc domain linkers and joining linkers)

| SEQ ID NO. | Sequence |
|---|---|
| 25 | APEFLGGPSVFLFPPKPKDTLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVMHEALHNHYTQKSLSLSLGK |
| 26 | APEFLGGPSVFLFPPKPKDQLMISRTPEVTCVVVDVSQEDPEVQFNWYVDGVEVHNAKTKPREEQFNSTYRVVSVLTTPHSDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSSWQEGNVFSCSVLHEALHNHYTQKSLSLSLGK |
| 27 | APEFLGGPSVFLFPPKPKDQLMISRTPEVTCVVVDVSQEDPEVQFNWYVDGVEVHNAKTKPREEQFNSTYRVVSVLTVLHQDWLSGKEYKCKVSSKGLPSSIEKTISNATGQPREPQVYTLPPSQEEMTKNQVSLTCLVKGFYPSDIAVEWESNGQPENNYKTTPPVLDSDGSFFLYSRLTVDKSRWQEGNVFSCSVLHEALHNHYTQKSLSLSLGK |
| 28 | SKYGPPCPSCP |
| 29 | SKYGPPCPPCP |
| 30 | SKYGPP |
| 31 | IEGRMD |
| 32 | GGGVPRDCG |
| 33 | IEGRMDGGGGAGGGG |
| 34 | GGGSGGGS |
| 35 | GGGSGGGSGGG |
| 36 | EGKSSGSGSESKST |
| 37 | GGSG |
| 38 | GGSGGGSGGGSG |
| 39 | EAAAKEAAAKEAAAK |
| 40 | EAAAREAAAREAAAREAAAR |
| 41 | GGGGSGGGGSGGGGSAS |
| 42 | GGGGAGGGG |
| 43 | GS or GGS or LE |
| 44 | GSGSGS |
| 45 | GSGSGSGSGS |
| 46 | GGGGSAS |
| 47 | APAPAPAPAPAPAPAPAP |
| 48 | CPPC |
| 49 | GGGGS |
| 50 | GGGGSGGGGS |
| 51 | GGGGSGGGGSGGGGS |
| 52 | GGGGSGGGGSGGGGSGGGGS |
| 53 | GGGGSGGGGSGGGGSGGGGSGGGGS |
| 54 | GGGGSGGGGSGGGGSGGGGSGGGGSGGGGS |
| 55 | GGGGSGGGGSGGGGSGGGGSGGGGSGGGGSGGGGS |
| 56 | GGGGSGGGGSGGGGSGGGGSGGGGSGGGGSGGGGSGGGGS |
| 57 | GGSGGSGGGGSGGGGS |
| 58 | GGGGGGGG |
| 59 | GGGGGG |
| 60 | EAAAK |
| 61 | EAAAKEAAAK |
| 62 | EAAAKEAAAKEAAAK |
| 63 | AEAAAKEAAAKA |
| 64 | AEAAAKEAAAKEAAAKA |
| 65 | AEAAAKEAAAKEAAAKEAAAKA |
| 66 | AEAAAKEAAAKEAAAKEAAAKEAAAKA |
| 67 | AEAAAKEAAAKEAAAKEAAAKALEAEAAAKEAAAKEAAAKEAAAKA |
| 68 | PAPAP |
| 69 | KESGSVSSEQLAQFRSLD |
| 70 | GSAGSAAGSGEF |
| 71 | GGGSE |
| 72 | GSESG |
| 73 | GSEGS |
| 74 | GEGGSGEGSSGEGSSSEGGGSEGGGSEGGGSEGGS |

In embodiments, the joining linker substantially comprises glycine and serine residues (e.g., about 30%, or about 40%, or about 50%, or about 60%, or about 70%, or about 80%, or about 90%, or about 95%, or about 97%, or about 98%, or about 99%, or about 100% glycines and serines). For example, in embodiments, the joining linker is (Gly$_4$Ser)$_n$, where n is from about 1 to about 8, e.g., 1, 2, 3, 4, 5, 6, 7, or 8 (SEQ ID NO: 49 to SEQ ID NO: 56, respectively). In embodiments, the joining linker sequence is GGSGGSGGGGSGGGS (SEQ ID NO: 57). Additional illustrative joining linkers include, but are not limited to, linkers having the sequence LE, (Gly)$_8$ (SEQ ID NO: 58), (Gly)$_6$ (SEQ ID NO: 59), (EAAAK)$_n$, (n=1-3) (SEQ ID NO: 60—SEQ ID NO: 62), A(EAAAK)$_n$A (n=2-5) (SEQ ID NO: 63—SEQ ID NO: 66), A(EAAAK)$_4$ALEA(EAAAK)$_4$A (SEQ ID NO: 67), PAPAP (SEQ ID NO: 68), KESGSVSSE-QLAQFRSLD (SEQ ID NO: 69), GSAGSAAGSGEF (SEQ ID NO: 70), and (XP)$_n$, with X designating any amino acid, e.g., Ala, Lys, or Glu. In embodiments, the joining linker is GGS.

In embodiments, the joining linker is one or more of GGGSE (SEQ ID NO: 71), GSESG (SEQ ID NO: 72), GSEGS (SEQ ID NO: 73), GEGGSGEGSSGEGSSSEGGGSEGGGSEGGGSEGGS (SEQ ID NO: 74), and a joining linker of randomly placed G, S, and E every 4 amino acid intervals.

In embodiments, a chimeric protein comprises a modular linker as shown in FIG. 20.

In embodiments, the linker may be functional. For example, without limitation, the linker may function to improve the folding and/or stability, improve the expression, improve the pharmacokinetics, and/or improve the bioactivity of the present chimeric protein. In another example, the linker may function to target the chimeric protein to a particular cell type or location.

In embodiments, the chimeric protein exhibits enhanced stability and protein half-life. In embodiments, the chimeric protein binds to FcRn with high affinity. In embodiments, the chimeric protein may bind to FcRn with a K$_D$ of about 1 nM to about 80 nM. For example, the chimeric protein may bind to FcRn with a K$_D$ of about 1 nM, about 2 nM, about 3 nM, about 4 nM, about 5 nM, about 6 nM, about 7 nM, about 8 nM, about 9 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 71 nM, about 72 nM, about 73 nM, about 74 nM, about 75 nM, about 76 nM, about 77 nM, about 78 nM, about 79 nM, or about 80 nM. In embodiments, the chimeric protein may bind to FcRn with a K$_D$ of about 9 nM. In embodiments, the chimeric protein does not substantially bind to other Fc receptors (i.e., other than FcRn) with effector function.

In embodiments, a chimeric protein having the formula ECD 1—Joining Linker 1—Fc Domain—Joining Linker 2—ECD 2, in which ECD 1 is CSF1R and ECD 2 is CD40L may be referred to in the present disclosure as CSF1R-Fc-CD40L. In embodiments, the chimeric protein lacks one or both joining linkers; such a chimeric protein may also be referred to in the present disclosure as CSF1R-Fc-CD40L.

In embodiments, a chimeric protein is a fusion protein having the formula N terminus-(a)-(b)-(c)-C terminus, in which (a) is CSF1R, (b) is a linker comprising at least a portion of a Fc domain, and (c) is CD40L may be referred to in the present disclosure as CSF1R-Fc-CD40L.

In embodiments, a chimeric protein is optimized for/directed to murine ligands/receptors; an example of such a chimeric protein is murine CSF1R-Fc-CD40L, which is also referred herein as mCSF1R-Fc-CD40L.

In embodiments, a chimeric protein is optimized for/directed to human ligands/receptors; an example of such a chimeric protein is human CSF1R-Fc-CD40L, which is also referred herein as hCSF1R-Fc-CD40L.

These chimeric proteins may lack one or both of the joining linkers. Exemplary Joining Linker 1s, Fc Domains, and Joining Linker 2s are described above in Table 1; modular linkers useful for forming chimeric proteins and comprising specific Joining Linker 1s, Fc Domains, and Joining Linker 2s are shown in FIG. 20. In embodiments, the present chimeric protein is engineered to target the CSF1R/CSF1 immune inhibitory signaling pathway. In embodiment, the chimeric protein is engineered to disrupt, block, reduce, and/or inhibit the transmission of an immune inhibitory signal mediated by binding of CSF1 to CSF1R. In embodiments, an immune inhibitory signal refers to a signal that diminishes or eliminates an immune response. For example, in the context of oncology, such signals may diminish or eliminate antitumor immunity. Under normal physiological conditions, inhibitory signals are useful in the maintenance of self-tolerance (e.g., prevention of autoimmunity) and also to protect tissues from damage when the immune system is responding to pathogenic infection. For instance, without limitation, an immune inhibitory signal may be identified by detecting an increase in cellular proliferation, cytokine production, cell killing activity or phagocytic activity when such an inhibitory signal is blocked.

In embodiments, the present chimeric protein disrupts, blocks, reduces, and/or inhibits the transmission of an immune inhibitory signal mediated by the binding of CSF1 or IL-34 to CSF1R. In embodiments, the chimeric protein binds to and sequesters CSF1 or IL-34, and thereby disrupts, blocks, reduces, and/or inhibits the inhibitory signal transmission to an immune cell (e.g., a tumor-associated macrophage, antigen presenting cell, myeloid cell, or a T cell).

In embodiments, the present chimeric proteins are capable of, or find use in methods comprising, inhibiting or reducing the binding of the immune inhibitory receptor/ligand pair: CSF1R/CSF1 or CSF1R/IL-34. In embodiments, the present chimeric protein blocks, reduces, and/or inhibits CSF1R activation, for example, by reducing the binding of CSF1R on immune cells with CSF1 or IL-34.

In embodiments, the present chimeric protein targets an immune stimulatory signal mediated by the binding of CD40L to CD40. In embodiment, the chimeric protein is engineered to enhance, increase, and/or stimulate the transmission of an immune stimulatory signal mediated by binding of CD40L to CD40. In embodiments, an immune stimulatory signal refers to a signal that enhances an immune response. For example, in the context of oncology, such signals may enhance antitumor immunity. For instance, without limitation, immune stimulatory signal may be identified by directly stimulating proliferation, cytokine production, killing activity or phagocytic activity of leukocytes, including subsets of T cells.

In embodiments, the present chimeric protein enhances, increases, and/or stimulates the transmission of an immune stimulatory signal mediated by the binding of CD40L to CD40. In embodiments, the present chimeric protein comprising the extracellular domain of CD40L acts on an immune cell (e.g., a dendritic cell, a B cell, a macrophage, an antigen presenting cell, or a T cell) that expresses CD40 and enhances, increases, and/or stimulates stimulatory signal transmission to the immune cell (e.g., a dendritic cell, a B cell, a macrophage, and a T cell).

In embodiments, the present chimeric proteins are capable of, or find use in methods comprising, stimulating or enhancing the binding of the immune stimulatory receptor/ligand pair: CD40:CD40L. In embodiments, the present chimeric protein increases and/or stimulates CD40 and/or the binding of CD40 with one or more of CD40L.

In embodiments, a chimeric protein comprises an extracellular domain of type II protein, other than CD40L. Exemplary type II proteins include 4-1BBL, CD30L, FasL, GITRL, LIGHT, OX40L, TL1A, and TRAIL. The present invention further includes chimeric proteins and methods using the following chimeric proteins: CSF1R/4-1BBL, CSF1R/CD30L, CSF1R/FasL, CSF1R/GITRL, CSF1R/LIGHT, CSF1R/OX40L, CSF1R/TL1A, and CSF1R/TRAIL. In embodiments, the chimeric protein has a general structure of one of CSF1R-Fc-4-1BBL, CSF1R-Fc-CD30L, CSF1R-Fc-FasL, CSF1R-Fc-GITRL, CSF1R-Fc-LIGHT, CSF1R-Fc-OX40L, CSF1R-Fc-TL1A, and CSF1R-Fc-TRAIL.

The amino acid sequence for 4-1BBL, CD30L, FasL, GITRL, LIGHT, OX40L, TL1A, and TRAIL, respectively, comprises SEQ ID NO: 9, 11, 13, 15, 17, 6, 21, and 23.

In embodiments, a chimeric protein comprises the extracellular domain of one of 4-1BBL, CD30L, FasL, GITRL, LIGHT, OX40L, TL1A, and TRAIL which, respectively, comprises SEQ ID NO: 10, 12, 14, 16, 18, 7, 22, and 24. In embodiments, the present chimeric proteins may comprise the extracellular domain of 4-1BBL, CD30L, FasL, GITRL, LIGHT, OX40L, TL1A, or TRAIL as described herein, or a variant or a functional fragment thereof. For instance, the chimeric protein may comprise a sequence of the extracellular domain of 4-1BBL, CD30L, FasL, GITRL, LIGHT, OX40L, TL1A, or TRAIL as provided above, or a variant or functional fragment thereof having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99% sequence identity with the amino acid sequence of the extracellular domain of 4-1BBL, CD30L, FasL, GITRL, LIGHT, OX40L, TL1A, or TRAIL as described herein.

In embodiments, the chimeric protein of the invention delivers an immune stimulation to an immune cell (e.g., an antigen presenting cell) while providing a localized trap or sequester of immune inhibitory signals. In embodiments, the chimeric protein delivers signals that have the net result of immune activation.

In embodiments, the present chimeric proteins are capable of, and can be used in methods comprising, promoting immune activation (e.g., against tumors). In embodiments, the present chimeric proteins are capable of, and can be used in methods comprising, suppressing immune inhibition (e.g., that allows tumors to survive). In embodiments, the present chimeric proteins provide improved immune activation and/or improved suppression of immune inhibition due to the proximity of signaling that is provided by the chimeric nature of the constructs.

In embodiments, the present chimeric proteins are capable of, or can be used in methods comprising, modulating the amplitude of an immune response, e.g., modulating the level of effector output. In embodiments, e.g., when used for the treatment of a cancer and/or an inflammatory disease, the present chimeric proteins alter the extent of immune stimulation as compared to immune inhibition to increase the amplitude of a T cell response, including, without limitation, stimulating increased levels of cytokine production, proliferation or target killing potential.

In embodiments, the present chimeric proteins are capable of, or find use in methods involving, masking an inhibitory ligand on the surface of a tumor cell and replacing that immune inhibitory ligand with an immune stimulatory ligand. For example, the present chimeric protein comprises (a) an extracellular domain of CSF1R and (b) an extracellular domain of CD40L, allows for the disruption of an inhibitory CSF1/CSF1R signal and replacing it with a stimulating CD40L/CD40 signal. Accordingly, the present chimeric proteins, in embodiments are capable of, or find use in methods involving, reducing or eliminating an inhibitory immune signal and/or increasing or activating an immune stimulatory signal. For example, a tumor comprising an inhibitory signal (and thus evading an immune response) may be substituted for a positive signal binding on a macrophage or a T cell that can then attack a tumor cell. Accordingly, in embodiments, an inhibitory immune signal is masked by the present constructs and a stimulatory immune signal is activated. Such beneficial properties are enhanced by the single construct approach of the present chimeric proteins. For instance, the signal replacement can be effected nearly simultaneously, e.g., contemporaneously, and the signal replacement is tailored to be local at a site of clinical importance (e.g., the tumor microenvironment).

In embodiments, the present chimeric proteins are capable of, or find use in methods involving, enhancing, restoring, promoting and/or stimulating immune modulation. In embodiments, the present chimeric proteins described herein, restore, promote and/or stimulate the activity or activation of one or more immune cells against tumor cells including, but not limited to: T cells, cytotoxic T lymphocytes, T helper cells, natural killer (NK) cells, natural killer T (NKT) cells, anti-tumor macrophages (e.g., M1 macrophages), B cells, and dendritic cells. In embodiments, the present chimeric proteins enhance, restore, promote and/or stimulate the activity and/or activation of T cells, including, by way of a non-limiting example, activating and/or stimulating one or more T-cell intrinsic signals, including a pro-survival signal; an autocrine or paracrine growth signal; a p38 MAPK-, ERK-, STAT-, JAK-, AKT- or PI3K-mediated signal; an anti-apoptotic signal; and/or a signal promoting and/or necessary for one or more of: proinflammatory cytokine production or T cell migration or T cell tumor infiltration.

In embodiments, the present chimeric proteins are capable of, or find use in methods involving, causing an increase of one or more of T cells (including without limitation cytotoxic T lymphocytes, T helper cells, natural killer T (NKT) cells), B cells, natural killer (NK) cells, natural killer T (NKT) cells, dendritic cells, monocytes, and macrophages (e.g., one or more of M1 and M2) into a tumor or the tumor microenvironment. In embodiments, the chimeric protein enhances recognition of tumor antigens by CD8+ T cells, particularly those T cells that have infiltrated into the tumor microenvironment. In embodiments, the present chimeric protein induces CD19 expression and/or increases the number of CD19 positive cells (e.g., CD19 positive B cells). In an embodiment, the present chimeric protein induces IL-15Rα expression and/or increases the number of IL-15Rα positive cells (e.g., IL-15Rα positive dendritic cells).

In embodiments, the present chimeric proteins are capable of, or find use in methods involving, inhibiting and/or causing a decrease in immunosuppressive cells (e.g., myeloid-derived suppressor cells (MDSCs), regulatory T cells (Tregs), tumor associated neutrophils (TANs), M2 macrophages, and tumor associated macrophages (TAMs)), and particularly within the tumor and/or tumor microenvironment (TME). In embodiments, the present therapies may alter the ratio of M1 versus M2 macrophages in the tumor site and/or TME to favor M1 macrophages.

In embodiments, the present chimeric proteins are capable of, and can be used in methods comprising, inhibiting and/or reducing T cell inactivation and/or immune tolerance to a tumor, comprising administering an effective amount of a chimeric protein described herein to a subject. In embodiments, the present chimeric proteins are able to increase the serum levels of various cytokines including, but not limited to, one or more of IFNγ, TNFα, IL-2, IL-4, IL-5, IL-6, IL-9, IL-10, IL-13, IL-17A, IL-17F, and IL-22. In embodiments, the present chimeric proteins are capable of enhancing IL-2, IL-4, IL-5, IL-10, IL-13, IL-17A, IL-22, TNFα, or IFNγ in the serum of a treated subject. Detection of such a cytokine response may provide a method to determine the optimal dosing regimen for the indicated chimeric protein.

In embodiments, the present chimeric proteins inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion. Accordingly, a pro-tumor T cell refers to a state of T cell dysfunction that arises during many chronic infections, inflammatory diseases, and cancer. This dysfunction is defined by poor proliferative and/or effector functions, sustained expression of inhibitory receptors and a transcriptional state distinct from that of functional effector or memory T cells. Exhaustion prevents optimal control of infection and tumors. Illustrative pro-tumor T cells include, but are not limited to, Tregs, CD4+ and/or CD8+ T cells expressing one or more checkpoint inhibitory receptors, Th2 cells and Th17 cells. Checkpoint inhibitory receptors refer to receptors expressed on immune cells that prevent or inhibit uncontrolled immune responses. In contrast, an anti-tumor CD8+ and/or CD4+ T cell refers to T cells that can mount an immune response to a tumor.

In embodiments, the present chimeric proteins are capable of, and can be used in methods comprising, increasing a ratio of effector T cells to regulatory T cells. Illustrative effector T cells include ICOS+ effector T cells; cytotoxic T cells (e.g., αβ TCR, CD3+, CD8+, CD45RO+); CD4+ effector T cells (e.g., αβ TCR, CD3+, CD4+, CCR7+, CD62Lhi, IL-7R/CD127+); CD8+ effector T cells (e.g., αβ TCR, CD3+, CD8+, CCR7+, CD62Lhi, IL-7R/CD127+); effector memory T cells (e.g., CD62Llow, CD44+, TCR, CD3+, IL-7R/CD127+, IL-15R+, CCR7low); central memory T cells (e.g., CCR7+, CD62L+, CD27'; or CCR7hi, CD44+, CD62Lhi, TCR, CD3+, IL-7R/CD127+, IL-15R+); CD62L+ effector T cells; CD8+ effector memory T cells (TEM) including early effector memory T cells (CD27+ CD62L−) and late effector memory T cells (CD27− CD62L−) (TemE and TemL, respectively); CD127(+)CD25(low/−) effector T cells; CD127(−)CD25(−) effector T cells; CD8+ stem cell memory effector cells (TSCM) (e.g., CD44(low)CD62L(high)CD122(high) sca(+)); TH1 effector T-cells (e.g., CXCR3+, CXCR6+ and CCR5+; or αβ TCR, CD3+, CD4+, IL-12R+, IFNγR+, CXCR3+), TH2 effector T cells (e.g., CCR3+, CCR4+ and CCR8+; or αβ TCR, CD3+, CD4+, IL-4R+, IL-33R+, CCR4+, IL-17RB+, CRTH2+); TH9 effector T cells (e.g., αβ TCR, CD3+, CD4+); TH17 effector T cells (e.g., αβ TCR, CD3+, CD4+, IL-23R+, CCR6+, IL-1R+); CD4+ CD45RO+ CCR7+ effector T cells, CD4+ CD45RO+CCR7(−) effector T cells; and effector T cells secreting IL-2, IL-4 and/or IFN-γ. Illustrative regulatory T cells include ICOS+ regulatory T cells, CD4+ CD25+ FOXP3+ regulatory T cells, CD4+ CD25+ regulatory T cells, CD4+ CD25− regulatory T cells, CD4+ CD25high regulatory T cells, TIM-3+PD-1+ regulatory T cells, lymphocyte activation gene-3 (LAG-3)+ regulatory T cells, CTLA-4/CD152" regulatory T cells, neuropilin-1 (Nrp-1)+ regulatory T cells, CCR4+CCR8+ regulatory T cells, CD62L (L-selectin)+ regulatory T cells, CD45RBlow regulatory T cells, CD127low regulatory T cells, LRRC32/GARP+ regulatory T cells, CD39+ regulatory T cells, GITR+ regulatory T cells, LAP+ regulatory T cells, 1611+ regulatory T cells, BTLA+ regulatory T cells, type 1 regulatory T cells (Tr1 cells), T helper type 3 (Th3) cells, regulatory cell of natural killer T cell phenotype (NKTregs), CD8+ regulatory T cells, CD8"CD28− regulatory T cells and/or regulatory T-cells secreting IL-10, IL-35, TGF-6, TNF-α, Galectin-1, IFN-γ and/or MCP1.

In embodiments, the chimeric protein of the invention causes an increase in effector T cells (e.g., CD4±CD25− T cells).

In embodiments, the chimeric protein causes a decrease in regulatory T cells (e.g., CD4+CD25+ T cells).

In embodiments, the chimeric protein generates a memory response which may, e.g., be capable of preventing relapse or protecting the animal from a rechallenge. Thus, an animal treated with the chimeric protein is later able to attack tumor cells and/or prevent development of tumors when rechallenged after an initial treatment with the chimeric protein. Accordingly, a chimeric protein of the present invention stimulates both active tumor destruction and also immune recognition of tumor antigens, which are essential in programming a memory response capable of preventing relapse.

In embodiments, the present chimeric proteins are capable of, and can be used in methods comprising, transiently stimulating effector immune cells for no longer than about 12 hours, about 24 hours, about 48 hours, about 72 hours or about 96 hours or about 1 week or about 2 weeks. In embodiments, the present chimeric proteins are capable of, and can be used in methods comprising, transiently depleting or inhibiting regulatory or immune suppressive cells for no longer than about 12 hours, about 24 hours, about 48 hours, about 72 hours or about 96 hours or about 1 week or about 2 weeks. In embodiments, the transient stimulation of effector T cells and/or transient depletion or inhibition of immune inhibitory cells occurs substantially in a patient's bloodstream or in a particular tissue/location including lymphoid tissues such as for example, the bone marrow, lymphnode, spleen, thymus, mucosa-associated lymphoid tissue (MALT), non-lymphoid tissues, or in the tumor microenvironment.

In embodiments, the present chimeric proteins provide advantages including, without limitation, ease of use and ease of production. This is because two distinct immunotherapy agents are combined into a single product which allows for a single manufacturing process instead of two independent manufacturing processes. In addition, administration of a single agent instead of two separate agents allows for easier administration and greater patient compliance.

In embodiments, the present chimeric protein is producible in a mammalian host cell as a secretable and fully functional single polypeptide chain.

In embodiments, the present chimeric protein unexpectedly provides binding of the extracellular domain components to their respective binding partners with slow off rates (Kd or $K_{off}$). In embodiments, this provides an unexpectedly long interaction of the receptor to ligand and vice versa. Such an effect allows for a sustained negative signal masking effect. Further, in embodiments, this delivers a longer positive signal effect, e.g., to allow an effector cell to be adequately stimulated for an anti-tumor effect. For example, the present chimeric protein, e.g., via the long off rate binding allows sufficient signal transmission to provide immune cell proliferation and allow for anti-tumor attack. By way of further example, the present chimeric protein, e.g., via the long off rate binding allows sufficient signal transmission to provide release of stimulatory signals, such as, for example, cytokines.

The stable synapse of cells promoted by the present agents (e.g. a tumor cell bearing negative signals and a T cell which could attack the tumor) provides spatial orientation to favor tumor reduction—such as positioning the T cells to attack tumor cells and/or sterically preventing the tumor cell from delivering negative signals, including negative signals beyond those masked by the chimeric protein of the invention.

In embodiments, the present chimeric protein exhibits a Kd (1/s) for human CSF1 or IL-34 of more than about $2\times10^6$, about $2.5\times10^6$, about $3\times10^6$, about $3.5\times10^6$, about $4\times10^6$, about $4.5\times10^6$, about $5\times10^6$, about $5.5\times10^6$, about $6\times10^6$, about $6.5\times10^6$, about $7\times10^6$, about $7.5\times10^6$, about $8\times10^6$, about $8.5\times10^6$, about $9\times10^6$, or about $9.5\times10^6$ (as measured, for example, by surface plasmon resonance or biolayer interferometry). In embodiments, the chimeric protein binds to human CSF1 with a $K_D$ of from about 100 pM to about 600 pM. In embodiments, the chimeric protein binds to human CSF1 with a $K_a$ on rate (1/Ms) of about $5.7\times10^4$ and unbinds from human CSF1 with a $K_d$ on rate (1/s) of about $7.3\times10^{-6}$.

In embodiments, the present chimeric protein exhibits a Kd (1/s) for human CD40 of more than about $2\times10^6$, about $2.5\times10^6$, about $3\times10^6$, about $3.5\times10^6$, about $4\times10^6$, about $4.5\times10^6$, about $5\times10^6$, about $5.5\times10^6$, about $6\times10^6$, about $6.5\times10^6$, about $7\times10^6$, about $7.5\times10^6$, about $8\times10^6$, about $8.5\times10^6$, about $9\times10^6$, or about $9.5\times10^6$ (as measured, for example, by surface plasmon resonance or biolayer interferometry). In embodiments, the chimeric protein binds to human CD40 with a $K_a$ on rate (1/Ms) of about $1.3\times10^4$ and unbinds from human CD40 with a $K_d$ off rate (1/s) of about $6.7\times10^{-6}$.

In embodiments, this provides longer on-target (e.g., intra-tumoral) half-life (tire) as compared to serum t112 of the chimeric proteins. Such properties could have the combined advantage of reducing off-target toxicities associated with systemic distribution of the chimeric proteins.

Indeed, has been reported that sequential treatments with CSF1 blocking antibodies and CD40 agonist antibodies, for example, induce liver toxicity. See, e.g., Byrne et al. *J. Immunology*, 2016. Data disclosed herein (See, e.g., FIG. 13) similarly show that the two antibodies are highly toxic when co-administered to mice and cause lethal gut inflammation and diarrhea. In contrast and surprisingly, treatments with a CSF1R-Fc-CD40L chimeric protein blocks CSF1R (which inhibits the transmission of an immune inhibitory signal) and activates CD40 (which enhances, increases, and/or stimulates the transmission of an immune stimulatory signal), yet without the toxicity resulting from antibody co-treatments. Further, in embodiments, the present chimeric proteins provide synergistic therapeutic effects (e.g., anti-tumor effects) as it allows for improved site-specific interplay of two immunotherapy agents. In embodiments, the present chimeric proteins provide synergistic therapeutic effects when compared to CD40 agonist antibodies and/or CSF1R antagonistic antibodies. In embodiments, the present chimeric proteins provide the potential for reducing off-site and/or systemic toxicity.

In embodiments, the present chimeric protein exhibit enhanced safety profiles. In embodiment, the present chimeric protein exhibit reduced toxicity profiles. For example, administration of the present chimeric protein may result in reduced side effects such as one or more of diarrhea, inflammation (e.g., of the gut), or weight loss, which are observed with administration of CD40 agonist antibodies and/or CD115 antagonistic antibodies. In embodiments, the present chimeric protein provides improved safety, as compared to CD40 agonist antibodies and/or CD115 antagonistic antibodies, without sacrificing efficacy.

In embodiments, the present chimeric proteins provide reduced side-effects, e.g., GI complications, relative to current immunotherapies, e.g., antibodies directed to checkpoint molecules as described herein. Illustrative GI complications include abdominal pain, appetite loss, autoimmune effects, constipation, cramping, dehydration, diarrhea, eating problems, fatigue, flatulence, fluid in the abdomen or ascites, gastrointestinal (GI) dysbiosis, GI mucositis, inflammatory bowel disease, irritable bowel syndrome (IBS-D and IBS-C), nausea, pain, stool or urine changes, ulcerative colitis, vomiting, weight gain from retaining fluid, and/or weakness.

Diseases, Methods of Treatment, and Patient Selections

In embodiments, the present invention pertains to cancers and/or tumors; for example, the treatment or prevention of cancers and/or tumors. As described elsewhere herein, the treatment of cancer may involve in embodiments, modulating the immune system with the present chimeric proteins to favor immune stimulation over immune inhibition.

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g., virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In embodiments, the chimeric protein is used to treat a subject that has a treatment-refractory cancer. In embodiments, the chimeric protein is used to treat a subject that is refractory to one or more immune-modulating agents. For example, in embodiments, the chimeric protein is used to treat a subject that presents no response to treatment, or even progress, after 12 weeks or so of treatment. For instance, in embodiments, the subject is refractory to a PD-1 and/or PD-L1 and/or PD-L2 agent, including, for example, nivolumab (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), Ibrutinib (PHARMACYCLICS/ABBVIE), atezolizumab (TECENTRIQ, GENENTECH), and/or MPDL3280A (ROCHE)-refractory patients. For instance, in embodiments, the subject is refractory to an anti-CTLA-4 agent, e.g., ipilimumab (YERVOY)-refractory patients (e.g., melanoma patients). Accordingly, in embodiments the present invention provides methods of cancer treatment that rescue patients that are non-responsive to various therapies, including monotherapy of one or more immune-modulating agents.

In embodiments, the present methods provide treatment with the chimeric protein in a patient who is refractory to an additional agent, such "additional agents" being described elsewhere herein, inclusive, without limitation, of the various chemotherapeutic agents described herein.

In embodiments, the chimeric proteins are used to treat, control or prevent one or more inflammatory diseases or conditions. Non-limiting examples of inflammatory diseases include acne vulgaris, acute inflammation, allergic rhinitis, asthma, atherosclerosis, atopic dermatitis, autoimmune disease, autoinflammatory diseases, autosomal recessive spastic ataxia, bronchiectasis, celiac disease, chronic cholecystitis, chronic inflammation, chronic prostatitis, colitis, diverticulitis, familial eosinophilia (fe), glomerulonephritis, glycerol kinase deficiency, hidradenitis suppurativa, hypersensitivities, inflammation, inflammatory bowel diseases, inflammatory pelvic disease, interstitial cystitis, laryngeal inflammatory disease, Leigh syndrome, lichen planus, mast cell activation syndrome, mastocytosis, ocular inflammatory disease, otitis, pain, pelvic inflammatory disease, reperfusion injury, respiratory disease, restenosis, rheumatic fever, rheumatoid arthritis, rhinitis, sarcoidosis, septic shock, silicosis and other pneumoconioses, transplant rejection, tuberculosis, and vasculitis.

In embodiments, the inflammatory disease is an autoimmune disease or condition, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

In aspects, the present chimeric agents are used in methods of activating an antigen presenting cell, e.g., via the extracellular domain of CD40L.

In aspects, the present chimeric agents are used in methods of preventing the cellular transmission of an immunosuppressive signal via the extracellular domain of CSF1R.

Combination Therapies and Conjugation

In embodiments, the invention provides for chimeric proteins and methods that further comprise administering an additional agent to a subject. In embodiments, the invention pertains to co-administration and/or co-formulation. Any of the compositions described herein may be co-formulated and/or co-administered.

In embodiments, any chimeric protein described herein acts synergistically when co-administered with another agent and is administered at doses that are lower than the doses commonly employed when such agents are used as monotherapy. In embodiments, any agent referenced herein may be used in combination with any of the chimeric proteins described herein.

In embodiments, the present chimeric protein comprising the extracellular domain of CSF1R as described herein is co-administered with another chimeric protein. In embodiments, the present chimeric protein comprising the extracellular domain of CSF1R as described herein is co-administered with another chimeric protein, for example, one which modulates the adaptive immune response. In embodiments, the present chimeric protein comprising the extracellular domain of CSF1R as described herein is co-administered with a chimeric protein comprising one or more of OX40L, PD-1, GITRL, 4-1BBL, SIRPα, TIM3, TIGIT, LIGHT and VSIG8. Without wishing to be bound by theory, it is believed that a combined regimen involving the administration of the present chimeric protein which induces an innate immune response and one or more chimeric proteins which induces an adaptive immune response may provide synergistic effects (e.g., synergistic anti-tumor effects).

Any chimeric protein which induces an adaptive immune response may be utilized in the present invention. For example, the chimeric protein may be any of the chimeric proteins disclosed in U.S. 62/464,002 which induce an adaptive immune response. In such embodiments, the chimeric protein comprises a first extracellular domain of a type I transmembrane protein at or near the N-terminus and a second extracellular domain of a type II transmembrane protein at or near the C-terminus, wherein one of the first and second extracellular domains provides an immune inhibitory signal and one of the first and second extracellular domains provides an immune stimulatory signal as disclosed in U.S. 62/464,002, the entire contents of which is hereby incorporated by reference. In an exemplary embodiment, the chimeric protein which induces an adaptive immune response is a chimeric protein comprising the extracellular domain of PD-1 at the N-terminus and the extracellular domain of OX40L, GITRL, or 4-1BBL at the C-terminus. In an embodiment, the chimeric protein which induces an adaptive immune response is a chimeric protein comprising the extracellular domain of VSIG8 at the N-terminus and the extracellular domain of OX40L, GITRL, or 4-1BBL at the C-terminus.

In embodiments, the present chimeric protein comprising the extracellular domain of CSF1R as described herein is administered to a patient to stimulate the innate immune response and, subsequently (e.g., 1 day later, or 2 days later, or 3 days later, or 4 days later, or 5 days later, or 6 days later, or 1 week later, or 2 weeks later, or 3 weeks later, or 4 weeks later) a chimeric protein which induce an adaptive immune response is administered.

In embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111), and TAXOTERE doxetaxel (Rhone-Poulenc Rorer, Antony, France); chloranbucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In embodiments, inclusive of, without limitation, cancer applications, the present additional agent is one or more immune-modulating agents selected from an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), pidilizumab (CT-011, CURE TECH), MK-3475 (MERCK), BMS 936559 (BRISTOL MYERS SQUIBB), atezolizumab (TECENTRIQ, GENENTECH), MPDL328OA (ROCHE)), an agent that increases and/or stimulates CD137 (4-1BB) and/or the binding of CD137 (4-1BB) with one or more of 4-1BB ligand (by way of non-limiting example, urelumab (BMS-663513 and anti-4-1BB antibody), and an agent that blocks, reduces and/or inhibits the activity of CTLA-4 and/or the binding of CTLA-4 with one or more of AP2M1, CD80, CD86, SHP-2, and PPP2R5A and/or the binding of OX40 with OX40L (by way of non-limiting example GBR 830 (GLENMARK), MED16469 (MEDIMMUNE).

In embodiments, inclusive of, without limitation, infectious disease applications, the present invention pertains to anti-infectives as additional agents. In embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In embodiments, inclusive, without limitation, of autoimmune applications, the additional agent is an immunosuppressive agent. In embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin).

In embodiments, the chimeric proteins (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids. In still embodiments, the chimeric proteins (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The chimeric proteins (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Formulations

The chimeric proteins (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In embodiments, the compositions described herein are in the form of a pharmaceutically acceptable salt.

Further, any chimeric protein (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In embodiments, the compositions described herein are suspended in a saline buffer (including, without limitation TBS, PBS, and the like).

In embodiments, the chimeric proteins may by conjugated and/or fused with another agent to extend half-life or otherwise improve pharmacodynamic and pharmacokinetic properties. In embodiments, the chimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In embodiments, each of the individual chimeric proteins is fused to one or more of the agents described in BioDrugs (2015) 29:215-239, the entire contents of which are hereby incorporated by reference.

Administration, Dosing, and Treatment Regimens

The present invention includes the described chimeric protein (and/or additional agents) in various formulations. Any chimeric protein (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the formulations comprising the chimeric protein (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the chimeric protein (and/or additional agents) of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, any chimeric protein (and/or additional agents) described herein is formulated in accordance with routine procedures as a composition adapted for a mode of administration described herein.

Routes of administration include, for example: intratumoral, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In embodiments, the administering is effected orally or by parenteral injection. In some instances, administration results in the release of any agent described herein into the bloodstream, or alternatively, the agent is administered directly to the site of active disease.

Any chimeric protein (and/or additional agents) described herein can be administered orally. Such chimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment. In one embodiment, for instance in the treatment of cancer, the chimeric protein (and/or additional agents) are administered in the tumor microenvironment (e.g., cells, molecules, extracellular matrix and/or blood vessels that surround and/or feed a tumor cell, inclusive of, for example, tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor) or lymph node and/or targeted to the tumor microenvironment or lymph node. In embodiments, for instance in the treatment of cancer, the chimeric protein (and/or additional agents) are administered intratumorally.

In the embodiments, the present chimeric protein allows for a dual effect that provides less side effects than are seen in conventional immunotherapy (e.g., treatments with one or more of OPDIVO, KEYTRUDA, YERVOY, and TECENTRIQ). For example, the present chimeric proteins reduce or prevent commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease. Further, the present local administration, e.g., intratumorally, obviate adverse event seen with standard systemic administration, e.g., IV infusions, as are used with conventional immunotherapy (e.g., treatments with one or more of OPDIVO, KEYTRUDA, YERVOY, and TECENTRIQ).

Dosage forms suitable for parenteral administration (e.g., intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g., lyophilized composition), which can be dissolved or suspended in sterile injectable medium immediately before use. They may contain, for example, suspending or dispersing agents known in the art.

The dosage of any chimeric protein (and/or additional agents) described herein as well as the dosing schedule can depend on various parameters, including, but not limited to, the disease being treated, the subject's general health, and the administering physician's discretion.

Any chimeric protein described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof. In embodiments any chimeric protein and additional agent described herein are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart.

In embodiments, the present invention relates to the co-administration of the present chimeric protein comprising the extracellular domain of colony stimulating factor 1 receptor (CSF1R) and another chimeric protein which induces an adaptive immune response. In such embodiments, the present chimeric protein may be administered before, concurrently with, or subsequent to administration of the chimeric protein which induces an adaptive immune response. For example, the chimeric proteins may be administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days part, 4 days apart, 5 days apart, 6 days apart, 1 week apart, 2 weeks apart, 3 weeks apart, or 4 weeks apart. In an exemplary embodiment, the present chimeric protein comprising the extracellular domain of CSF1R and the chimeric protein which induces an adaptive immune response are administered 1 week apart, or administered on alternate weeks (i.e., administration of the present chimeric protein comprising the extracellular domain of CSF1R is followed 1 week later with administration of the chimeric protein inducing an adaptive immune response and so forth).

The dosage of any chimeric protein (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected. For administration of any chimeric protein (and/or additional agents) described herein by parenteral injection, the dosage may be about 0.1 mg to about 250 mg per day, about 1 mg to about 20 mg per day, or about 3 mg to about 5 mg per day. Generally, when orally or parenterally administered, the dosage of any agent described herein may be about 0.1 mg to about 1500 mg per day, or about 0.5 mg to about 10 mg per day, or about 0.5 mg to about 5 mg per day, or about 200 to about 1,200 mg per day (e.g., about 200 mg, about 300 mg, about 400 mg, about 500 mg, about 600 mg, about 700 mg, about 800 mg, about 900 mg, about 1,000 mg, about 1,100 mg, about 1,200 mg per day).

In embodiments, administration of the chimeric protein (and/or additional agents) described herein is by parenteral injection at a dosage of about 0.1 mg to about 1500 mg per treatment, or about 0.5 mg to about 10 mg per treatment, or about 0.5 mg to about 5 mg per treatment, or about 200 to about 1,200 mg per treatment (e.g., about 200 mg, about 300 mg, about 400 mg, about 500 mg, about 600 mg, about 700 mg, about 800 mg, about 900 mg, about 1,000 mg, about 1,100 mg, about 1,200 mg per treatment).

In embodiments, a suitable dosage of the chimeric protein (and/or additional agents) is in a range of about 0.01 mg/kg to about 100 mg/kg of body weight, or about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween. In an embodiment, delivery can be in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989).

Any chimeric protein (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543;

5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In an embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In an embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any chimeric protein (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any chimeric protein (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any chimeric protein (and/or additional agents) described herein can be administered in a single daily dose, or the total daily dosage can be administered in divided doses of two, three or four times daily. Furthermore, any chimeric protein (and/or additional agents) described herein can be administered continuously rather than intermittently throughout the dosage regimen.

Cells and Nucleic Acids

In embodiments, the present invention provides an expression vector, comprising a nucleic acid encoding the chimeric protein described herein. In embodiments, the expression vector comprises DNA or RNA. In embodiments, the expression vector is a mammalian expression vector.

Both prokaryotic and eukaryotic vectors can be used for expression of the chimeric protein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, lpp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the chimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the fusion proteins in recombinant host cells.

In embodiments, expression vectors of the invention comprise a nucleic acid encoding the chimeric proteins (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In embodiments, the cell is a tumor cell. In an embodiment, the cell is a non-tumor cell. In embodiments, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In embodiments, the present invention contemplates the use of inducible promoters capable of effecting high level of expression transiently in response to a cue. For example, when in the proximity of a tumor cell, a cell transformed with an expression vector for the chimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations, it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al, J. Biol. Chem. 262, 4429-4432 (1987); and Wagner et al, Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al, TIG 15:326-332, 1999; Kootstra et al, Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al, J. Mol. Biol. 335:667-678, 2004), sleeping beauty, transposases of the mariner family (Plasterk et al, supra), and components for integrating viruses such as AAV, retroviruses, and antiviruses having components that provide for virus integration such as the LTR sequences of retroviruses or lentivirus and the ITR sequences of AAV (Kootstra et al, Ann. Rev. Pharm. Toxicol., 43:413-439, 2003). In addition, direct and targeted genetic integration strategies may be used to insert nucleic acid sequences encoding the chimeric proteins including CRISPR/CAS9, zinc finger, TALEN, and meganuclease gene-editing technologies.

In aspects, the invention provides expression vectors for the expression of the chimeric proteins (and/or additional agents) that are viral vectors. Many viral vectors useful for gene therapy are known (see, e.g., Lundstrom, Trends Biotechnol., 21: 117, 122, 2003. Illustrative viral vectors include those selected from Antiviruses (LV), retroviruses (RV), adenoviruses (AV), adeno-associated viruses (AAV), and α viruses, though other viral vectors may also be used. For in vivo uses, viral vectors that do not integrate into the host genome are suitable for use, such as a viruses and adenoviruses. Illustrative types of α viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In one embodiment, the invention provides methods of transducing a human cell in vivo, comprising contacting a solid tumor in vivo with a viral vector of the invention.

In embodiments, the present invention provides a host cell, comprising the expression vector comprising the chimeric protein described herein.

Expression vectors can be introduced into host cells for producing the present chimeric proteins. Cells may be cultured in vitro or genetically engineered, for example. Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al, *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Aced Sci USA* 1980, 77:4216); DG44 CHO cells, CHO-K1 cells, mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the fusion proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC #2 and SCLC #7.

Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production of the present chimeric proteins in vitro, ex vivo, and/or in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, fetal liver, etc. The choice of cell type depends on the type of tumor or infectious disease being treated or prevented, and can be determined by one of skill in the art.

Subjects and/or Animals

In embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In embodiments, the subject and/or animal is a non-mammal, such, for example, a zebrafish. In embodiments, the subject and/or animal may comprise fluorescently-tagged cells (e.g., with GFP). In embodiments, the subject and/or animal is a transgenic animal comprising a fluorescent cell.

In embodiments, the subject and/or animal is a human. In embodiments, the human is a pediatric human. In embodiments, the human is an adult human. In embodiments, the human is a geriatric human. In embodiments, the human may be referred to as a patient.

In embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

Any aspect or embodiment described herein can be combined with any other aspect or embodiment as disclosed herein.

The invention will be further described in the following examples, which do not limit the scope of the invention described in the claims.

EXAMPLES

Example 1: Predicted Mechanism of Action and in Silico Predicted Structure of Monomeric CSF1R-Fc-CD40L Chimeric Protein FIG. 1A shows a schematic representation of the expected mechanism of action of a CSF1R-Fc-CD40L chimeric protein. The CSF1R domain binds CSF1 and/or IL-34 to provide a 'sink effect' and prevent CSF1 and/or IL-34 from binding CSF1R on the surface of antigen presenting cells, thereby blocking an immune inhibition signal. Contemporaneously, the CD40L domain of the chimeric protein binds CD40 on the surface of antigen presenting cells, thereby providing an immune activation signal. The net effect of these two events increases an immune response by blocking an inhibitory signal (via IL-34 and/or CSF1) and providing an activating signal via CD40.

Figure 1B:
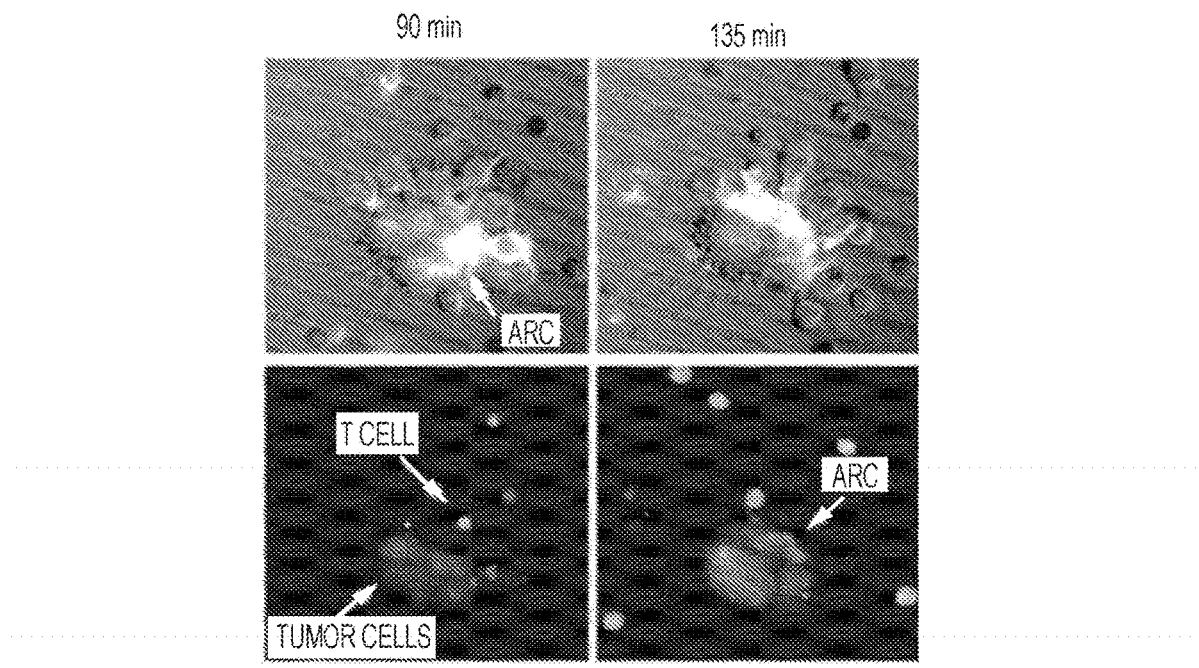
FIG. 1B shows a synapse that has formed by a chimeric protein between a tumor cell and a T cell.

FIG. 1B shows a synapse that has formed by a chimeric protein between a tumor cell and a T cell.

Figure 1C:
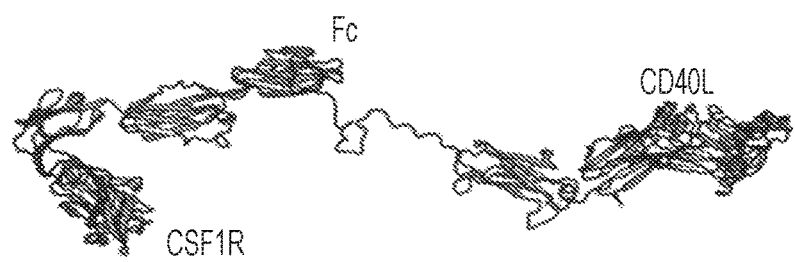
FIG. 1C shows the predicted secondary structure of human CSF1R-Fc-CD40L, indicating how the three domains are predicted to form in their natural state. The CSF1R-Fc-CD40L chimeric protein's predicted monomeric molecular weight is about 105.4 kDa.

FIG. 1C shows an in silico structure prediction of the monomeric CSF1R-Fc-CD40L chimeric protein (SL-115154) having 947 amino acid residues (SEQ ID NO: 5), with a p-value $1.69 \times 10^{-29}$. The molecular weight of the monomeric protein was predicted to be 105.4 kDa. A structure of the chimeric protein is provided in FIG. 1A.

Specifically, the structure prediction revealed that 33 amino acid positions (3%) may be disordered. Secondary structure prediction of the entire sequence of the chimeric protein showed that the protein has the composition of 2% α-helix (H), 51% β-sheet (E), and 45% coil (C). The GDT (global distance test) and uGDT (un-normalized GDT) for the absolute global quality were also calculated for the chimeric protein to give an overall uGDT(GDT) of 738 (78).

The three-state prediction for solvent accessibility of the protein residues were 33% exposed (E), 46% intermediate (M), and 19% buried (B).

Example 2: Characterization of CSF1R-Fc-CD40L Chimeric Protein

A human CSF1R-Fc-CD40L (also referred to as CD115-Fc-CD40L herein) chimeric protein was constructed as described above in the Detailed Description and in U.S. 62/464,002, the contents of which are hereby incorporated by reference in its entirety. The chimeric protein was characterized by performing a Western blot analysis against each individual domain of the chimeric protein, i.e., via anti-CSF1R, anti-Fc, and anti-CD40L antibodies.

Figure 2:
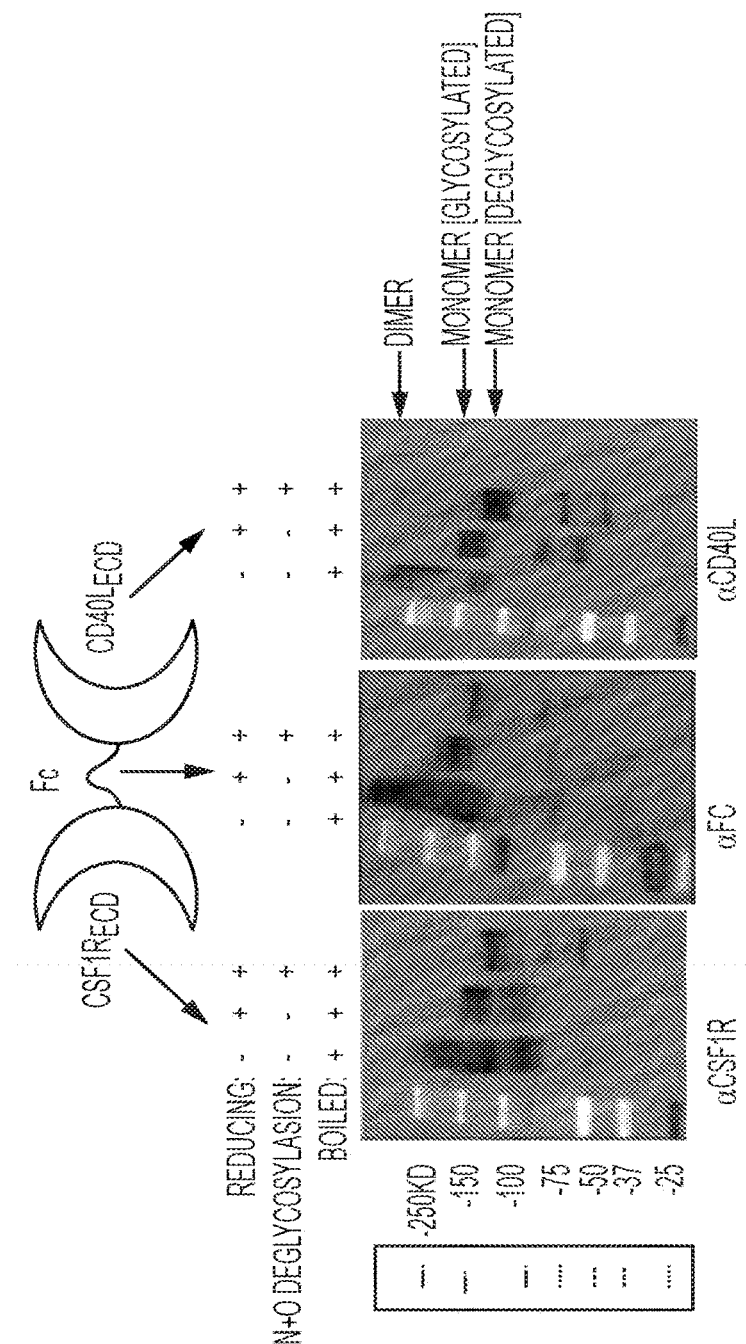
FIG. 2 shows characterization by Western blot analysis of the three domains of human CSF1R-Fc-CD40L under non-reducing/boiled, reducing/boiled, and reducing/deglycosylating/boiled (PNGase) conditions. The band sizes confirm the predicted monomeric molecular weight of about 105.4 kDa and suggests that the native state exists as a glycosylated dimer. As shown, lane 1, starting from the left in each blot, is a protein molecular weight marker.

The Western blots indicated the presence of an oligomeric species (possibly a dimer), with an apparent molecular weight of approximately 240 kDa, in the non-reduced lanes (FIG. 2, lane 2 in each blot), which was reduced to a glycosylated monomeric band in the presence of the reducing agent, β-mercaptoethanol (FIG. 2, lane 3 in each blot). As shown in FIG. 2, lane 4 in each blot, the chimeric protein ran as a monomer at the predicted molecular weight of approximately 105 kDa in the presence of both a reducing agent (6-mercaptoethanol) and an endoglycosidase (PN-Gase).

Figure 3:
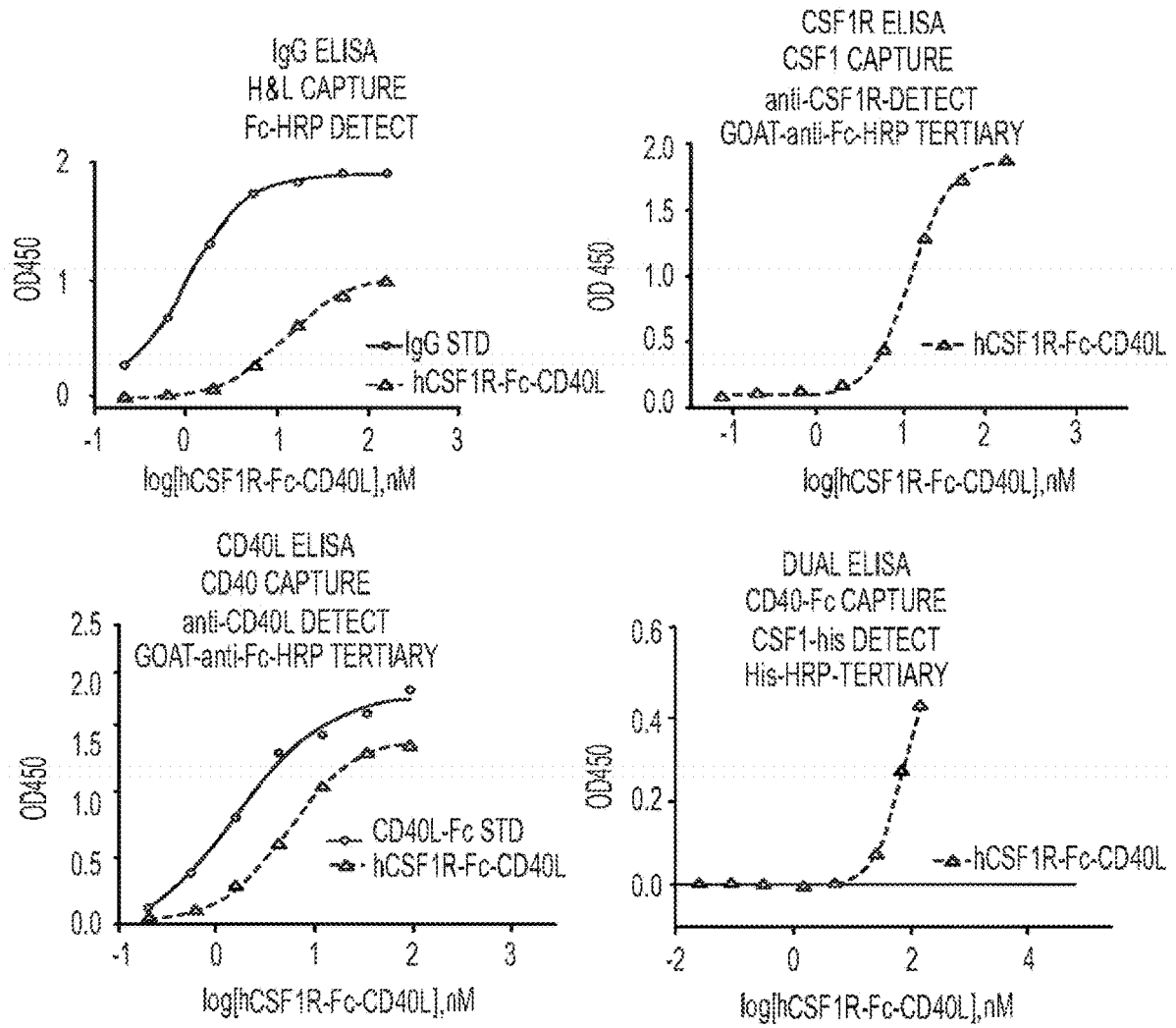
FIG. 3 shows functional enzyme linked immunosorbent assays (ELISAs) demonstrating binding of human CSF1R-Fc-CD40L to the targets of the three domains individually (Fc—shown in the upper left, CSF1R—shown in the upper right, and CD40L—shown in the lower left) as well as the contemporaneous binding to both recombinant CSF1 and CD40—shown in the lower right. In the upper left panel, the top curve is IgG standard and the bottom curve hCSFR1-Fc-CD40L. In the bottom left panel, the top curve is CD40L-Fc and the bottom curve hCSFR1-Fc-CD40L.

Example 3: Characterization of the Binding Affinity of the Different Domains of the CSF1R-Fc-CD40L Chimeric Protein Using ELISA Enzyme-Linked Immunosorbent assay (ELISA) assays were developed to demonstrate the binding affinity of the different domains of the hCSF1R-Fc-CD40L (also referred to as CD115-Fc-CD40L herein) to their respective binding partners (i.e., CSF1, hIgG, or CD40). Specifically, the Fc portion of the chimeric protein was detected by capturing to a plate-bound human IgG and detecting via an HRP-conjugated anti-human IgG antibody (upper left quadrant of FIG. 3). The CSF1R domain of the hCSF1R-Fc-CD40L chimeric protein was detected by capturing to a plate-bound recombinant human CSF1 protein and detecting via a HRP-conjugated anti-human IgG antibody (upper right quadrant of FIG. 3). The CD40L domain of the chimeric protein was detected by capturing to a plate-bound recombinant human CD40 protein and detecting via a CD40L-specific antibody (bottom left quadrant of FIG. 3). Finally, contemporaneous binding to both CSF1 and CD40 was demonstrated using a dual ELISA format in which recombinant CD40 was used to capture CSF1R-Fc-CD40L and recombinant CSF1 was used to detect CSF1R-Fc-CD40L (bottom right portion of FIG. 3).

Example 4: Characterization of the Ex Vivo Cell Binding Affinity of the CSF1R-Fc-CD40L Chimeric Protein Cell binding assays were performed to demonstrate the binding affinity of the different domains of the mCSF1R-Fc-CD40L chimeric protein towards their respective binding partners on the surface of a mammalian cell membrane.

For cell binding assays, immortalized cell lines were engineered to stably express CD40 (Jurkat/CD40). Increasing concentrations of the CSF1R-Fc-CD40L chimeric protein were incubated with the over-expressing (Jurkat/CD40) cell line for 2 hours. Cells were collected, washed, and stained with antibodies for the detection of chimeric protein binding by flow cytometry.

Figure 4:
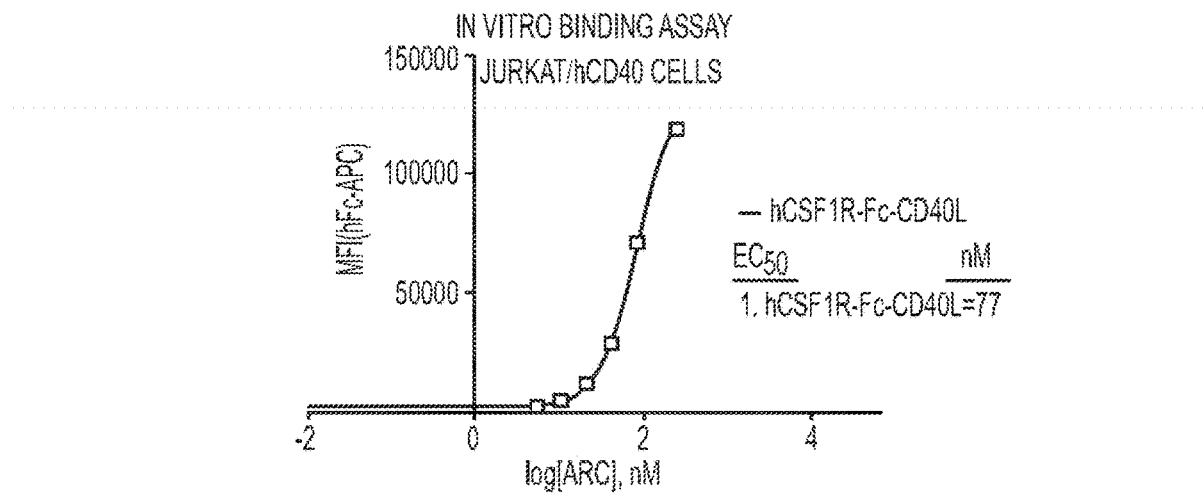
FIG. 4 shows in vitro cell binding assays which demonstrate the ability of the human CSF1R(CD115)-Fc-CD40L chimeric protein to bind the CD40 receptor expressed by Jurkat cells (a human T cell line). The binding $EC_{50}$ was measured to be 77 nM. "ARC" refers to the hCSF1R-Fc-CD40L chimeric protein.

As shown in FIG. 4, the CSF1R-Fc-CD40L chimeric protein bound to CD40 present on the cell surface in a concentration-dependent manner and with low nM affinity. Specifically, as shown in FIG. 4, the cell binding assay demonstrated that CSF1R-Fc-CD40L binds to CD40 and with an affinity of about 77 nM (according to the $EC_{50}$ calculation).

Example 5: Characterization of the Binding Affinity of the CSF1R-Fc-CD40L Chimeric Protein by Surface Plasmon Resonance (SPR) and Bio-Layer Surface Interferometry The binding affinity of the different domains of the hCSF1R-Fc-CD40L chimeric protein was measured by the surface plasmon resonance (SPR) using the BioRad ProteOn XPR 360 system. Specifically, the affinity of the chimeric protein for human CSF1 and CD40 was determined and compared to recombinant control proteins, and the results are shown in the Table below:

|  | Sample | Ka (on-rate 1/Ms) | Kd (off-rate 1/s) | KD (binding; M) |
|---|---|---|---|---|
| Binding to: CSF | CSF1R-Fc | 1.22E+6 | 3.35E−4 | .275 nM |
| CD40 | CSF1R-Fc-CD40L | 5.70E+4 | 7.30E−6 | .128 nM |
|  | CD40L-Fc | NA | NA | NA |
|  | CSF1R-Fc-CD40L | 1.28E+4 | 6.74E−6 | .527 nM |

It was determined that the hCSF1R-Fc-CD40L chimeric protein binds to CSF1 and CD40 with high affinity. In particular, it was noted that the off-rates of the hCSF1R-Fc-CD40L chimeric protein are much slower than the control proteins (i.e., CSF1R-Fc and CD40L-Fc). For example, the off-rate of the chimeric protein from CSF1 was 45.9 fold slower than the CSF1R-Fc protein.

In addition, the binding affinity of each domain of CSF1R-Fc-CD40L was measured using an Octet system based on Bio-Layer Surface Interferometry (FIG. 5A to FIG. 5F). These results further confirm high affinity binding of the CSF1R-Fc-CD40L chimeric protein to each binding partner.

Example 6. Binding Affinity to Both CSF1R Ligands

Figure 6:
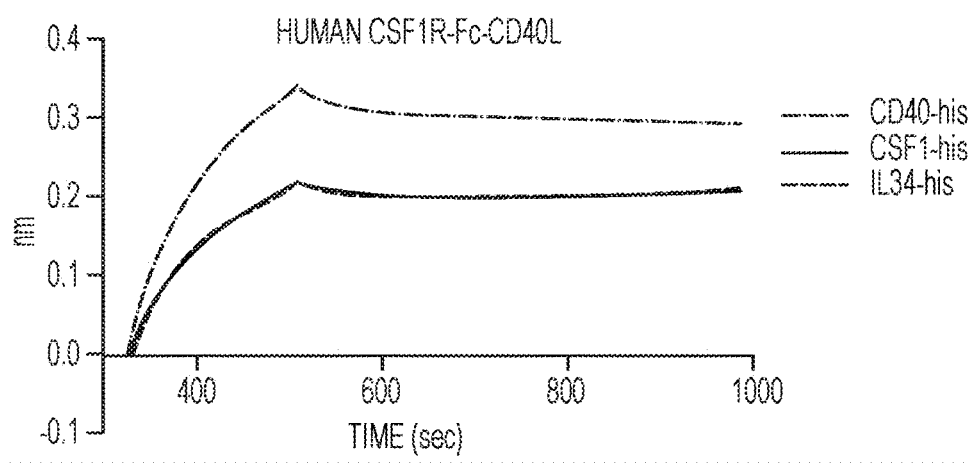
FIG. 6 shows characterization by biolayer interferometry (Octet) of the relative binding affinity of human CSF1R-Fc-CD40L to recombinant human CD40, CSF1, and IL-34. Identical binding was observed for the two CFF1R ligands: CSF1 and IL-34; thus, the curves overlay one another. Therefore, the order of the curves is: CD40-his on top and CSF1-his and IL-34-his on bottom and overlayed.

CSF1R has been reported to bind two ligands: CSF1 and IL-34. Thus, it was desirable to demonstrate that CSF1R-Fc-CD40L is capable of binding both CSF1 and IL-34. This was tested using bio-layer surface interferometry (Octet), with results shown in FIG. 6. The binding of CSF1R-Fc-CD40L to CSF1 and IL-34 was indistinguishable; thus, the curves are virtually overlayed on top of one another.

Example 7. Characterization of Murine CSF1R-Fc-CD40L Chimeric Protein

A murine CSF1R-Fc-CD40L (also referred to as mCSF1R-Fc-CD40L in the present disclosure) chimeric protein was constructed as described above in the Detailed Description and in U.S. 62/464,002, the contents of which are hereby incorporated by reference in its entirety. The chimeric protein was characterized by performing a Western blot analysis against each individual domain of the chimeric protein, i.e., via α-CSF1R, α-Fc, and α-CD40L antibodies.

Figure 7A:
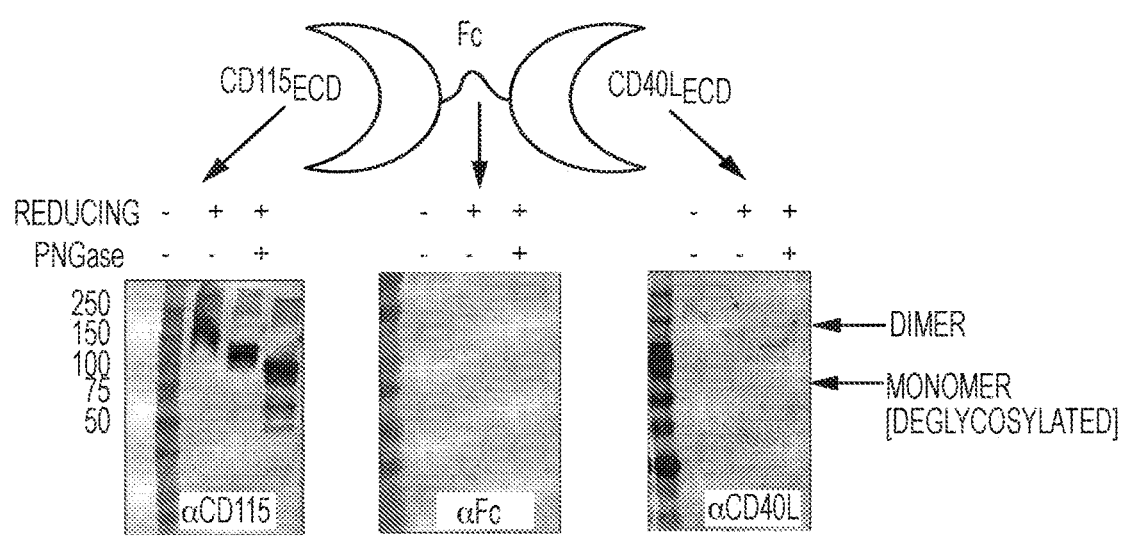
FIG. 7A and FIG. 7B show characterization by Western blot and functional ELISA binding of the murine CSF1R-Fc-CD40L.

The Western blots indicated the presence of an oligomeric species (possibly a dimer), with an apparent molecular weight of approximately 240 kDa in the non-reduced lanes (FIG. 7A, lane 2 in each blot), which was reduced to a glycosylated monomeric band in the presence of the reducing agent, β-mercaptoethanol (FIG. 7A, lane 3 in each blot). As shown in FIG. 7A, lane 4 in each blot, the chimeric protein ran as a monomer at the predicted molecular weight of approximately 105 kDa in the presence of both a reducing agent (β-mercaptoethanol) and an endoglycosidase (PN-Gase).

Enzyme-Linked Immunosorbent assay (ELISA) assays were developed to demonstrate the binding affinity of the different domains of the mCSF1R-Fc-CD40L to their respective binding partners (i.e., CSF1, mIgG, or CD40). Specifically, the Fc portion of the chimeric protein was detected by capturing to a plate-bound mouse IgG and detecting via an HRP-conjugated anti-mouse IgG antibody (middle graph of FIG. 7B). The CSF1R domain of the mCSF1R-Fc-CD40L chimeric protein was detected by capturing to a plate-bound recombinant murine CSF1 protein and detecting via a HRP-conjugated anti-mouse IgG antibody (left graph of FIG. 7B). The CD40L domain of the chimeric protein was detected by capturing to a plate-bound recombinant mouse CD40 protein and detecting via a CD40L-specific antibody (right graph of FIG. 7B).

Figure 7B:
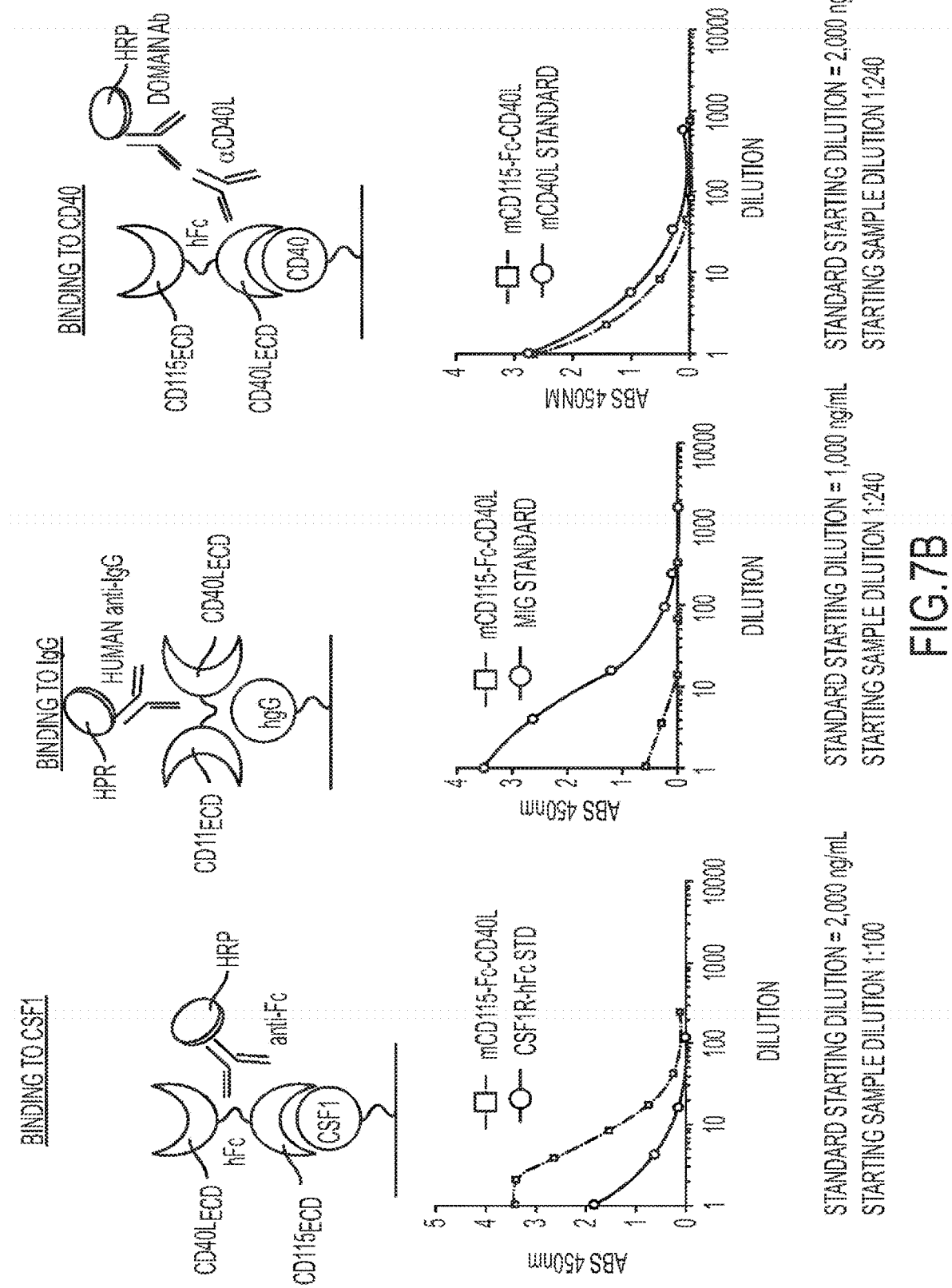

As shown in FIG. 7B, the different domains of the hCSF1R-Fc-CD40L chimeric protein effectively interacted with their respective binding partners with high affinity. Nevertheless, it was observed that in ELISA assays, using the central Fc region to detect chimeric proteins tended to underestimate the actual protein content in a sample. Therefore, low level of the hCSF1R-Fc-CD40L chimeric protein was detected compared to standard in this assay.

Example 8. Characterization of the Ex Vivo Cell Binding Affinity of the Murine CSF1R-Fc-CD40L Chimeric Protein Cell binding assays were performed to demonstrate the binding affinity of the different domains of the mCSF1R-Fc-CD40L chimeric protein towards their respective binding partners on the surface of a mammalian cell membrane.

For cell binding assays, immortalized cell lines were engineered to stably express CD40 (CHOK1/CD40). Increasing concentrations of the murine CSF1R-Fc-CD40L chimeric protein were incubated with the over-expressing (CHOK1/CD40) cell line for 2 hours. Cells were collected, washed, and stained with antibodies for the detection of chimeric protein binding by flow cytometry.

Figure 8:
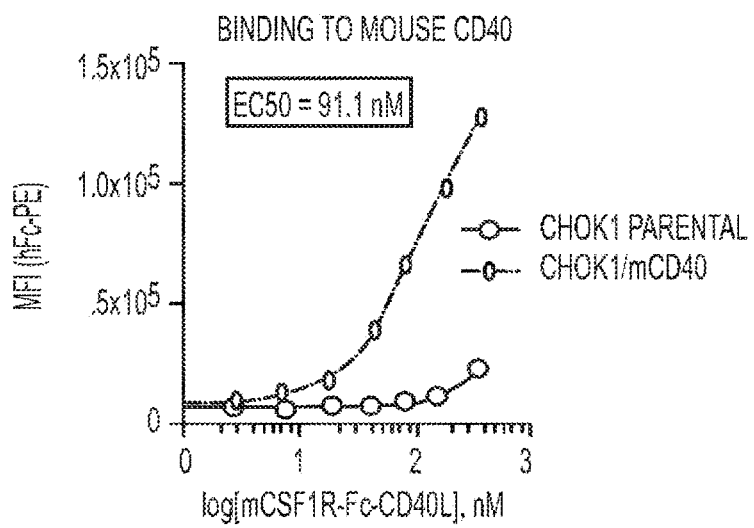
FIG. 8 shows in vitro cell binding of murine CSF1R-Fc-CD40L to CHO-K1 cells which overexpress murine CD40 (top curve), as compared to a parental CHO-K1 cell line that does not express mCD40 (bottom curve). The binding $EC_{50}$ was measured at 91.1 nM.

As shown in FIG. 8, the murine CSF1R-Fc-CD40L chimeric protein bound to CD40 present on the cell surface in a concentration-dependent manner and with low nM affinity. Specifically, as shown in FIG. 8, the cell binding assay demonstrated that CSF1R-Fc-CD40L bound to CD40 with an affinity of 91.1 nM (according to the $EC_{50}$ calculation). As a negative control, there was no detectable binding to the parental (non-CD40 expressing) CHOK1 cell line.

Example 9. Induction of CD40 Signaling in Vitro

Figure 9:
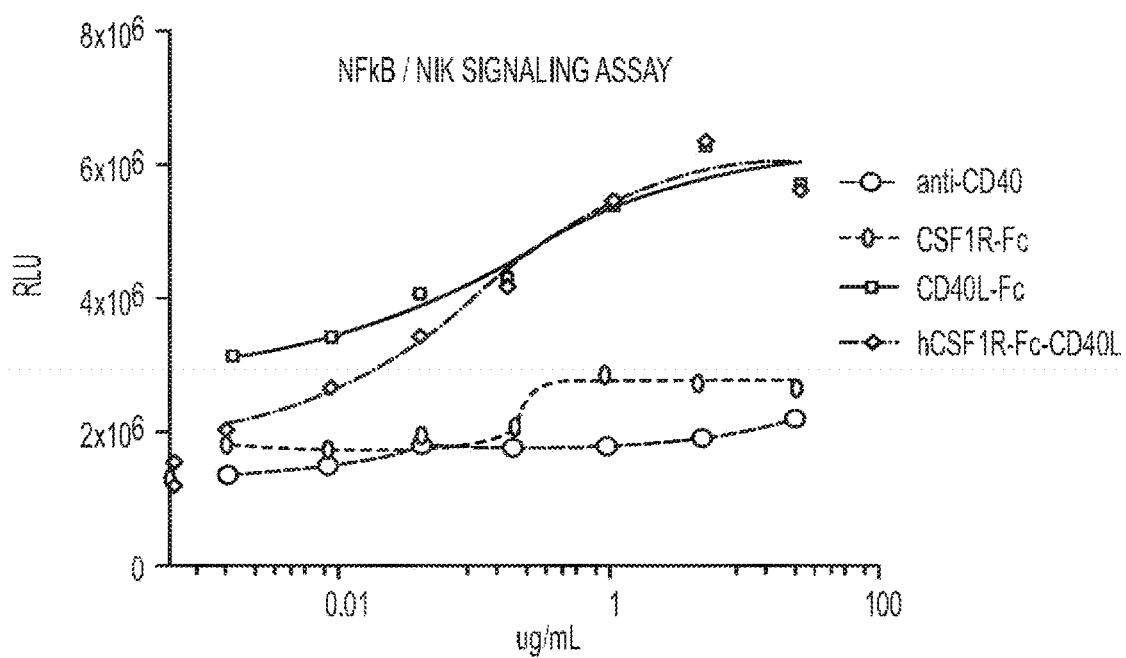
FIG. 9 shows data from an in vitro NF-κB/NIK signaling assay using the human CSF1R-Fc-CD40L chimeric protein. U2OS cells from the DiscoverX NIK signaling assay were cultured with a titration of either a commercially-available single-sided CD40L-Fc, single-sided CSF1R-Fc, or anti-CD40, or the human CSF1R-Fc-CD40L chimeric protein. The relative luciferase units (RLU) indicate the relative strength of NF-κB/NIK signaling activated following treatment with the indicated regimens. The curves are identified as follows: at 0.01 μg/mL on the X-axis, top to bottom is: CD40L-Fc, hCSF1R-Fc-CD40L, CSF1R-Fc, and anti-CD40.

Human CD40 is a homo-trimeric receptor that, when activated, leads to induction of a signaling cascade which involves both NF-κB and NIK activation. FIG. 9 shows example data from an in vitro NF-κB/NIK signaling assay using the human CSF1R-Fc-CD40L chimeric protein. U2OS cells from the DiscoverX NIK signaling assay were cultured with a titration of either a commercially-available single-sided CD40L-Fc, single-sided single-sided CSF1R-Fc, or a CD40 agonist antibody, or the human CSF1R-Fc-CD40L chimeric protein. The relative luciferase units (RLU) indicate the relative strength of NF-κB/NIK signaling activated following treatment with the indicated regimens. hCSF1R-Fc-CD40L is shown to have strongly activated signaling via NF-κB and NIK, to a comparable degree as a CD40L-Fc chimeric protein. The CD40 agonist antibody did not stimulate CD40 activation in this assay because the antibody requires Fc receptor cross-linking in order to facilitate appropriate clustering of the CD40 receptor.

Example 10: Functional Assays of the CSF1R-Fc-CD40L Chimeric Protein

CSF1R (also known as CD115) has been identified as an emergent immune checkpoint due to its role in binding to CSF1 and/or IL-34 within the tumor microenvironment. As shown in FIG. 1A, binding of CSF1R to either of these two ligands stimulates immune suppression through various mechanisms, including the induction of myeloid derived suppressor cells. Without wishing to be bound by theory, it is believed that the CSF1R-Fc-CD40L chimeric protein may contemporaneously act as a cytokine trap for CSF1/IL-34 and stimulates macrophages and antigen presenting cells via CD40 thereby generating potent anti-tumor immunity.

Two functional assays were developed to characterize the functional activity of the mCSF1R-Fc-CD40L chimeric protein.

Figure 10A:
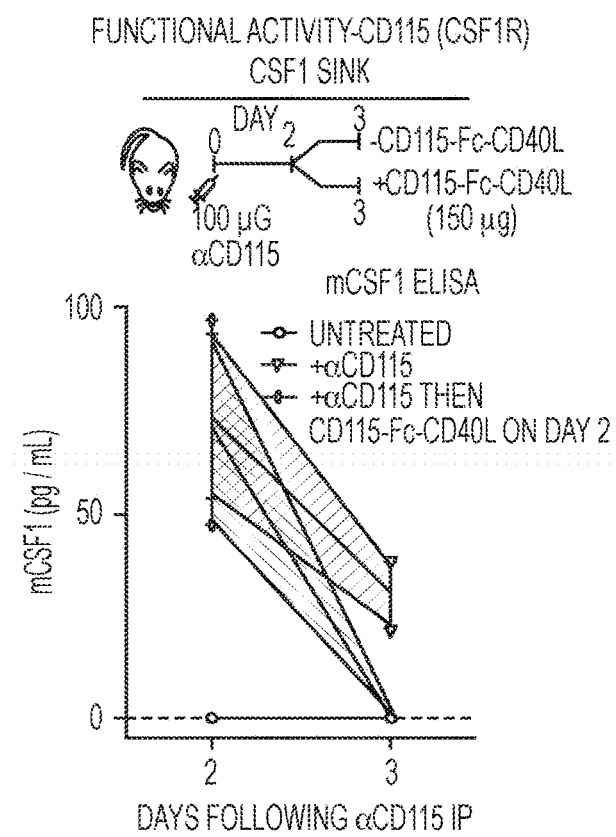
FIG. 10A and FIG. 10B show in vivo functional readouts of murine CSF1R-Fc-CD40L activity.

The first assay is an in vivo trap/sink assay for assessing the ability of the mCSF1R-Fc-CD40L chimeric protein to bind and reduce serum levels of soluble CSF1. Specifically, non-tumor-bearing mice were injected with a single dose of anti-CSF1R antibody (also known as anti-CD115 antibody) on day 0. On day 2, mice were either left untreated, or injected with a single dose of the CSF1R-Fc-CD40L chimeric protein. Blood serum was collected on day 2 before injection of the chimeric protein and on day 3 after treatment with the chimeric protein. ELISA assays of murine CSF1 were performed on the serum. As shown in FIG. 10A, the mCSF1R-Fc-CD40L chimeric protein was able to bind and significantly reduce the serum levels of soluble CSF1 thus eliminating its detection by ELISA.

Figure 10B:
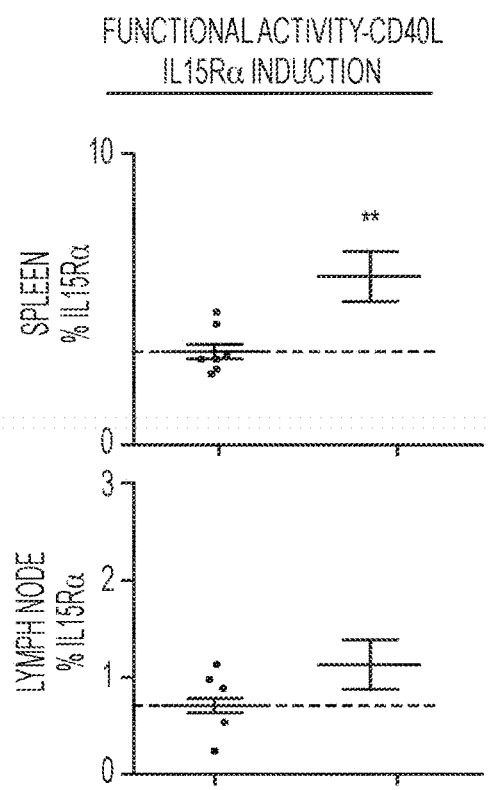

The second assay involved in vivo immune profiling of tumor-bearing mice 13 days after treatment with the mCSF1R-Fc-CD40L chimeric protein. Specifically, the levels of IL15Rα-F cells in the spleen and lymph nodes were analyzed as a readout for immune activation by the chimeric protein (particularly by the CD40L portion of the chimeric protein). Tumor-bearing mice were treated with two doses of 150 pg of the mCSF1R-Fc-CD40L chimeric protein on days 5 and 7 after initial tumor inoculation. On day 13, a cohort of mice was sacrificed and their spleens and lymph nodes were removed and dissociated for flow cytometry analysis of IL15Rα. Levels of IL15Rα-F cells in the spleen and lymph nodes were determined as shown in FIG. 10B. Consistent with a known mechanism of CD40L function, mice treated with the chimeric protein displayed an increase in IL15Rα in the spleen and lymph nodes compared to untreated mice, strongly suggesting that the chimeric protein stimulated immune activation via the CD40/CD40L pathway.

Example 11: Characterization of the in Vivo Anti-Tumor Activities of the CSF1R-Fc-CD40L Chimeric Protein The in vivo anti-tumor activity of the mCSF1R-Fc-CD40L chimeric protein was analyzed using the CT26 mouse colorectal tumor models.

In one set of experiments, Balb/c mice were inoculated with CT26 tumor cells on day 0 and/or rechallenged with a second inoculation of CT26 tumor cells at day 30. Following 5 days of tumor growth, when tumors reached a diameter of 4-5 mm, mice were treated with either CD40 agonist antibodies, CSF1R (CD115) blocking antibodies, the combination of those two antibodies, or the mCD115-Fc-CD40L chimeric protein. Treatments were repeated on day 7.

Figure 11B:
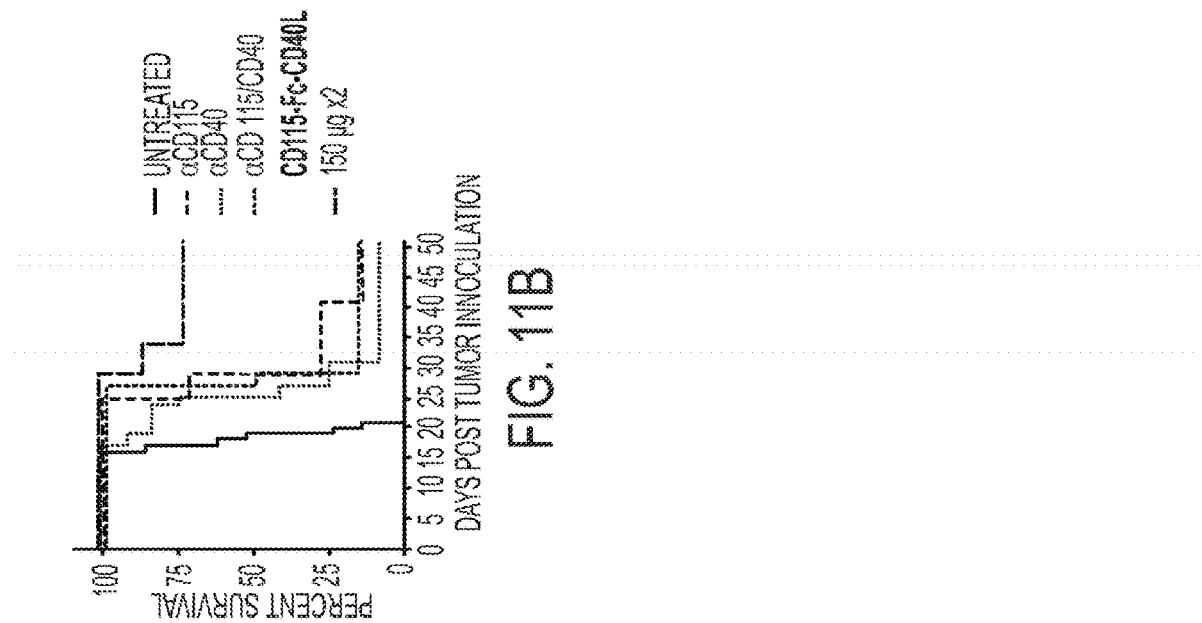
Figure 11A:
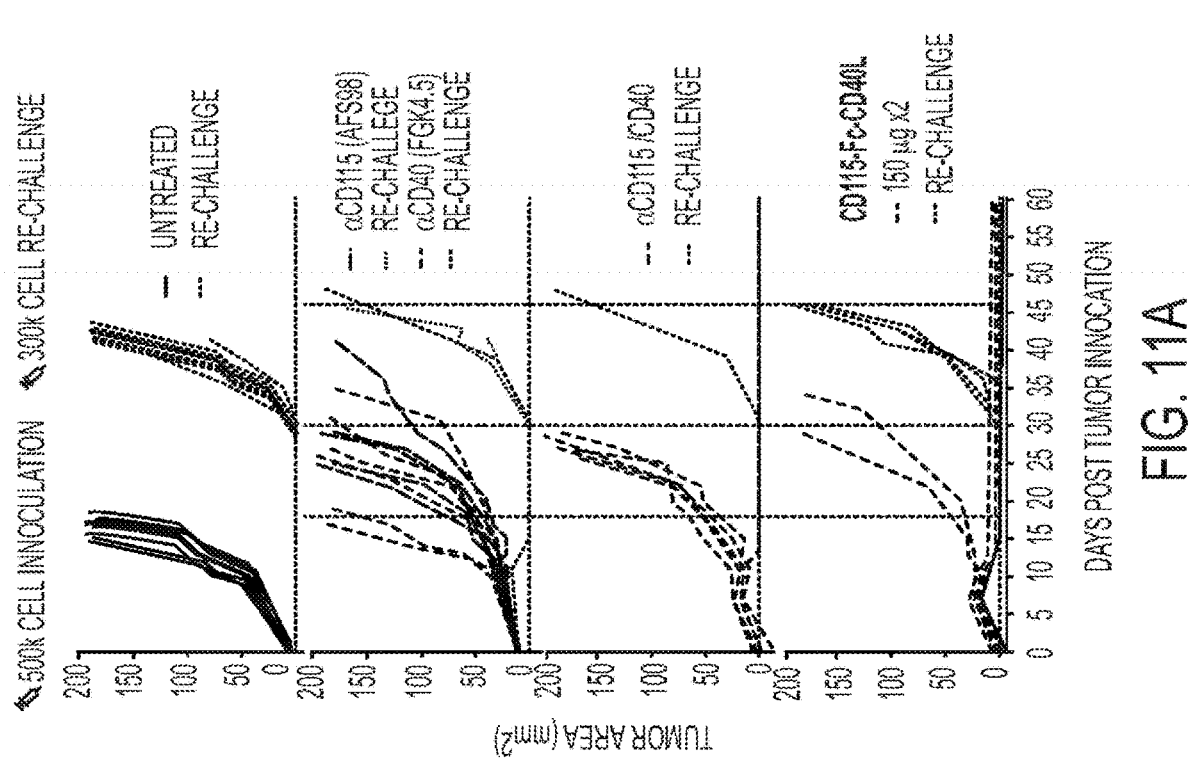

The tumor growth for each treatment group was assessed as shown in FIG. 11A. Specifically, the untreated mice developed tumors quickly. Treatment with either the CD40 agonist antibodies, CSF1R (CD115) blocking antibodies, or the combination of those two antibodies appeared to slightly delay the development of tumors. In comparison, treating mice with the mCD115-Fc-CD40L chimeric protein significantly prevented and/or delayed the development of tumors. The above data suggests that treatments with a CSF1R (CD115)-Fc-CD40L chimeric protein creates an immune memory effect in vivo. Thus, the treated animal is able to later attack tumor cells and/or prevent development of tumors when rechallenged after an initial treatment with the chimeric protein.

The overall survival percentage of mice through 50 days after tumor inoculation was also assessed. All of the untreated mice died within 30 days after tumor inoculation. Other groups of mice treated with the CD40 agonist antibodies, CSF1R (CD115) blocking antibodies, or the combination of those two antibodies prolonged survival but still less than 25% of those mice survived to 50 days after tumor inoculation. Significantly, more than 70% of the mice treated with the mCD115-Fc-CD40L chimeric protein survived past 50 days post tumor inoculation as shown in FIG. 11B. As shown in FIG. 11C, treatment with the chimeric protein resulted in significantly higher tumor rejection than treatment with CD40 agonist antibodies, CSF1R (CD115) blocking antibodies, or a combination of the two antibodies.

Figure 12A:
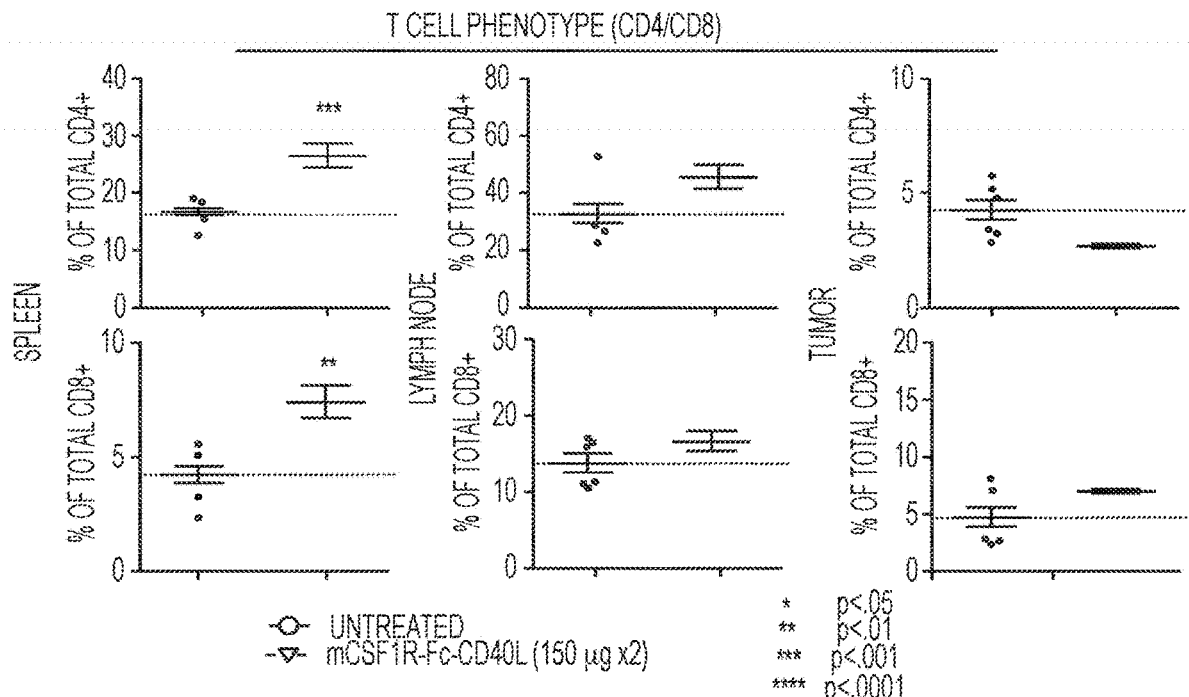
Figure 12B:
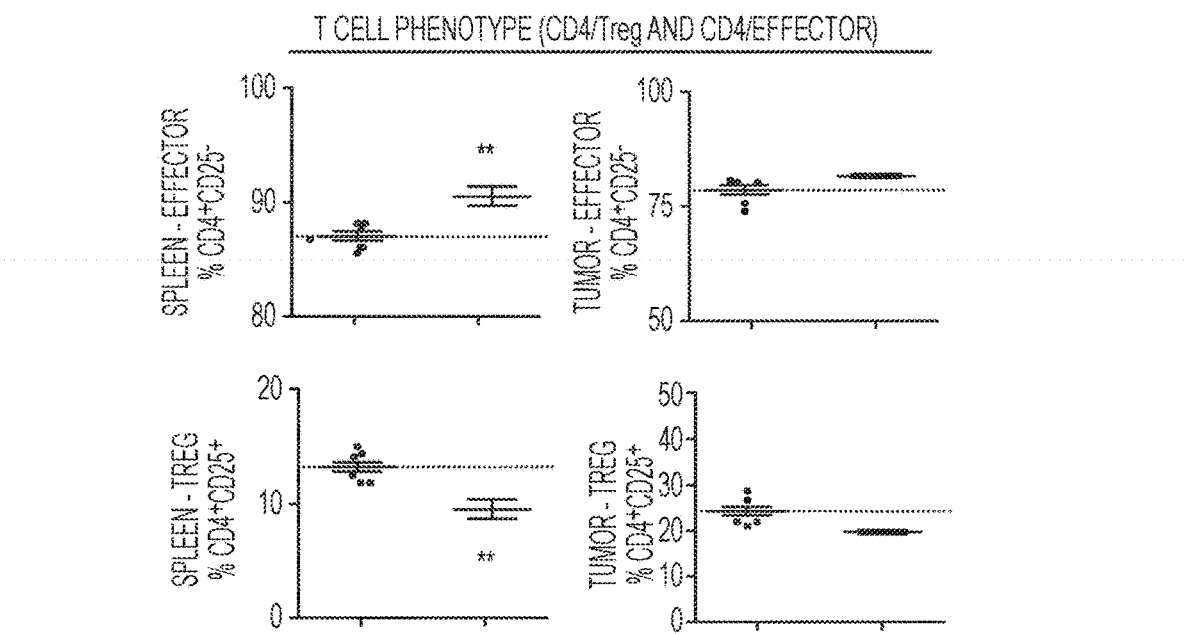

Example 12. Immunophenotyping of Lymphocyte Populations from Tumor Bearing Mice Immune phenotyping was also performed by analyzing splenocytes, lymph node cells, and tumor infiltrating lymphocytes on day 13 post tumor inoculation. As shown in FIG. 12A, mice treated with the mCD115-Fc-CD40L chimeric protein exhibited increased frequencies of both $CD4^+$ and $CD8^+$ T cells in the spleen, but not in the lymph node or tumor as compared to untreated mice. Additionally, mice treated with the chimeric protein exhibited a decrease in the proportion of $CD4^+$ $CD25^+$ cells in the spleen and tumors suggesting that the chimeric protein reduces regulatory T cells (FIG. 12B). Notably, despite a non-significant increase in the proportion of total $CD8^+$ cells within the tumor (FIG. 12A), a significant increase in the proportion of $CD8^+$ T cells specific for the AH1 tumor antigen (by tetramer staining) were detected in mice treated with mCD115-Fc-CD40L chimeric protein (FIG. 12C), suggesting the chimeric protein enhanced tumor recognition by $CD8^+$ T cells.

To assess CD40 receptor activation by the mCD115-Fc-CD40L chimeric protein, induction of $CD19^+$ cells and IL-15Rα positive cells by the chimeric protein were analyzed. As shown in FIG. 12D, a significant increase in $CD19^+$ cells was observed in the splenocytes of mice treated with the chimeric protein. This increase in $CD19^+$ cells was not observed in the lymph nodes or tumor cells. Further, there was also a significant increase in IL-15Rα positive cells in the splenocytes of mice treated with the chimeric protein (FIG. 12E). Again, the increase was not observed in the lymph nodes or tumor cells.

Figures 13A, 13B:
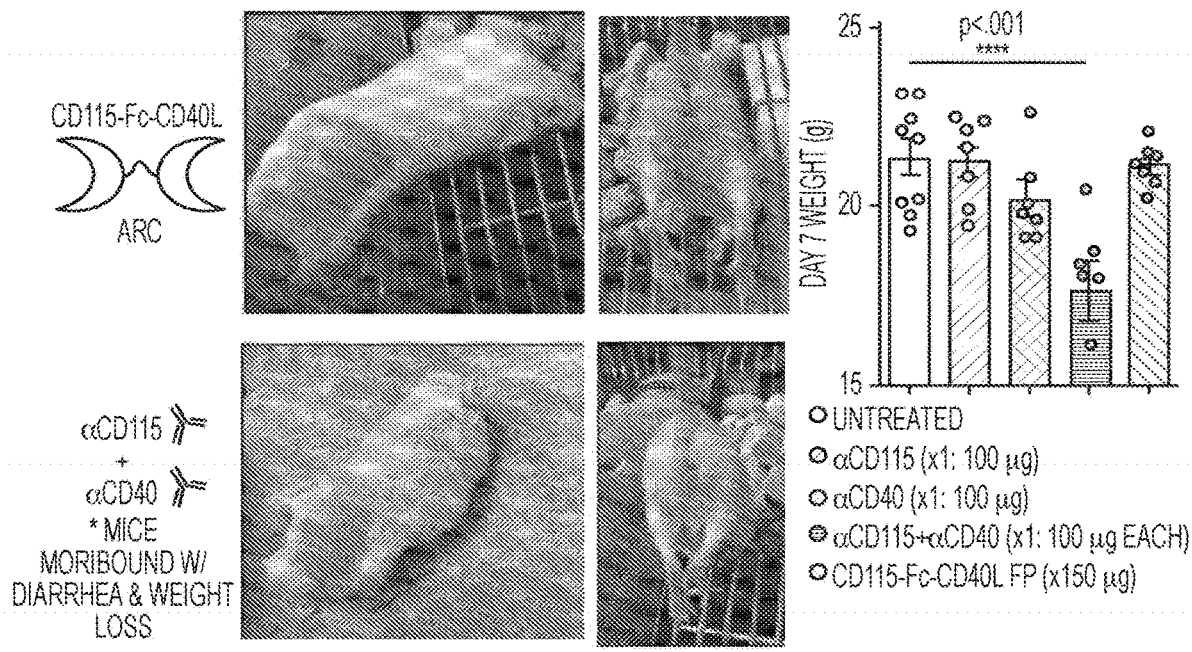
FIG. 13A and FIG. 13B show safety of murine CSF1R-Fc-CD40L versus a CD40 agonist antibody. Monotherapy with a CD40 agonist antibody (clone FGK4.5) or combination therapy with the CD40 agonist antibody and an anti-CD115(CSF1R) antibody (clone AFS98) produced significant diarrhea and weight loss in mice over the course of the experiment. These data indicate that the CD40 agonist antibody initiated a gut inflammatory response leading to diarrhea and weight loss, which was then significantly exacerbated by the combination with CD115 blockade. Mice in the antibody combination group lost >25% of their body weight (see FIG. 13B), had a moribund appearance (FIG.

Example 13. Reduced Toxicity of CSF1R-Fc-CD40L Compared to CSF1R and CD40 Antibodies The in vivo studies also surprisingly demonstrated that the mCD115-Fc-CD40L chimeric protein exhibited enhanced safety profiles. Specifically, mice treated with the CD40 agonist antibody and the $CD40^+$ CD115 antibody combination treatment were observed to develop significant diarrhea and weight loss over the course of the experiment. In mice treated with the CD40 agonist antibody, a gut inflammatory response was initiated leading to diarrhea and weight loss, which was then significantly exacerbated by combination treatment with CD115 blockade. Mice in the antibody combination ($CD115^+$ CD40 antibody) group lost >25% of their body weight (FIG. 13B), had a moribund appearance and in some cases this inflammatory response was lethal (see FIG. 13A). In contrast, mice treated with the mCD115-Fc-CD40L chimeric protein appeared healthy, did not develop any signs of diarrhea or weight loss, and behaved normally (FIG. 13A and FIG. 13B).

Altogether, these data indicate that the treatment with the mCD115-Fc-CD40L chimeric protein led to significantly higher rates of complete tumor rejection than CD115 blocking antibodies alone, CD40 agonist antibodies alone, or the combination of CD115 blocking and CD40 agonist antibodies. Further still, treatment with the chimeric protein provided enhanced safety profiles compared to treatment with the antibodies, which were highly toxic when co-administered to mice and caused lethal gut inflammation and diarrhea.

Example 14: Characterization of the Contribution of an Fc Domain in a Linker to Functionality of Chimeric Proteins In this example, the contribution of an Fc domain in a linker to functionality of chimeric proteins of the present invention was assayed. Here, a PD1-Fc-OX40L was used as a model for Fc-containing chimeric proteins. Thus, the data presented below is relevant to chimeric proteins of the present invention.

Figure 14:
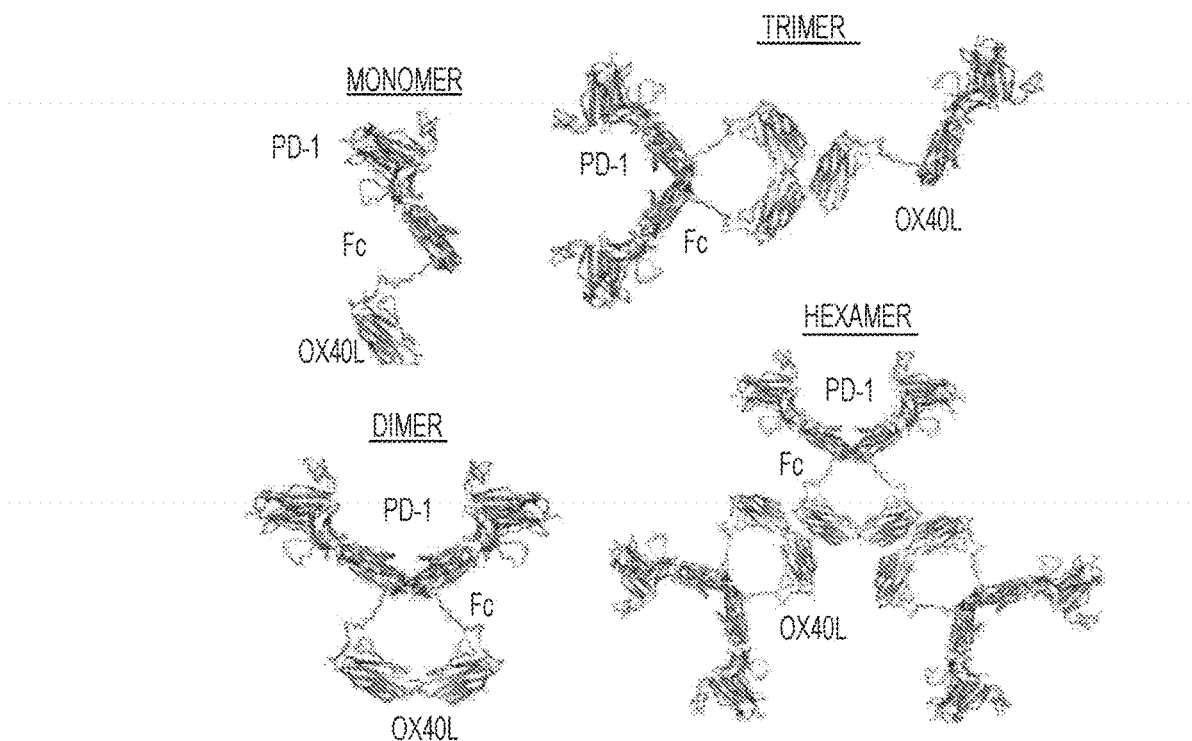
FIG. 14 shows four potential configurations of illustrative chimeric proteins (PD1-Fc-OX40L).

In its native state, PD1 exists as monomer whereas OX40Ls tend to dimerize due to electrostatic interactions between the OX40L domains; Fc domains associate with each other via disulfide bonds. Together, several intermolecular interactions may contribute to the quaternary structure of PD1-Fc-OX40L. There are, at least, four potential configurations of PD1-Fc-OX40L, with the chimeric protein existing as a monomer, a dimer, a trimer, or a hexamer. See, FIG. 14.

Figure 15:
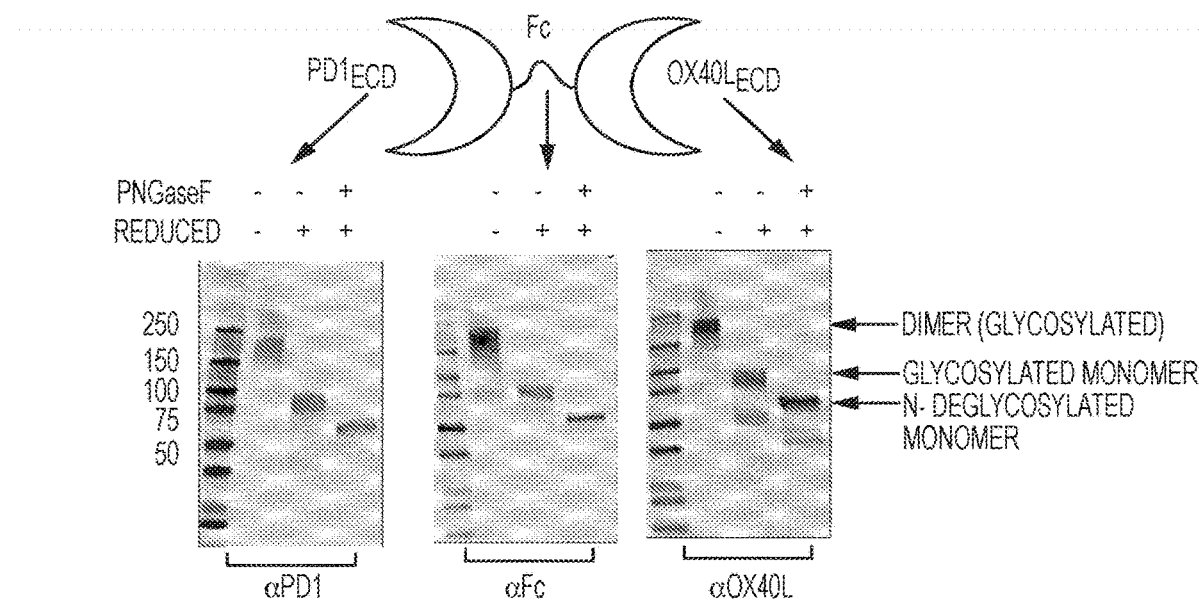
FIG. 15 shows Western blots of PD1-Fc-OX40L chimeric proteins run on SDS-PAGE under a non-reducing condition, a reducing condition, and a reducing condition and following treatment with Peptide-N-Glycosidase F (PNGaseF).

The existence of monomeric and dimeric configurations of the chimeric protein was tested by exposing chimeric proteins to reducing and non-reducing conditions and then running the proteins on SDS-PAGE. Under non-reducing conditions (Reduced: "−"), the chimeric protein migrated in SDS-PAGE at about 200 kDa. Here, Western blots were probed with antibodies directed against PD1, Fc, or OX40L in, respectively, the left, middle, and right blots shown in FIG. 15. Since, the predicted monomeric molecular weight of the chimeric protein is 57.6 kDa, the 200 kDa species was expected to be, at least a dimer. However, under reduced conditions (Reduced: "+"), which reduces disulfide bonds (e.g., between Fc domains), the chimeric protein migrated in SDS-PAGE at about 100 kDa. Since the 100 kDa species was heavier than expected, it was predicted that the extra mass was due to glycosylation. Finally, chimeric proteins were treated with Peptide-N-Glycosidase F (PNGaseF "+") and run on SDS-PAGE under reduced conditions. Under these conditions, the chimeric protein migrated at about 57.6 kDa. These data suggest that the chimeric protein is glycosylated and exists naturally, at least, as a dimer; with dimerization likely due to disulfide bonding between Fc domains.

Figure 16:
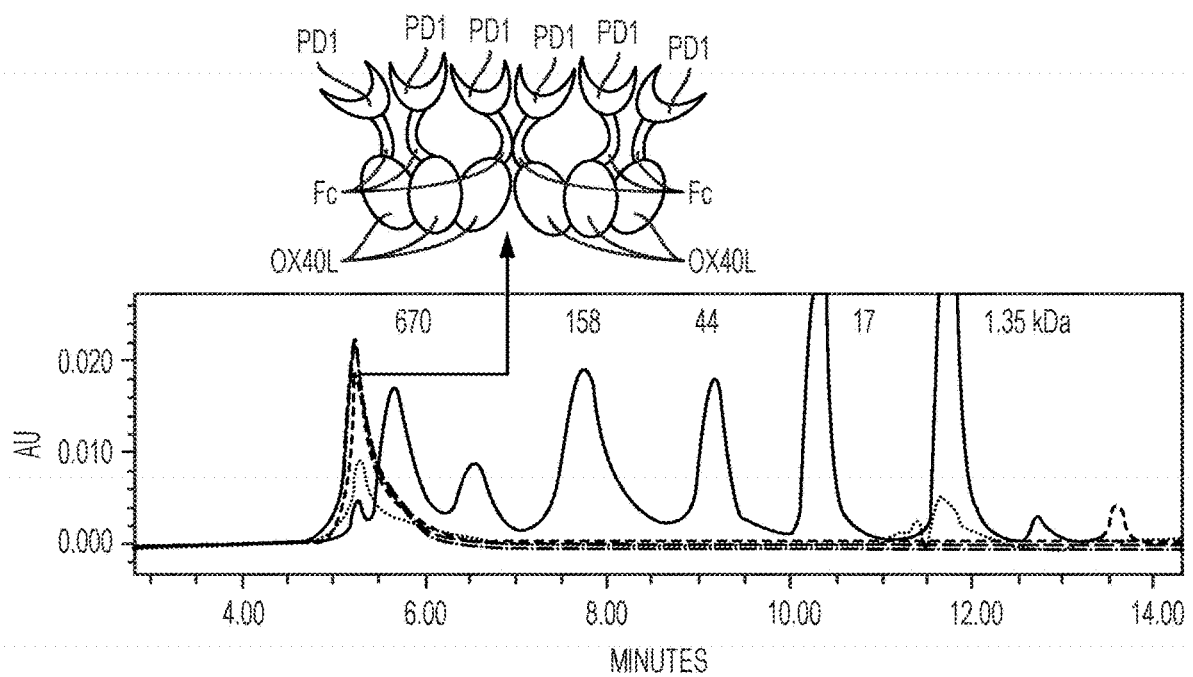
FIG. 16 shows a chromatograph for PD1-Fc-OX40L chimeric proteins run on Size Exclusion Chromatography (SEC).

SDS-PAGE gel methods do not accurately predict the molecular weight for highly charged and/or large molecular weight proteins. Thus, chimeric proteins were next characterized using Size Exclusion Chromatography (SEC). Unlike SDS-PAGE, in which the negatively-charged SDS reduces charge-based interactions between peptides, SEC does not use detergents or reducing agents. When the PD1-Fc-OX40L chimeric protein was run on SEC, none of the peaks were around 200 kDa. This suggests, that natively, the chimeric protein does not exist as a dimer. Instead, a peak having a size greater than 670 kDa was detected. See, FIG. 16. This and the prior data suggests that the PD1-Fc-OX40L chimeric protein exists as a hexamer in its native state.

Figure 17:
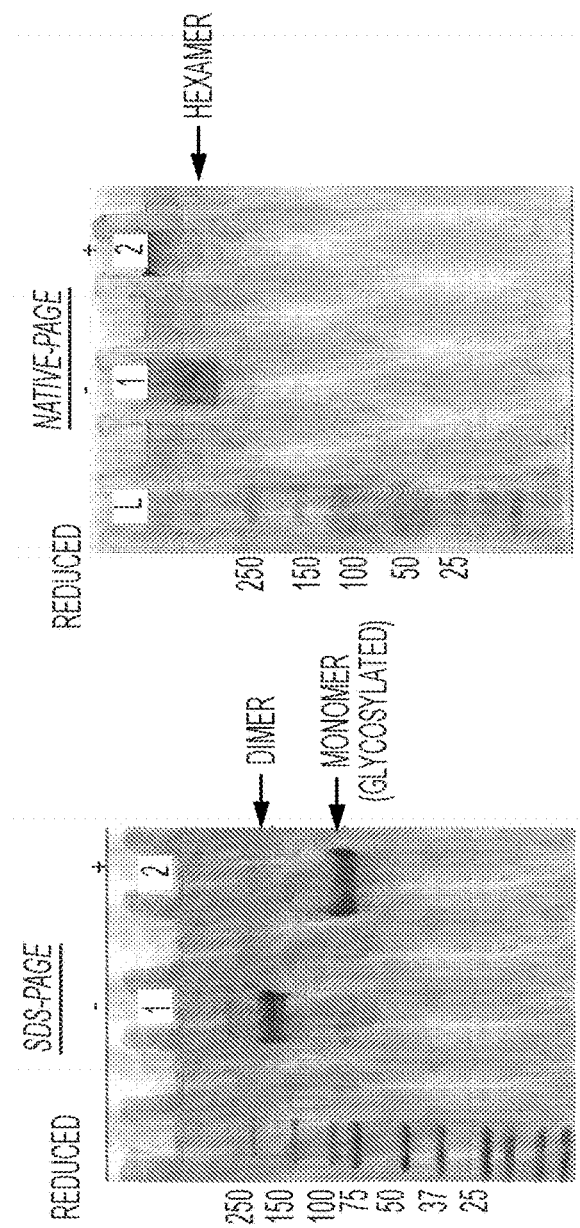
FIG. 17 shows SDS-PAGE and native (non-SDS) PAGE gels for PD1-Fc-OX40L chimeric proteins run under a non-reducing condition ("−") or under a reducing condition ("+").

As shown above, when run on SDS-PAGE under non-reducing conditions or under reducing conditions, SDS in the sample and/or running buffer converts the hexameric PD1-Fc-OX40L chimeric protein into a predominant dimer or monomer, respectively, in the absence and presence of a reducing agent. See, FIG. 17 (left gel). When run on native PAGE, which lacks SDS, and in the absence of a reducing agent, the chimeric protein exists as a hexamer. However, when run on native PAGE and in the presence of a reducing agent (which reduces disulfide bonds) the chimeric protein migrated heavier than expected; as shown in FIG. 17 (right gel, lane #2), with the chimeric protein failed to substantially migrate out of the loading well. This data suggests that the chimeric protein has oligomerized into a higher order protein. Thus, in chimeric proteins, disulfide bonding appears to be important for controlling higher-order oligomerization.

Figure 18:
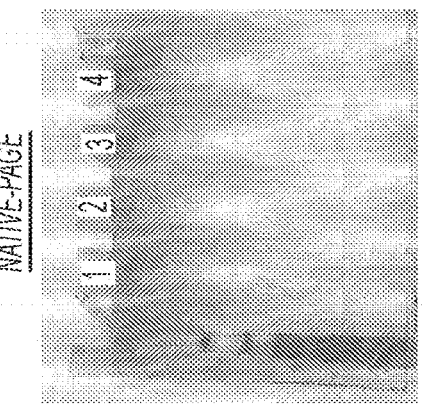
FIG. 18 shows a native (non-SDS) PAGE gel for PD1-No Fc-OX40L chimeric proteins which lack an Fc domain in a linker.

To further confirm this, chimeric proteins lacking an Fc domain were constructed, e.g., "PD1-No Fc-OX40L". Such chimeric proteins will not have the disulfide bonding which occurs between Fc domains in the chimeric proteins described previously. As shown in FIG. 18, when chimeric proteins lacking Fc domains are run on native PAGE, none of the protein substantially migrated out of its loading well (lane #1 to #4 show increasing loading concentrations of PD1-No Fc-OX40L); again, suggesting that the "No Fc" chimeric proteins have formed a concatamer-like complex comprising numerous proteins. Thus, omission of the Fc domain in a chimeric protein leads to formation of protein aggregates. These data indicate that disulfide bonding, e.g., between Fc domains on different chimeric proteins, stabilizes the chimeric proteins and ensures that they each exist as a hexamer and not as a higher order protein/concatemer. In other words, the Fc domain surprisingly puts order to chimeric protein complexes. Lane #1 to #4, respectively, include 2.5 pg, of PD1-No Fc-OX40L, 5 μg of PD1-No Fc-OX40L, 7.5 μg of PD1-No Fc-OX40L, and 10 μg of PD1-No Fc-OX40L.

Figure 19:
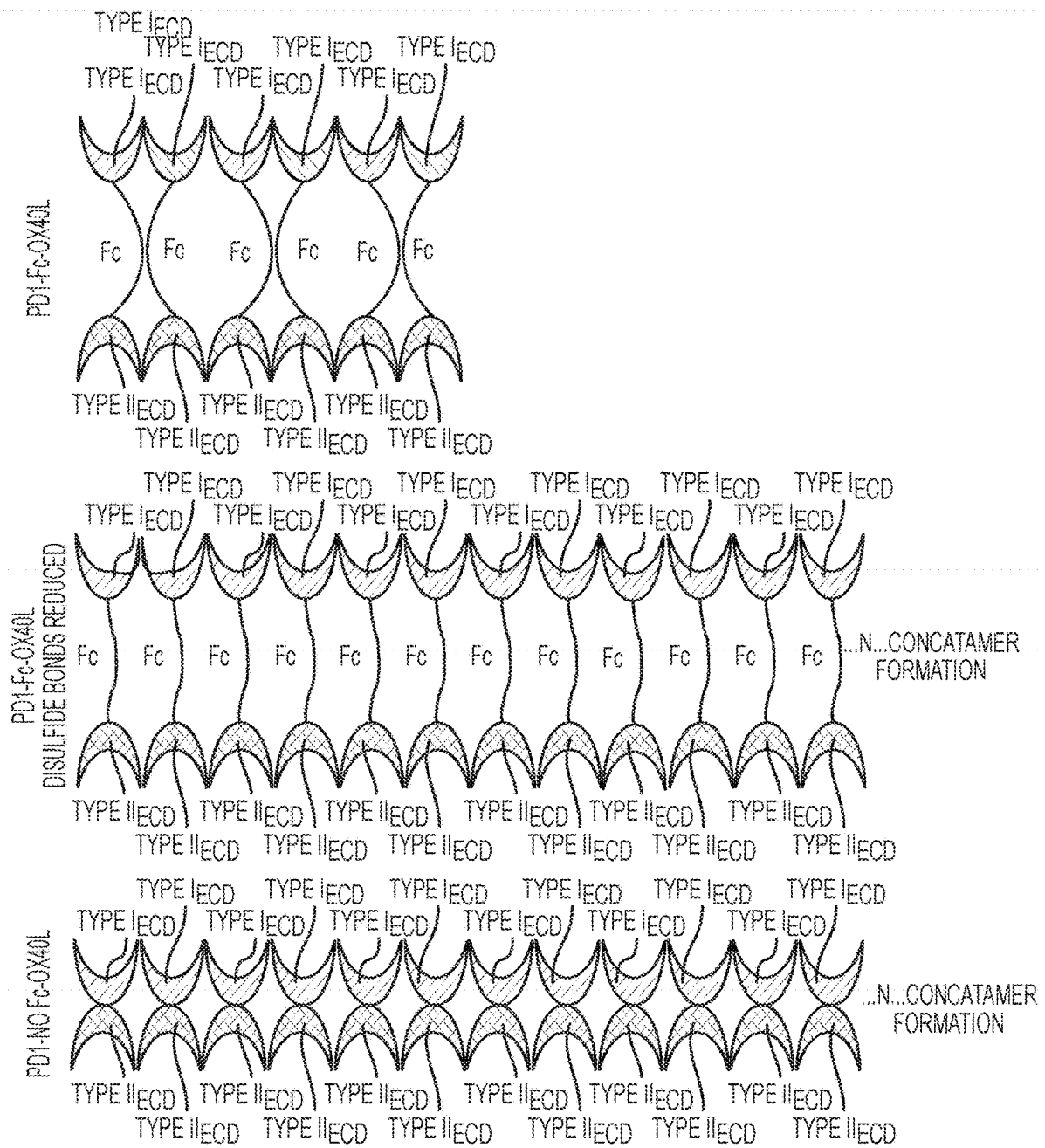
FIG. 19 shows, without wishing to be bound by theory, a model for how a hexamer and concatamers form from chimeric proteins of the present invention.

Shown in FIG. 19, is a model summarizing the above data and showing how a hexamer and concatamers form from chimeric proteins of the present invention. The exemplary chimeric protein (PD1-Fc-OX40L) naturally forms into a hexamer (due to electrostatic interactions between the OX40L domains and dimerization by Fc domains). However, in the absence of the controlling effects of disulfide bonding between Fc domains, under reduced conditions for the PD1-Fc-OX40L protein and due to the absence of Fc domains in the PD1-No Fc-OX40L, these latter chimeric proteins form concatamers.

Additionally, chimeric proteins were constructed in which the Fc domain (as described herein) was replaced with Ficolin (which lacks cysteine residues necessary for disulfide bonding between chimeric proteins). As with the "No Fc" chimeric proteins and chimeric proteins comprising an Fc and run on native PAGE and in the presence of a reducing agent (both of which formed aggregates that do not migrate into a gel), chimeric proteins comprising Ficolin appear to also form higher-order lattices which did not migrate into a gel. These data reinforce the conclusion that disulfide binding is important for proper folding and function of chimeric proteins of the present invention.

Finally, chimeric proteins were prepared using coiled Fc domains (CCDFc). Very little purified protein was delivered under functional evaluation.

Accordingly, including an Fc domain in a linker of a chimeric protein (which is capable of forming disulfide bonds between chimeric proteins), helps avoid formation of insoluble and, likely, non-functional protein concatamers and/or aggregates.

Example 15: Production of Additional CSF1R-Containing Chimeric Proteins Comprising Extracellular Domains of Other Type II Proteins In this example, additional chimeric proteins of the present invention are described. Such additional chimeric proteins will be made similar to how the CSF1R-Fc-CD40L chimeric proteins were made, e.g., as described above in the Detailed Description and in U.S. 62/464,002, the contents of which are hereby incorporated by reference in its entirety.

These additional chimeric proteins will have the general formula: ECD 1—Joining Linker 1—Fc Domain—Joining Linker 2—ECD 2, in which ECD 1 is the extracellular domain of CSF1R and ECD 2 is the extracellular domain of a type II protein, other than CD40L. Exemplary type II proteins include 4-1BBL, CD30L, FasL, GITRL, LIGHT, OX40L, TL1A, and TRAIL. These chimeric proteins may lack one or both of the joining linkers.

These chimeric proteins may lack one or both of the joining linkers. Exemplary Joining Linker 1s, Fc Domains, and Joining Linker 2s are described above in Table 1; modular linkers useful for forming chimeric proteins and comprising specific Joining Linker 1s, Fc Domains, and Joining Linker 2s are shown in FIG. 20.

Alternately, the additional chimeric proteins will be fusion proteins having the general formula: N terminus-(a)-(b)-(c)-C terminus, in which (a) is CSF1R, (b) is a linker comprising at least a portion of an Fc domain, and (c) is the extracellular domain of a type II protein other than CD40L. Exemplary type II proteins include 4-1BBL, CD30L, FasL, GITRL, LIGHT, OX40L, TL1A, and TRAIL.

The amino acid sequence for 4-1BBL, CD30L, FasL, GITRL, LIGHT, OX40L, TL1A, and TRAIL, respectively, comprises SEQ ID NO: 9, 11, 13, 15, 17, 6, 21, and 23. The amino acid sequence for extracellular domain of 4-1BBL, CD30L, FasL, GITRL, LIGHT, OX40L, TL1A, and TRAIL, respectively, comprises SEQ ID NO: 10, 12, 14, 16, 18, 7, 22, and 24. The amino acid sequence for CSF1R comprises SEQ ID NO: 1 and the extracellular domain of CSF1R comprises SEQ ID NO: 2. The chimeric proteins may comprise a variant of the above-mentioned sequences, e.g., at least about 95% identical to an above-mentioned sequence.

Exemplary linkers are described above in Table 1; modular linkers useful for forming chimeric proteins and comprising specific Joining Linker 1s, Fc Domains, and Joining Linker 2s are shown in FIG. 20.

Accordingly, the present invention further includes the following additional chimeric proteins and methods using the additional chimeric proteins (e.g., in treating a cancer and/or treating an inflammatory disease): CSF1R-Fc-4-1BBL, CSF1R-Fc-CD30L, CSF1R-Fc-FasL, CSF1R-Fc-GITRL, CSF1R-Fc-LIGHT, CSF1R-Fc-OX40L, CSF1R-Fc-TL1A, and CSF1R-Fc-TRAIL.

The additional chimeric proteins will be characterized as described above for CSF1R-Fc-CD40L in Examples 1 to 13, albeit with reagents (e.g., binding partners, recombinant target cells, and cancer cell/tumor types) that are specific to the additional chimeric proteins rather than as needed for characterizing CSF1R-Fc-CD40L. Thus, using CSF1R-Fc-4-1BBL as an example, characterizations of CSF1R-Fc-4-1BBL akin to Example 2 can be performed using anti-CSF1R, anti-Fc, and anti-4-1BBL antibodies rather than the anti-CSF1R, anti-Fc, and anti-CD40L antibodies needed for CSF1R-Fc-CD40L.

As with the CSF1R-Fc-CD40L chimeric proteins, the additional chimeric proteins will be effective in treating a cancer and/or treating an inflammatory disease by blocking CSF1R (which inhibits the transmission of an immune inhibitory signal) and enhancing, increasing, and/or stimulating the transmission of an immune stimulatory signal via activating the receptor/ligand of one of 4-1BBL, CD30L, FasL, GITRL, LIGHT, OX40L, TL1A, and TRAIL. Moreover, the additional chimeric proteins will be effective in treating a cancer and/or an inflammatory disease yet without the toxicity resulting from treatments comprising a plurality of antibodies, e.g., a CSF1 or IL-34 blocking antibody and an agonist antibody for the receptor/ligand of one of 4-1BBL, CD30L, FasL, GITRL, LIGHT, OX40L, TL1A, and TRAIL.

What is claimed is:

1. A heterologous chimeric protein comprising:
   (a) a first domain comprising a portion of colony stimulating factor 1 receptor (CSF1R) that is at least 95% identical to the amino acid sequence of SEQ ID NO: 1 or SEQ ID NO: 2;
   (b) a second domain comprising a portion of CD40 Ligand (CD40L) that is at least 95% identical to the amino acid sequence of SEQ ID NO: 3 or SEQ ID NO: 4; and
   (c) a linker linking the first domain and the second domain, the linker comprising a hinge-CH2-CH3 Fc domain.

2. The heterologous chimeric protein of claim 1, wherein the first domain comprises substantially all of the extracellular domain of CSF1R and the second domain comprises substantially all of the extracellular domain of CD40L.

3. The heterologous chimeric protein of claim 1, wherein the chimeric protein is capable of:
   (a) reducing or eliminating an immune inhibitory signal when the portion of CSF1R is bound to its ligand and/or
   (b) increasing or activating an immune stimulatory signal when the portion of CD40L is bound to its receptor.

4. The heterologous chimeric protein of claim 1, wherein the chimeric protein is capable of contemporaneously binding the CSF1R ligand and the CD40L receptor, wherein the CSF1R ligand is CSF1 or IL-34 and the CD40L receptor is CD40.

5. The heterologous chimeric protein of claim 1, wherein the chimeric protein exhibits enhanced anti-tumor effects compared to CD40 agonist antibodies and/or CSF1R antagonistic antibodies.

6. The heterologous chimeric protein of claim 1, wherein the chimeric protein is capable of increasing or preventing a decrease in a sub-population of CD4+ and/or CD8+ T cells.

7. The heterologous chimeric protein of claim 1, wherein the chimeric protein is capable of enhancing tumor killing activity by T cells.

8. The heterologous chimeric protein of claim 1, wherein the chimeric protein is capable of providing a sustained immunomodulatory effect.

9. The heterologous chimeric protein of claim 1, wherein the chimeric protein is capable of causing activation of antigen presenting cells.

10. The heterologous chimeric protein of claim 1, wherein the linker comprises hinge-CH2-CH3 Fc domain derived from IgG4.

11. The heterologous chimeric protein of claim 10, wherein the hinge-CH2-CH3 Fc domain is derived from human IgG4.

12. The heterologous chimeric protein of claim 1, wherein the chimeric protein is expressed by a mammalian host cell as a secretable and functional single polypeptide chain.

13. The heterologous chimeric protein of claim 1, wherein the linker comprises an amino acid sequence that is at least 95% identical to the amino acid sequence of SEQ ID NO: 25, SEQ ID NO: 26, or SEQ ID NO: 27.

14. An expression vector, comprising a nucleic acid encoding the heterologous chimeric protein of claim 1.

15. A host cell, comprising the expression vector of claim 14.

16. A pharmaceutical composition, comprising a therapeutically effective amount of the heterologous chimeric protein of claim 1.

17. A recombinant fusion protein comprising:
   (a) a first domain comprising a portion of CSF1R that is at least 95% identical to the amino acid sequence of SEQ ID NO: 1 or SEQ ID NO: 2 and is capable of binding a CSF1R ligand,
   (b) a second domain comprising a portion of CD40 ligand (CD40L) that is at least 95% identical to the amino acid sequence of SEQ ID NO: 3 or SEQ ID NO: 4 and is capable of binding a CD40L receptor, and
   (c) a linker comprising an amino acid sequence that is at least 95% identical to SEQ ID NO: 25, SEQ ID NO: 26, or SEQ ID NO: 27 and which links the first domain and the second domain.

18. A heterologous chimeric protein comprising:
   (a) a first domain comprising the amino acid sequence of SEQ ID NO: 1 or SEQ ID NO: 2,
   (b) a second domain comprising the amino acid sequence of SEQ ID NO: 3 or SEQ ID NO: 4, and
   (c) a linker linking the first domain and the second domain and comprising the amino acid sequence of SEQ ID NO: 25, SEQ ID NO: 26, or SEQ ID NO: 27.

\* \* \* \* \*

SEQUENCE LISTING

```
<160> NUMBER OF SEQ ID NOS: 80

<210> SEQ ID NO 1
<211> LENGTH: 953
<212> TYPE: PRT
<213> ORGANISM: Artificial Sequence
<220> FEATURE:
<223> OTHER INFORMATION: Synthetic Polypeptide

<400> SEQUENCE: 1

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
    195                 200                 205
```

```
Ser Val Asp Val Asn Phe Asp Val Phe Leu Gln His Asn Asn Thr Lys
210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365

Gly Trp Arg Ala Leu Thr Phe Glu Leu Thr Leu Arg Tyr Pro Pro Glu
370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
        435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                485                 490                 495

Thr Pro Val Val Val Ala Cys Met Ser Ile Met Ala Leu Leu Leu Leu
            500                 505                 510

Leu Leu Leu Leu Leu Leu Tyr Lys Tyr Lys Gln Lys Pro Lys Tyr Gln
        515                 520                 525

Val Arg Trp Lys Ile Ile Glu Ser Tyr Glu Gly Asn Ser Tyr Thr Phe
530                 535                 540

Ile Asp Pro Thr Gln Leu Pro Tyr Asn Glu Lys Trp Glu Phe Pro Arg
545                 550                 555                 560

Asn Asn Leu Gln Phe Gly Lys Thr Leu Gly Ala Gly Ala Phe Gly Lys
                565                 570                 575

Val Val Glu Ala Thr Ala Phe Gly Leu Gly Lys Glu Asp Ala Val Leu
            580                 585                 590

Lys Val Ala Val Lys Met Leu Lys Ser Thr Ala His Ala Asp Glu Lys
        595                 600                 605

Glu Ala Leu Met Ser Glu Leu Lys Ile Met Ser His Leu Gly Gln His
610                 615                 620
```

-continued

Glu Asn Ile Val Asn Leu Leu Gly Ala Cys Thr His Gly Gly Pro Val
625                 630                 635                 640

Leu Val Ile Thr Glu Tyr Cys Cys Tyr Gly Asp Leu Leu Asn Phe Leu
            645                 650                 655

Arg Arg Lys Ala Glu Ala Met Leu Gly Pro Ser Leu Ser Pro Gly Gln
        660                 665                 670

Asp Pro Glu Gly Gly Val Asp Tyr Lys Asn Ile His Leu Glu Lys Lys
    675                 680                 685

Tyr Val Arg Arg Asp Ser Gly Phe Ser Ser Gln Gly Val Asp Thr Tyr
690                 695                 700

Val Glu Met Arg Pro Val Ser Thr Ser Ser Asn Asp Ser Phe Ser Glu
705                 710                 715                 720

Gln Asp Leu Asp Lys Glu Asp Gly Arg Pro Leu Glu Leu Arg Asp Leu
            725                 730                 735

Leu His Phe Ser Ser Gln Val Ala Gln Gly Met Ala Phe Leu Ala Ser
        740                 745                 750

Lys Asn Cys Ile His Arg Asp Val Ala Ala Arg Asn Val Leu Leu Thr
    755                 760                 765

Asn Gly His Val Ala Lys Ile Gly Asp Phe Gly Leu Ala Arg Asp Ile
770                 775                 780

Met Asn Asp Ser Asn Tyr Ile Val Lys Gly Asn Ala Arg Leu Pro Val
785                 790                 795                 800

Lys Trp Met Ala Pro Glu Ser Ile Phe Asp Cys Val Tyr Thr Val Gln
            805                 810                 815

Ser Asp Val Trp Ser Tyr Gly Ile Leu Leu Trp Glu Ile Phe Ser Leu
        820                 825                 830

Gly Leu Asn Pro Tyr Pro Gly Ile Leu Val Asn Ser Lys Phe Tyr Lys
    835                 840                 845

Leu Val Lys Asp Gly Tyr Gln Met Ala Gln Pro Ala Phe Ala Pro Lys
850                 855                 860

Asn Ile Tyr Ser Ile Met Gln Ala Cys Trp Ala Leu Glu Pro Thr His
865                 870                 875                 880

Arg Pro Thr Phe Gln Gln Ile Cys Ser Phe Leu Gln Glu Gln Ala Gln
            885                 890                 895

Glu Asp Arg Arg Glu Arg Asp Tyr Thr Asn Leu Pro Ser Ser Ser Arg
        900                 905                 910

Ser Gly Gly Ser Gly Ser Ser Ser Glu Leu Glu Glu Ser Ser
    915                 920                 925

Ser Glu His Leu Thr Cys Cys Glu Gln Gly Asp Ile Ala Gln Pro Leu
930                 935                 940

Leu Gln Pro Asn Asn Tyr Gln Phe Cys
945                 950

<210> SEQ ID NO 2
<211> LENGTH: 498
<212> TYPE: PRT
<213> ORGANISM: Artificial Sequence
<220> FEATURE:
<223> OTHER INFORMATION: Synthetic Polypeptide

<400> SEQUENCE: 2

Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

```
Gly Pro Pro Ser Pro His Trp Thr Leu Tyr Ser Asp Gly Ser Ser Ser
             35                  40                  45

Ile Leu Ser Thr Asn Asn Ala Thr Phe Gln Asn Thr Gly Thr Tyr Arg
 50                  55                  60

Cys Thr Glu Pro Gly Asp Pro Leu Gly Gly Ser Ala Ala Ile His Leu
 65                  70                  75                  80

Tyr Val Lys Asp Pro Ala Arg Pro Trp Asn Val Leu Ala Gln Glu Val
                 85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
            210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
            290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
            370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
```

```
                450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                485                 490                 495

Thr Pro

<210> SEQ ID NO 3
<211> LENGTH: 261
<212> TYPE: PRT
<213> ORGANISM: Artificial Sequence
<220> FEATURE:
<223> OTHER INFORMATION: Synthetic Polypeptide

<400> SEQUENCE: 3

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
                100                 105                 110

Met Gln Lys Gly Asp Gln Asn Pro Gln Ile Ala Ala His Val Ile Ser
            115                 120                 125

Glu Ala Ser Ser Lys Thr Thr Ser Val Leu Gln Trp Ala Glu Lys Gly
        130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
                180                 185                 190

Leu Cys Leu Lys Ser Pro Gly Arg Phe Glu Arg Ile Leu Leu Arg Ala
            195                 200                 205

Ala Asn Thr His Ser Ser Ala Lys Pro Cys Gly Gln Gln Ser Ile His
        210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 4
<211> LENGTH: 215
<212> TYPE: PRT
<213> ORGANISM: Artificial Sequence
<220> FEATURE:
<223> OTHER INFORMATION: Synthetic Polypeptide
```

<400> SEQUENCE: 4

```
His Arg Arg Leu Asp Lys Ile Glu Asp Glu Arg Asn Leu His Glu Asp
1               5                   10                  15

Phe Val Phe Met Lys Thr Ile Gln Arg Cys Asn Thr Gly Glu Arg Ser
            20                  25                  30

Leu Ser Leu Leu Asn Cys Glu Glu Ile Lys Ser Gln Phe Glu Gly Phe
        35                  40                  45

Val Lys Asp Ile Met Leu Asn Lys Glu Thr Lys Lys Glu Asn Ser
    50                  55                  60

Phe Glu Met Gln Lys Gly Asp Gln Asn Pro Gln Ile Ala Ala His Val
65                  70                  75                  80

Ile Ser Glu Ala Ser Ser Lys Thr Thr Ser Val Leu Gln Trp Ala Glu
                85                  90                  95

Lys Gly Tyr Tyr Thr Met Ser Asn Asn Leu Val Thr Leu Glu Asn Gly
            100                 105                 110

Lys Gln Leu Thr Val Lys Arg Gln Gly Leu Tyr Tyr Ile Tyr Ala Gln
        115                 120                 125

Val Thr Phe Cys Ser Asn Arg Glu Ala Ser Ser Gln Ala Pro Phe Ile
    130                 135                 140

Ala Ser Leu Cys Leu Lys Ser Pro Gly Arg Phe Glu Arg Ile Leu Leu
145                 150                 155                 160

Arg Ala Ala Asn Thr His Ser Ser Ala Lys Pro Cys Gly Gln Gln Ser
                165                 170                 175

Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
        195                 200                 205

Ser Phe Gly Leu Leu Lys Leu
    210                 215
```

<210> SEQ ID NO 5
<211> LENGTH: 947
<212> TYPE: PRT
<213> ORGANISM: Artificial Sequence
<220> FEATURE:
<223> OTHER INFORMATION: Synthetic Polypeptide

<400> SEQUENCE: 5

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
            20                  25                  30

Gly Pro Pro Ser Pro His Trp Thr Leu Tyr Ser Asp Gly Ser Ser Ser
        35                  40                  45

Ile Leu Ser Thr Asn Asn Ala Thr Phe Gln Asn Thr Gly Thr Tyr Arg
    50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
            100                 105                 110

Pro Val Leu Glu Ala Gly Val Ser Leu Val Arg Val Arg Gly Arg Pro
        115                 120                 125

Leu Met Arg His Thr Asn Tyr Ser Phe Ser Pro Trp His Gly Phe Thr
```

```
                130               135                140
Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
            165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
            195                 200                 205

Ser Val Asp Val Asn Phe Asp Val Phe Leu Gln His Asn Asn Thr Lys
            210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
            245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
            275                 280                 285

Asn Leu Ile Gln Glu Val Thr Val Gly Glu Gly Leu Asn Leu Lys Val
            290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
            325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
            355                 360                 365

Gly Trp Arg Ala Leu Thr Phe Glu Leu Thr Leu Arg Tyr Pro Pro Glu
            370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
            405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
            450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
            485                 490                 495

Thr Pro Ser Lys Tyr Gly Pro Pro Cys Pro Pro Cys Pro Ala Pro Glu
            500                 505                 510

Phe Leu Gly Gly Pro Ser Val Phe Leu Phe Pro Pro Lys Pro Lys Asp
            515                 520                 525

Gln Leu Met Ile Ser Arg Thr Pro Glu Val Thr Cys Val Val Val Asp
            530                 535                 540

Val Ser Gln Glu Asp Pro Glu Val Gln Phe Asn Trp Tyr Val Asp Gly
545                 550                 555                 560
```

```
Val Glu Val His Asn Ala Lys Thr Lys Pro Arg Glu Gln Phe Asn
            565                 570                 575

Ser Thr Tyr Arg Val Val Ser Val Leu Thr Val Leu His Gln Asp Trp
        580                 585                 590

Leu Ser Gly Lys Glu Tyr Lys Cys Lys Val Ser Ser Lys Gly Leu Pro
        595                 600                 605

Ser Ser Ile Glu Lys Thr Ile Ser Asn Ala Thr Gly Gln Pro Arg Glu
        610                 615                 620

Pro Gln Val Tyr Thr Leu Pro Pro Ser Gln Glu Met Thr Lys Asn
625                 630                 635                 640

Gln Val Ser Leu Thr Cys Leu Val Lys Gly Phe Tyr Pro Ser Asp Ile
                645                 650                 655

Ala Val Glu Trp Glu Ser Asn Gly Gln Pro Glu Asn Asn Tyr Lys Thr
            660                 665                 670

Thr Pro Pro Val Leu Asp Ser Asp Gly Ser Phe Phe Leu Tyr Ser Arg
        675                 680                 685

Leu Thr Val Asp Lys Ser Arg Trp Gln Glu Gly Asn Val Phe Ser Cys
        690                 695                 700

Ser Val Leu His Glu Ala Leu His Asn His Tyr Thr Gln Lys Ser Leu
705                 710                 715                 720

Ser Leu Ser Leu Gly Lys Ile Glu Gly Arg Met Asp His Arg Arg Leu
                725                 730                 735

Asp Lys Ile Glu Asp Glu Arg Asn Leu His Glu Asp Phe Val Phe Met
            740                 745                 750

Lys Thr Ile Gln Arg Cys Asn Thr Gly Glu Arg Ser Leu Ser Leu Leu
        755                 760                 765

Asn Cys Glu Glu Ile Lys Ser Gln Phe Glu Gly Phe Val Lys Asp Ile
        770                 775                 780

Met Leu Asn Lys Glu Glu Thr Lys Lys Glu Asn Ser Phe Glu Met Gln
785                 790                 795                 800

Lys Gly Asp Gln Asn Pro Gln Ile Ala Ala His Val Ile Ser Glu Ala
                805                 810                 815

Ser Ser Lys Thr Thr Ser Val Leu Gln Trp Ala Glu Lys Gly Tyr Tyr
            820                 825                 830

Thr Met Ser Asn Asn Leu Val Thr Leu Glu Asn Gly Lys Gln Leu Thr
        835                 840                 845

Val Lys Arg Gln Gly Leu Tyr Tyr Ile Tyr Ala Gln Val Thr Phe Cys
850                 855                 860

Ser Asn Arg Glu Ala Ser Ser Gln Ala Pro Phe Ile Ala Ser Leu Cys
865                 870                 875                 880

Leu Lys Ser Pro Gly Arg Phe Glu Arg Ile Leu Leu Arg Ala Ala Asn
                885                 890                 895

Thr His Ser Ser Ala Lys Pro Cys Gly Gln Gln Ser Ile His Leu Gly
            900                 905                 910

Gly Val Phe Glu Leu Gln Pro Gly Ala Ser Val Phe Val Asn Val Thr
        915                 920                 925

Asp Pro Ser Gln Val Ser His Gly Thr Gly Phe Thr Ser Phe Gly Leu
        930                 935                 940

Leu Lys Leu
945

<210> SEQ ID NO 6
<211> LENGTH: 183
```

```
<212> TYPE: PRT
<213> ORGANISM: Artificial Sequence
<220> FEATURE:
<223> OTHER INFORMATION: Synthetic Polypeptide

<400> SEQUENCE: 6

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 7
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 7

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Asn Gly Gly Glu Leu Ile Leu Ile His Gln Asn Pro Gly
        115                 120                 125

Glu Phe Cys Val Leu
    130
```

<210> SEQ ID NO 8
<211> LENGTH: 865
<212> TYPE: PRT
<213> ORGANISM: Artificial Sequence
<220> FEATURE:
<223> OTHER INFORMATION: Synthetic Polypeptide

<400> SEQUENCE: 8

```
Ile Pro Val Ile Glu Pro Ser Val Pro Glu Leu Val Val Lys Pro Gly
1               5                   10                  15

Ala Thr Val Thr Leu Arg Cys Val Gly Asn Gly Ser Val Glu Trp Asp
                20                  25                  30

Gly Pro Pro Ser Pro His Trp Thr Leu Tyr Ser Asp Gly Ser Ser Ser
            35                  40                  45

Ile Leu Ser Thr Asn Asn Ala Thr Phe Gln Asn Thr Gly Thr Tyr Arg
        50                  55                  60

Cys Thr Glu Pro Gly Asp Pro Leu Gly Gly Ser Ala Ala Ile His Leu
65                  70                  75                  80

Tyr Val Lys Asp Pro Ala Arg Pro Trp Asn Val Leu Ala Gln Glu Val
                85                  90                  95

Val Val Phe Glu Asp Gln Asp Ala Leu Leu Pro Cys Leu Leu Thr Asp
                100                 105                 110

Pro Val Leu Glu Ala Gly Val Ser Leu Val Arg Val Arg Gly Arg Pro
            115                 120                 125

Leu Met Arg His Thr Asn Tyr Ser Phe Ser Pro Trp His Gly Phe Thr
    130                 135                 140

Ile His Arg Ala Lys Phe Ile Gln Ser Gln Asp Tyr Gln Cys Ser Ala
145                 150                 155                 160

Leu Met Gly Gly Arg Lys Val Met Ser Ile Ser Ile Arg Leu Lys Val
                165                 170                 175

Gln Lys Val Ile Pro Gly Pro Pro Ala Leu Thr Leu Val Pro Ala Glu
            180                 185                 190

Leu Val Arg Ile Arg Gly Glu Ala Ala Gln Ile Val Cys Ser Ala Ser
        195                 200                 205

Ser Val Asp Val Asn Phe Asp Val Phe Leu Gln His Asn Asn Thr Lys
    210                 215                 220

Leu Ala Ile Pro Gln Gln Ser Asp Phe His Asn Asn Arg Tyr Gln Lys
225                 230                 235                 240

Val Leu Thr Leu Asn Leu Asp Gln Val Asp Phe Gln His Ala Gly Asn
                245                 250                 255

Tyr Ser Cys Val Ala Ser Asn Val Gln Gly Lys His Ser Thr Ser Met
            260                 265                 270

Phe Phe Arg Val Val Glu Ser Ala Tyr Leu Asn Leu Ser Ser Glu Gln
        275                 280                 285

Asn Leu Ile Gln Glu Val Thr Val Gly Glu Gly Leu Asn Leu Lys Val
    290                 295                 300

Met Val Glu Ala Tyr Pro Gly Leu Gln Gly Phe Asn Trp Thr Tyr Leu
305                 310                 315                 320

Gly Pro Phe Ser Asp His Gln Pro Glu Pro Lys Leu Ala Asn Ala Thr
                325                 330                 335

Thr Lys Asp Thr Tyr Arg His Thr Phe Thr Leu Ser Leu Pro Arg Leu
            340                 345                 350

Lys Pro Ser Glu Ala Gly Arg Tyr Ser Phe Leu Ala Arg Asn Pro Gly
        355                 360                 365
```

```
Gly Trp Arg Ala Leu Thr Phe Glu Leu Thr Leu Arg Tyr Pro Pro Glu
            370                 375                 380

Val Ser Val Ile Trp Thr Phe Ile Asn Gly Ser Gly Thr Leu Leu Cys
385                 390                 395                 400

Ala Ala Ser Gly Tyr Pro Gln Pro Asn Val Thr Trp Leu Gln Cys Ser
                405                 410                 415

Gly His Thr Asp Arg Cys Asp Glu Ala Gln Val Leu Gln Val Trp Asp
            420                 425                 430

Asp Pro Tyr Pro Glu Val Leu Ser Gln Glu Pro Phe His Lys Val Thr
            435                 440                 445

Val Gln Ser Leu Leu Thr Val Glu Thr Leu Glu His Asn Gln Thr Tyr
450                 455                 460

Glu Cys Arg Ala His Asn Ser Val Gly Ser Gly Ser Trp Ala Phe Ile
465                 470                 475                 480

Pro Ile Ser Ala Gly Ala His Thr His Pro Pro Asp Glu Phe Leu Phe
                485                 490                 495

Thr Pro Ser Lys Tyr Gly Pro Pro Cys Pro Pro Cys Pro Ala Pro Glu
            500                 505                 510

Phe Leu Gly Gly Pro Ser Val Phe Leu Phe Pro Pro Lys Pro Lys Asp
            515                 520                 525

Gln Leu Met Ile Ser Arg Thr Pro Glu Val Thr Cys Val Val Val Asp
530                 535                 540

Val Ser Gln Glu Asp Pro Glu Val Gln Phe Asn Trp Tyr Val Asp Gly
545                 550                 555                 560

Val Glu Val His Asn Ala Lys Thr Lys Pro Arg Glu Glu Gln Phe Asn
                565                 570                 575

Ser Thr Tyr Arg Val Val Ser Val Leu Thr Val Leu His Gln Asp Trp
            580                 585                 590

Leu Ser Gly Lys Glu Tyr Lys Cys Lys Val Ser Ser Lys Gly Leu Pro
            595                 600                 605

Ser Ser Ile Glu Lys Thr Ile Ser Asn Ala Thr Gly Gln Pro Arg Glu
610                 615                 620

Pro Gln Val Tyr Thr Leu Pro Pro Ser Gln Glu Glu Met Thr Lys Asn
625                 630                 635                 640

Gln Val Ser Leu Thr Cys Leu Val Lys Gly Phe Tyr Pro Ser Asp Ile
                645                 650                 655

Ala Val Glu Trp Glu Ser Asn Gly Gln Pro Glu Asn Asn Tyr Lys Thr
            660                 665                 670

Thr Pro Pro Val Leu Asp Ser Asp Gly Ser Phe Phe Leu Tyr Ser Arg
            675                 680                 685

Leu Thr Val Asp Lys Ser Arg Trp Gln Glu Gly Asn Val Phe Ser Cys
690                 695                 700

Ser Val Leu His Glu Ala Leu His Asn His Tyr Thr Gln Lys Ser Leu
705                 710                 715                 720

Ser Leu Ser Leu Gly Lys Ile Glu Gly Arg Met Asp Gln Val Ser His
                725                 730                 735

Arg Tyr Pro Arg Ile Gln Ser Ile Lys Val Gln Phe Thr Glu Tyr Lys
            740                 745                 750

Lys Glu Lys Gly Phe Ile Leu Thr Ser Gln Lys Glu Asp Glu Ile Met
            755                 760                 765

Lys Val Gln Asn Asn Ser Val Ile Ile Asn Cys Asp Gly Phe Tyr Leu
770                 775                 780
```

```
Ile Ser Leu Lys Gly Tyr Phe Ser Gln Glu Val Asn Ile Ser Leu His
785                 790                 795                 800

Tyr Gln Lys Asp Glu Pro Leu Phe Gln Leu Lys Lys Val Arg Ser
            805                 810                 815

Val Asn Ser Leu Met Val Ala Ser Leu Thr Tyr Lys Asp Lys Val Tyr
            820                 825                 830

Leu Asn Val Thr Thr Asp Asn Thr Ser Leu Asp Asp Phe His Val Asn
                835                 840                 845

Gly Gly Glu Leu Ile Leu Ile His Gln Asn Pro Gly Glu Phe Cys Val
    850                 855                 860

Leu
865

<210> SEQ ID NO 9
<211> LENGTH: 254
<212> TYPE: PRT
<213> ORGANISM: Artificial Sequence
<220> FEATURE:
<223> OTHER INFORMATION: Synthetic Polypeptide

<400> SEQUENCE: 9

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
                180                 185                 190

Arg Asn Ser Ala Phe Gly Phe Gln Gly Arg Leu Leu His Leu Ser Ala
            195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 10
<211> LENGTH: 205
```

```
<212> TYPE: PRT
<213> ORGANISM: Artificial Sequence
<220> FEATURE:
<223> OTHER INFORMATION: Synthetic Polypeptide

<400> SEQUENCE: 10

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 11
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 11

Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125
```

```
Gly Asn Leu Val Ile Gln Phe Pro Gly Leu Tyr Phe Ile Ile Cys Gln
        130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
            180                 185                 190

Phe Leu Leu Asp Tyr Leu Gln Val Asn Thr Thr Ile Ser Val Asn Val
                195                 200                 205

Asp Thr Phe Gln Tyr Ile Asp Thr Ser Thr Phe Pro Leu Glu Asn Val
        210                 215                 220

Leu Ser Ile Phe Leu Tyr Ser Asn Ser Asp
225                 230

<210> SEQ ID NO 12
<211> LENGTH: 172
<212> TYPE: PRT
<213> ORGANISM: Artificial Sequence
<220> FEATURE:
<223> OTHER INFORMATION: Synthetic Polypeptide

<400> SEQUENCE: 12

Gln Arg Thr Asp Ser Ile Pro Asn Ser Pro Asp Asn Val Pro Leu Lys
1               5                   10                  15

Gly Gly Asn Cys Ser Glu Asp Leu Leu Cys Ile Leu Lys Arg Ala Pro
            20                  25                  30

Phe Lys Lys Ser Trp Ala Tyr Leu Gln Val Ala Lys His Leu Asn Lys
        35                  40                  45

Thr Lys Leu Ser Trp Asn Lys Asp Gly Ile Leu His Gly Val Arg Tyr
    50                  55                  60

Gln Asp Gly Asn Leu Val Ile Gln Phe Pro Gly Leu Tyr Phe Ile Ile
65                  70                  75                  80

Cys Gln Leu Gln Phe Leu Val Gln Cys Pro Asn Asn Ser Val Asp Leu
                85                  90                  95

Lys Leu Glu Leu Leu Ile Asn Lys His Ile Lys Lys Gln Ala Leu Val
            100                 105                 110

Thr Val Cys Glu Ser Gly Met Gln Thr Lys His Val Tyr Gln Asn Leu
        115                 120                 125

Ser Gln Phe Leu Leu Asp Tyr Leu Gln Val Asn Thr Thr Ile Ser Val
    130                 135                 140

Asn Val Asp Thr Phe Gln Tyr Ile Asp Thr Ser Thr Phe Pro Leu Glu
145                 150                 155                 160

Asn Val Leu Ser Ile Phe Leu Tyr Ser Asn Ser Asp
                165                 170

<210> SEQ ID NO 13
<211> LENGTH: 281
<212> TYPE: PRT
<213> ORGANISM: Artificial Sequence
<220> FEATURE:
<223> OTHER INFORMATION: Synthetic Polypeptide

<400> SEQUENCE: 13

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
```

```
                20                  25                  30
Pro Thr Ser Val Pro Arg Arg Pro Gly Gln Arg Arg Pro Pro Pro
            35                  40                  45

Pro Pro Pro Pro Pro Leu Pro Pro Pro Pro Pro Pro Pro Leu Pro
50                  55                  60

Pro Leu Pro Leu Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
            115                 120                 125

Lys Gln Ile Gly His Pro Ser Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
    210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
            275                 280

<210> SEQ ID NO 14
<211> LENGTH: 179
<212> TYPE: PRT
<213> ORGANISM: Artificial Sequence
<220> FEATURE:
<223> OTHER INFORMATION: Synthetic Polypeptide

<400> SEQUENCE: 14

Gln Leu Phe His Leu Gln Lys Glu Leu Ala Glu Leu Arg Glu Ser Thr
1               5                   10                  15

Ser Gln Met His Thr Ala Ser Ser Leu Glu Lys Gln Ile Gly His Pro
                20                  25                  30

Ser Pro Pro Pro Glu Lys Lys Glu Leu Arg Lys Val Ala His Leu Thr
            35                  40                  45

Gly Lys Ser Asn Ser Arg Ser Met Pro Leu Glu Trp Glu Asp Thr Tyr
        50                  55                  60

Gly Ile Val Leu Leu Ser Gly Val Lys Tyr Lys Lys Gly Gly Leu Val
65                  70                  75                  80

Ile Asn Glu Thr Gly Leu Tyr Phe Val Tyr Ser Lys Val Tyr Phe Arg
                85                  90                  95

Gly Gln Ser Cys Asn Asn Leu Pro Leu Ser His Lys Val Tyr Met Arg
```

```
                    100                 105                 110
Asn Ser Lys Tyr Pro Gln Asp Leu Val Met Met Glu Gly Lys Met Met
        115                 120                 125

Ser Tyr Cys Thr Thr Gly Gln Met Trp Ala Arg Ser Ser Tyr Leu Gly
    130                 135                 140

Ala Val Phe Asn Leu Thr Ser Ala Asp His Leu Tyr Val Asn Val Ser
145                 150                 155                 160

Glu Leu Ser Leu Val Asn Phe Glu Glu Ser Gln Thr Phe Phe Gly Leu
                165                 170                 175

Tyr Lys Leu

<210> SEQ ID NO 15
<211> LENGTH: 199
<212> TYPE: PRT
<213> ORGANISM: Artificial Sequence
<220> FEATURE:
<223> OTHER INFORMATION: Synthetic Polypeptide

<400> SEQUENCE: 15

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
                20                  25                  30

Leu Ser His Ser Arg Thr Gln Gly Ala Gln Arg Ser Ser Trp Lys Leu
            35                  40                  45

Trp Leu Phe Cys Ser Ile Val Met Leu Leu Phe Leu Cys Ser Phe Ser
        50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
                100                 105                 110

Gln Asn Gly Leu Tyr Leu Ile Tyr Gly Gln Val Ala Pro Asn Ala Asn
            115                 120                 125

Tyr Asn Asp Val Ala Pro Phe Glu Val Arg Leu Tyr Lys Asn Lys Asp
        130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195

<210> SEQ ID NO 16
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 16

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
```

```
            20                  25                  30
Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
    50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

Asp Thr Ile Asp Leu Ile Phe Asn Ser Glu His Gln Val Leu Lys Asn
            100                 105                 110

Asn Thr Tyr Trp Gly Ile Ile Leu Leu Ala Asn Pro Gln Phe Ile Ser
            115                 120                 125

<210> SEQ ID NO 17
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 17

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
        130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
            195                 200                 205

Leu Glu Ala Gly Glu Lys Val Val Val Arg Val Leu Asp Glu Arg Leu
        210                 215                 220

Val Arg Leu Arg Asp Gly Thr Arg Ser Tyr Phe Gly Ala Phe Met Val
225                 230                 235                 240

<210> SEQ ID NO 18
<211> LENGTH: 182
<212> TYPE: PRT
```

```
<213> ORGANISM: Artificial Sequence
<220> FEATURE:
<223> OTHER INFORMATION: Synthetic Polypeptide

<400> SEQUENCE: 18

Leu Gln Leu His Trp Arg Leu Gly Glu Met Val Thr Arg Leu Pro Asp
1               5                   10                  15

Gly Pro Ala Gly Ser Trp Glu Gln Leu Ile Gln Glu Arg Arg Ser His
            20                  25                  30

Glu Val Asn Pro Ala Ala His Leu Thr Gly Ala Asn Ser Ser Leu Thr
        35                  40                  45

Gly Ser Gly Gly Pro Leu Leu Trp Glu Thr Gln Leu Gly Leu Ala Phe
    50                  55                  60

Leu Arg Gly Leu Ser Tyr His Asp Gly Ala Leu Val Val Thr Lys Ala
65                  70                  75                  80

Gly Tyr Tyr Tyr Ile Tyr Ser Lys Val Gln Leu Gly Gly Val Gly Cys
                85                  90                  95

Pro Leu Gly Leu Ala Ser Thr Ile Thr His Gly Leu Tyr Lys Arg Thr
            100                 105                 110

Pro Arg Tyr Pro Glu Glu Leu Glu Leu Leu Val Ser Gln Gln Ser Pro
        115                 120                 125

Cys Gly Arg Ala Thr Ser Ser Arg Val Trp Trp Asp Ser Ser Phe
    130                 135                 140

Leu Gly Gly Val Val His Leu Glu Ala Gly Glu Lys Val Val Val Arg
145                 150                 155                 160

Val Leu Asp Glu Arg Leu Val Arg Leu Arg Asp Gly Thr Arg Ser Tyr
                165                 170                 175

Phe Gly Ala Phe Met Val
            180

<210> SEQ ID NO 19

<400> SEQUENCE: 19

000

<210> SEQ ID NO 20

<400> SEQUENCE: 20

000

<210> SEQ ID NO 21
<211> LENGTH: 251
<212> TYPE: PRT
<213> ORGANISM: Artificial Sequence
<220> FEATURE:
<223> OTHER INFORMATION: Synthetic Polypeptide

<400> SEQUENCE: 21

Met Ala Glu Asp Leu Gly Leu Ser Phe Gly Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
```

```
              65                  70                  75                  80
His Gln Gln Val Tyr Ala Pro Leu Arg Ala Asp Gly Asp Lys Pro Arg
                    85                  90                  95

Ala His Leu Thr Val Val Arg Gln Thr Pro Thr Gln His Phe Lys Asn
                100                 105                 110

Gln Phe Pro Ala Leu His Trp Glu His Glu Leu Gly Leu Ala Phe Thr
            115                 120                 125

Lys Asn Arg Met Asn Tyr Thr Asn Lys Phe Leu Leu Ile Pro Glu Ser
        130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 22
<211> LENGTH: 192
<212> TYPE: PRT
<213> ORGANISM: Artificial Sequence
<220> FEATURE:
<223> OTHER INFORMATION: Synthetic Polypeptide

<400> SEQUENCE: 22

Arg Ala Gln Gly Glu Ala Cys Val Gln Phe Gln Ala Leu Lys Gly Gln
1               5                   10                  15

Glu Phe Ala Pro Ser His Gln Gln Val Tyr Ala Pro Leu Arg Ala Asp
            20                  25                  30

Gly Asp Lys Pro Arg Ala His Leu Thr Val Val Arg Gln Thr Pro Thr
        35                  40                  45

Gln His Phe Lys Asn Gln Phe Pro Ala Leu His Trp Glu His Glu Leu
    50                  55                  60

Gly Leu Ala Phe Thr Lys Asn Arg Met Asn Tyr Thr Asn Lys Phe Leu
65                  70                  75                  80

Leu Ile Pro Glu Ser Gly Asp Tyr Phe Ile Tyr Ser Gln Val Thr Phe
                85                  90                  95

Arg Gly Met Thr Ser Glu Cys Ser Glu Ile Arg Gln Ala Gly Arg Pro
            100                 105                 110

Asn Lys Pro Asp Ser Ile Thr Val Val Ile Thr Lys Val Thr Asp Ser
        115                 120                 125

Tyr Pro Glu Pro Thr Gln Leu Leu Met Gly Thr Lys Ser Val Cys Glu
    130                 135                 140

Val Gly Ser Asn Trp Phe Gln Pro Ile Tyr Leu Gly Ala Met Phe Ser
145                 150                 155                 160

Leu Gln Glu Gly Asp Lys Leu Met Val Asn Val Ser Asp Ile Ser Leu
                165                 170                 175

Val Asp Tyr Thr Lys Glu Asp Lys Thr Phe Phe Gly Ala Phe Leu Leu
```

<210> SEQ ID NO 23
<211> LENGTH: 281
<212> TYPE: PRT
<213> ORGANISM: Artificial Sequence
<220> FEATURE:
<223> OTHER INFORMATION: Synthetic Polypeptide

<400> SEQUENCE: 23

```
Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Gly Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280
```

<210> SEQ ID NO 24
<211> LENGTH: 243
<212> TYPE: PRT
<213> ORGANISM: Artificial Sequence
<220> FEATURE:
<223> OTHER INFORMATION: Synthetic Polypeptide

<400> SEQUENCE: 24

```
Thr Asn Glu Leu Lys Gln Met Gln Asp Lys Tyr Ser Lys Ser Gly Ile
1               5                   10                  15
```

```
Ala Cys Phe Leu Lys Glu Asp Asp Ser Tyr Trp Asp Pro Asn Asp Glu
                20                  25                  30

Glu Ser Met Asn Ser Pro Cys Trp Gln Val Lys Trp Gln Leu Arg Gln
        35                  40                  45

Leu Val Arg Lys Met Ile Leu Arg Thr Ser Glu Glu Thr Ile Ser Thr
50                  55                  60

Val Gln Glu Lys Gln Gln Asn Ile Ser Pro Leu Val Arg Glu Arg Gly
65                  70                  75                  80

Pro Gln Arg Val Ala Ala His Ile Thr Gly Thr Arg Gly Arg Ser Asn
                85                  90                  95

Thr Leu Ser Ser Pro Asn Ser Lys Asn Glu Lys Ala Leu Gly Arg Lys
            100                 105                 110

Ile Asn Ser Trp Glu Ser Ser Arg Ser Gly His Ser Phe Leu Ser Asn
            115                 120                 125

Leu His Leu Arg Asn Gly Glu Leu Val Ile His Glu Lys Gly Phe Tyr
        130                 135                 140

Tyr Ile Tyr Ser Gln Thr Tyr Phe Arg Phe Gln Glu Glu Ile Lys Glu
145                 150                 155                 160

Asn Thr Lys Asn Asp Lys Gln Met Val Gln Tyr Ile Tyr Lys Tyr Thr
                165                 170                 175

Ser Tyr Pro Asp Pro Ile Leu Leu Met Lys Ser Ala Arg Asn Ser Cys
            180                 185                 190

Trp Ser Lys Asp Ala Glu Tyr Gly Leu Tyr Ser Ile Tyr Gln Gly Gly
        195                 200                 205

Ile Phe Glu Leu Lys Glu Asn Asp Arg Ile Phe Val Ser Val Thr Asn
210                 215                 220

Glu His Leu Ile Asp Met Asp His Glu Ala Ser Phe Phe Gly Ala Phe
225                 230                 235                 240

Leu Val Gly

<210> SEQ ID NO 25
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 25

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
```

-continued

```
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215
```

<210> SEQ ID NO 26
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 26

```
Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Thr Pro His
65                  70                  75                  80

Ser Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly Lys
    210                 215
```

<210> SEQ ID NO 27
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 27

Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Gln Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly Lys
    210                 215

<210> SEQ ID NO 28
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 28

Ser Lys Tyr Gly Pro Pro Cys Pro Ser Cys Pro
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 29

Ser Lys Tyr Gly Pro Pro Cys Pro Pro Cys Pro
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 30

Ser Lys Tyr Gly Pro Pro

```
<210> SEQ ID NO 31
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 31

Ile Glu Gly Arg Met Asp
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 32

Gly Gly Gly Val Pro Arg Asp Cys Gly
1               5

<210> SEQ ID NO 33
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 33

Ile Glu Gly Arg Met Asp Gly Gly Gly Ala Gly Gly Gly Gly
1               5                   10                  15

<210> SEQ ID NO 34
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 34

Gly Gly Gly Ser Gly Gly Gly Ser
1               5

<210> SEQ ID NO 35
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 35

Gly Gly Gly Ser Gly Gly Gly Ser Gly Gly Gly
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 36

Glu Gly Lys Ser Ser Gly Ser Gly Ser Glu Ser Lys Ser Thr
1               5                   10
```

<210> SEQ ID NO 37
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 37

Gly Gly Ser Gly
1

<210> SEQ ID NO 38
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 38

Gly Gly Ser Gly Gly Gly Ser Gly Gly Gly Ser Gly
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 39

Glu Ala Ala Ala Lys Glu Ala Ala Ala Lys Glu Ala Ala Ala Lys
1               5                   10                  15

<210> SEQ ID NO 40
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 40

Glu Ala Ala Ala Arg Glu Ala Ala Ala Arg Glu Ala Ala Ala Arg Glu
1               5                   10                  15

Ala Ala Ala Arg
            20

<210> SEQ ID NO 41
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 41

Gly Gly Gly Gly Ser Gly Gly Gly Gly Ser Gly Gly Gly Gly Ser Ala
1               5                   10                  15

Ser

<210> SEQ ID NO 42
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 42

Gly Gly Gly Gly Ala Gly Gly Gly Gly
1               5

<210> SEQ ID NO 43

<400> SEQUENCE: 43

000

<210> SEQ ID NO 44
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 44

Gly Ser Gly Ser Gly Ser
1               5

<210> SEQ ID NO 45
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 45

Gly Ser Gly Ser Gly Ser Gly Ser Gly Ser
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 46

Gly Gly Gly Gly Ser Ala Ser
1               5

<210> SEQ ID NO 47
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 47

Ala Pro Ala Pro Ala Pro Ala Pro Ala Pro Ala Pro Ala Pro Ala Pro
1               5                   10                  15

Ala Pro Ala Pro
            20

<210> SEQ ID NO 48
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 48

Cys Pro Pro Cys
1

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Gly Gly Gly Gly Ser
1               5

<210> SEQ ID NO 50
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 50

Gly Gly Gly Gly Ser Gly Gly Gly Gly Ser
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 51

Gly Gly Gly Gly Ser Gly Gly Gly Gly Ser Gly Gly Gly Gly Ser
1               5                   10                  15

<210> SEQ ID NO 52
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 52

Gly Gly Gly Gly Ser Gly Gly Gly Gly Ser Gly Gly Gly Gly Ser Gly
1               5                   10                  15

Gly Gly Gly Ser
            20

<210> SEQ ID NO 53
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 53

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 54
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 54

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser
            20                  25                  30

<210> SEQ ID NO 55
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 55

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser
        35

<210> SEQ ID NO 56
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 56

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser
        35                  40

<210> SEQ ID NO 57
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 57

Gly Gly Ser Gly Gly Ser Gly Gly Gly Gly Ser Gly Gly Gly Gly Ser
1               5                   10                  15

<210> SEQ ID NO 58
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 58

Gly Gly Gly Gly Gly Gly Gly Gly
1               5

<210> SEQ ID NO 59
<211> LENGTH: 6
<212> TYPE: PRT
<213> ORGANISM: Artificial Sequence
<220> FEATURE:

```
<223> OTHER INFORMATION: Synthetic Polypeptide

<400> SEQUENCE: 59

Gly Gly Gly Gly Gly Gly
1               5

<210> SEQ ID NO 60
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 60

Glu Ala Ala Ala Lys
1               5

<210> SEQ ID NO 61
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 61

Glu Ala Ala Ala Lys Glu Ala Ala Ala Lys
1               5                   10

<210> SEQ ID NO 62
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 62

Glu Ala Ala Ala Lys Glu Ala Ala Ala Lys Glu Ala Ala Ala Lys
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 63

Ala Glu Ala Ala Ala Lys Glu Ala Ala Ala Lys Ala
1               5                   10

<210> SEQ ID NO 64
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 64

Ala Glu Ala Ala Ala Lys Glu Ala Ala Ala Lys Glu Ala Ala Ala Lys
1               5                   10                  15

Ala

<210> SEQ ID NO 65
<211> LENGTH: 22
<212> TYPE: PRT
<213> ORGANISM: Artificial Sequence
```

```
<220> FEATURE:
<223> OTHER INFORMATION: Synthetic Polypeptide

<400> SEQUENCE: 65

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 66
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 66

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 67
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 67

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Lys Glu Ala
            20                  25                  30

Ala Ala Lys Glu Ala Ala Ala Lys Glu Ala Ala Ala Lys Ala
        35                  40                  45

<210> SEQ ID NO 68
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 68

Pro Ala Pro Ala Pro
1               5

<210> SEQ ID NO 69
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 69

Lys Glu Ser Gly Ser Val Ser Ser Glu Gln Leu Ala Gln Phe Arg Ser
1               5                   10                  15

Leu Asp

<210> SEQ ID NO 70
<211> LENGTH: 12
<212> TYPE: PRT
<213> ORGANISM: Artificial Sequence
```

```
<220> FEATURE:
<223> OTHER INFORMATION: Synthetic Polypeptide

<400> SEQUENCE: 70

Gly Ser Ala Gly Ser Ala Ala Gly Ser Gly Glu Phe
1               5                   10

<210> SEQ ID NO 71
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 71

Gly Gly Gly Ser Glu
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 72

Gly Ser Glu Ser Gly
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 73

Gly Ser Glu Gly Ser
1               5

<210> SEQ ID NO 74
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 74

Gly Glu Gly Gly Ser Gly Glu Gly Ser Ser Gly Glu Gly Ser Ser
1               5                   10                  15

Glu Gly Gly Gly Ser Glu Gly Gly Ser Glu Gly Gly Ser Glu
            20                  25                  30

Gly Gly Ser
        35

<210> SEQ ID NO 75
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 75

Ser Lys Tyr Gly Pro Pro Cys Pro Ser Cys Pro Ala Pro Glu Phe Leu
1               5                   10                  15
```

```
Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 76
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 76

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Thr Pro His Ser Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140
```

```
Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 77
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 77

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 78
<211> LENGTH: 234
<212> TYPE: PRT
<213> ORGANISM: Artificial Sequence
<220> FEATURE:
```

<223> OTHER INFORMATION: Synthetic Polypeptide

<400> SEQUENCE: 78

Ser Lys Tyr Gly Pro Pro Cys Pro Pro Cys Pro Ala Pro Glu Phe Leu
1               5                   10                  15
Gly Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
Gln Glu Asp Pro Glu Val Gln Phe Asn Trp Tyr Val Asp Gly Val Glu
    50                  55                  60
Val His Asn Ala Lys Thr Lys Pro Arg Glu Glu Gln Phe Asn Ser Thr
65                  70                  75                  80
Tyr Arg Val Val Ser Val Leu Thr Val Leu His Gln Asp Trp Leu Ser
                85                  90                  95
Gly Lys Glu Tyr Lys Cys Lys Val Ser Ser Lys Gly Leu Pro Ser Ser
            100                 105                 110
Ile Glu Lys Thr Ile Ser Asn Ala Thr Gly Gln Pro Arg Glu Pro Gln
        115                 120                 125
Val Tyr Thr Leu Pro Pro Ser Gln Glu Glu Met Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Val Leu Asp Ser Asp Gly Ser Phe Phe Leu Tyr Ser Arg Leu Thr
            180                 185                 190
Val Asp Lys Ser Ser Trp Gln Glu Gly Asn Val Phe Ser Cys Ser Val
        195                 200                 205
Met His Glu Ala Leu His Asn His Tyr Thr Gln Lys Ser Leu Ser Leu
    210                 215                 220
Ser Leu Gly Lys Ile Glu Gly Arg Met Asp
225                 230

<210> SEQ ID NO 79
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 79

Ser Lys Tyr Gly Pro Pro Cys Pro Pro Cys Pro Ala Pro Glu Phe Leu
1               5                   10                  15
Gly Gly Pro Ser Val Phe Leu Phe Pro Pro Lys Pro Lys Asp Gln Leu
            20                  25                  30
Met Ile Ser Arg Thr Pro Glu Val Thr Cys Val Val Val Asp Val Ser
        35                  40                  45
Gln Glu Asp Pro Glu Val Gln Phe Asn Trp Tyr Val Asp Gly Val Glu
    50                  55                  60
Val His Asn Ala Lys Thr Lys Pro Arg Glu Glu Gln Phe Asn Ser Thr
65                  70                  75                  80
Tyr Arg Val Val Ser Val Leu Thr Thr Pro His Ser Asp Trp Leu Ser
                85                  90                  95
Gly Lys Glu Tyr Lys Cys Lys Val Ser Ser Lys Gly Leu Pro Ser Ser
            100                 105                 110

```
Ile Glu Lys Thr Ile Ser Asn Ala Thr Gly Gln Pro Arg Glu Pro Gln
            115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
                180                 185                 190

Val Asp Lys Ser Ser Trp Gln Glu Gly Asn Val Phe Ser Cys Ser Val
            195                 200                 205

Leu His Glu Ala Leu His Asn His Tyr Thr Gln Lys Ser Leu Ser Leu
            210                 215                 220

Ser Leu Gly Lys Ile Glu Gly Arg Met Asp
225                 230

<210> SEQ ID NO 80
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 80

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
                20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
                100                 105                 110

Ile Glu Lys Thr Ile Ser Asn Ala Thr Gly Gln Pro Arg Glu Pro Gln
            115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
                180                 185                 190

Val Asp Lys Ser Arg Trp Gln Glu Gly Asn Val Phe Ser Cys Ser Val
            195                 200                 205
```

```
Leu His Glu Ala Leu His Asn His Tyr Thr Gln Lys Ser Leu Ser Leu
    210                 215                 220

Ser Leu Gly Lys Ile Glu Gly Arg Met Asp
225                 230
```